United States Patent
Kubota et al.

(10) Patent No.: US 9,475,991 B2
(45) Date of Patent: Oct. 25, 2016

(54) POLYMERIZABLE LIQUID CRYSTAL COMPOSITION, POLARIZED LIGHT-EMITTING COATING MATERIAL, NOVEL NAPHTHOLACTAM DERIVATIVE NOVEL COUMARIN DERIVATIVE, NOVEL NILE RED DERIVATIVE, AND NOVEL ANTHRACENE DERIVATIVE

(75) Inventors: Yusuke Kubota, Tokyo (JP); Masatomi Irisawa, Tokyo (JP); Toru Yano, Tokyo (JP); Ken Matsumoto, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 267 days.

(21) Appl. No.: 14/002,363

(22) PCT Filed: Mar. 15, 2012

(86) PCT No.: PCT/JP2012/056708
§ 371 (c)(1),
(2), (4) Date: Aug. 30, 2013

(87) PCT Pub. No.: WO2012/132936
PCT Pub. Date: Oct. 4, 2012

(65) Prior Publication Data
US 2013/0334461 A1    Dec. 19, 2013

(30) Foreign Application Priority Data

Mar. 30, 2011 (JP) ................... 2011-075698
Dec. 7, 2011 (JP) ................... 2011-268370

(51) Int. Cl.
| | | |
|---|---|---|
| C09K 19/60 | (2006.01) | |
| C09K 19/34 | (2006.01) | |
| G02B 5/30 | (2006.01) | |
| C07D 311/06 | (2006.01) | |
| C07D 265/34 | (2006.01) | |
| C09B 57/02 | (2006.01) | |
| C09K 19/54 | (2006.01) | |
| C07D 265/36 | (2006.01) | |
| C07D 265/38 | (2006.01) | |
| C09K 19/32 | (2006.01) | |
| C09B 57/06 | (2006.01) | |
| C09B 69/10 | (2006.01) | |
| C08G 59/00 | (2006.01) | |
| C08L 63/00 | (2006.01) | |
| C09K 19/04 | (2006.01) | |
| H01L 51/52 | (2006.01) | |
| C08F 220/30 | (2006.01) | |

(52) U.S. Cl.
CPC ............ *C09K 19/54* (2013.01); *C07D 265/34* (2013.01); *C07D 265/36* (2013.01); *C07D 265/38* (2013.01); *C07D 311/06* (2013.01); *C08G 59/00* (2013.01); *C08L 63/00* (2013.01); *C09B 57/02* (2013.01); *C09B 57/06* (2013.01); *C09B 69/101* (2013.01); *C09B 69/109* (2013.01); *C09K 19/32* (2013.01); *C09K 19/3483* (2013.01); *C09K 19/3486* (2013.01); *C09K 19/60* (2013.01); *G02B 5/3025* (2013.01); *C08F 220/30* (2013.01); *C09K 2019/0448* (2013.01); *H01L 51/5293* (2013.01)

(58) Field of Classification Search
CPC .............. C09K 19/32; C09K 19/3484; C09K 19/3486; C09K 19/54; C09K 19/60; C09K 2019/0448; C09B 57/02; G02B 5/3025; C07D 265/36; C07D 265/38; C07D 311/06
See application file for complete search history.

(56) References Cited

U.S. PATENT DOCUMENTS

| | | |
|---|---|---|
| 7,632,906 B2 | 12/2009 | Studer et al. |
| 7,907,247 B2 | 3/2011 | Okabe et al. |
| 8,350,054 B2 | 1/2013 | Mae et al. |
| 8,475,033 B2 | 7/2013 | Debije et al. |
| 8,530,740 B2 | 9/2013 | Debije et al. |
| 8,592,007 B2 | 11/2013 | Goetz et al. |
| 2003/0106994 A1 | 6/2003 | Sage |
| 2007/0179266 A1 | 8/2007 | Studer |
| 2008/0098488 A1 | 4/2008 | Schadt et al. |
| 2008/0135098 A1 | 6/2008 | Ootani et al. |
| 2009/0027872 A1 | 1/2009 | Debije et al. |

(Continued)

FOREIGN PATENT DOCUMENTS

| | | |
|---|---|---|
| DE | 102009043436 | 5/2010 |
| EP | 1890187 | 2/2008 |

(Continued)

OTHER PUBLICATIONS

International Search Report—PCT/JP2012/056708—Jun. 19, 2012.
(Continued)

*Primary Examiner* — Shean C Wu
(74) *Attorney, Agent, or Firm* — Young & Thompson

(57) ABSTRACT

Provided are a polymerizable liquid crystal composition, a coating material, a medium, and a polarizing device each produced using a polymerizable liquid crystal compound and a colorant and each capable of producing polarized light suitable for polarizing devices, and also a novel naphtholactam derivative, a novel coumarin derivative, a novel Nile Red derivative, and a novel anthracene derivative each suitable for use as the colorant. Specifically provided are a polymerizable liquid crystal composition containing (A) at least one liquid crystal compound having a polymerizable functional group, (B) at least one colorant, and (C) a polymerization initiator, and a novel naphtholactam derivative of formula (IV'), a novel coumarin derivative of formula (VI'), a novel Nile Red derivative of formula (VII'), and a novel anthracene derivative of formula (VIII') each suitable for use as the colorant (B).

9 Claims, No Drawings

(56) References Cited

U.S. PATENT DOCUMENTS

| | | |
|---|---|---|
| 2009/0044861 A1 | 2/2009 | Debije et al. |
| 2009/0051854 A1 | 2/2009 | Okabe et al. |
| 2009/0137761 A1 | 5/2009 | Irisawa et al. |
| 2010/0066950 A1 | 3/2010 | Cho et al. |
| 2010/0086704 A1 | 4/2010 | Chen et al. |
| 2010/0314995 A1 | 12/2010 | Ikeda et al. |
| 2011/0152538 A1 | 6/2011 | Mae et al. |
| 2011/0205482 A1 | 8/2011 | Goetz et al. |

FOREIGN PATENT DOCUMENTS

| | | |
|---|---|---|
| JP | 63-135458 | 6/1988 |
| JP | 06-234806 | 8/1994 |
| JP | 08-020614 | 1/1996 |
| JP | 10-321371 | 12/1998 |
| JP | 11-74077 | 3/1999 |
| JP | 11-130817 | 5/1999 |
| JP | 2000-87027 | 3/2000 |
| JP | 2004182678 | 7/2004 |
| JP | 2004-535483 | 11/2004 |
| JP | 2005-100782 | 4/2005 |
| JP | 2005-258430 | 9/2005 |
| JP | 2006-143862 | 6/2006 |
| JP | 2007-119415 | 5/2007 |
| JP | 2007-297606 | 11/2007 |
| JP | 2008-536953 | 9/2008 |
| JP | 2009-249586 | 10/2009 |
| JP | 2010-150425 | 7/2010 |
| JP | 2011-195587 | 10/2011 |
| WO | 2005014677 | 2/2005 |
| WO | 2006088369 | 8/2006 |
| WO | 2010/057984 | 5/2010 |
| WO | 2011010537 | 1/2011 |

OTHER PUBLICATIONS

Extended European Search Report (EESR), dated May 22, 2015; Application No: 12765873.0-1357.

D. Reiser et al.: "Picosecond Polarization Spectroscopy of Dye Molecules", pp. 1106-1114; Ber. Bunsenges, Phys. Chem. 86, (1982)-Verlag Chemie GmbH, D-6940 Weinheim, 1982.

POLYMERIZABLE LIQUID CRYSTAL COMPOSITION, POLARIZED LIGHT-EMITTING COATING MATERIAL, NOVEL NAPHTHOLACTAM DERIVATIVE NOVEL COUMARIN DERIVATIVE, NOVEL NILE RED DERIVATIVE, AND NOVEL ANTHRACENE DERIVATIVE

TECHNICAL FIELD

The invention relates to polymerizable liquid crystal composition containing a liquid crystal compound having a polymerizable functional group, a colorant, and a polymerization initiator, to a polarized light-emitting coating material including the polymerizable liquid crystal composition, to a polarized light-emitting laminate obtained by applying the polarized light-emitting coating material to a support, and to a polarizing device including the laminate The invention also relates to a novel naphtholactam derivative, a novel coumarin derivative, a novel Nile Red derivative, and a novel anthracene derivative, which are suitable for use as the colorant.

BACKGROUND ART

A liquid crystal composition containing at least one liquid crystal compound having a polymerizable functional group (hereinafter, such a composition is referred to as a "polymerizable liquid crystal composition," and such a compound is referred to as a "polymerizable liquid crystal compound") can be uniformly oriented in the liquid crystalline state and then exposed to active energy rays such as ultraviolet rays while the liquid crystalline state is maintained, so that an optically anisotropic film can be formed containing a polymer in which the oriented structure of the liquid crystal molecule is semi-permanently fixed. The polymer obtained in this manner is anisotropic in its physical properties such as refractive index, dielectric constant, magnetic susceptibility, elastic modulus, and coefficient of thermal expansion. For example, therefore, the polymer can be used to form shaped products having optical anisotropy, such as retardation plates, polarizing plates, polarizing prisms, brightness enhancement films, low-pass filters, various optical filters, optical fiber coating materials, waveguides, piezoelectric devices, and nonlinear optical devices. Other properties than the anisotropy are also important for the optically anisotropic products obtained by polymerization (polymers). Such properties include polymerization rate, polymer transparency, dynamic strength, coatability, solubility, crystallinity, shrink properties, water permeability, water absorbing capacity, melting point, glass transition point, clearing point, chemical resistance, heat resistance, etc.

Patent Literatures 1 to 5 disclose image displays produced using polymerizable liquid crystal compounds. However, these literatures merely disclose polymerizable liquid crystal compounds that can emit light by themselves or can improve color purity when used together with fluorescent materials, and do not disclose or suggest the polarized light-emitting device produced using a polymerizable liquid crystal compound and a colorant according to the invention.

Patent Literature 6 discloses a system for indicating the authenticity of an article by detecting polarized fluorescent or phosphorescent radiation emitted from a fluorescent material upon illumination. Patent Literature 7 discloses an optical component protected from counterfeiting using an oriented fluorescent dye. However, these literatures do not disclose or suggest the polarized light-emitting device produced using a polymerizable liquid crystal compound and a colorant according to the invention.

CITATION LIST

Patent Literature

Patent Literature 1: Japanese Patent Application Laid-Open (JP-A) No. 2004-182678
Patent Literature 2: US 2009/0137761 A
Patent Literature 3: US 2010/0066950 A
Patent Literature 4: US 2008/0135098 A
Patent Literature 5: US 2010/0314995 A
Patent Literature 6: US 2003/0106994 A
Patent Literature 7: US 2008/0098488 A

SUMMARY OF INVENTION

Technical Problem

It is therefore an object of the invention to provide a polymerizable liquid crystal composition, a coating material, a medium, and a polarizing device each produced using a polymerizable liquid crystal compound and a colorant and each capable of producing polarized light suitable for polarizing devices.

It is another object of the invention to provide a novel naphtholactam derivative, a novel coumarin derivative, a novel Nile Red derivative, and a novel anthracene derivative each suitable for use as the colorant.

Solution to Problem

As a result of studies on various polymerizable liquid crystal compounds and colorants to solve the problems, the inventors have accomplished the invention based on the finding that a polymerizable liquid crystal composition including a combination of a polymerizable liquid crystal compound having a specific chemical structure and a colorant can produce polarized light suitable for polarizing devices and that a novel naphtholactam derivative, a novel coumarin derivative, a novel Nile Red derivative, and a novel anthracene derivative each having a specific structure are suitable for use as the colorant.

Specifically, the invention achieves the objects by providing a polymerizable liquid crystal composition containing (A) at least one liquid crystal compound having a polymerizable functional group, (B) at least one colorant, and (C) a polymerization initiator.

The invention also provides a polarized light-emitting coating material including the polymerizable liquid crystal composition.

The invention also provides a polarized light-emitting laminate obtained by applying the polarized light-emitting coating material to a support.

The invention also provides a polarized light-emitting laminate containing a polymer obtained by photopolymerization of the polymerizable liquid crystal composition.

The invention also provides a polarizing device produced using the laminate.

The invention also provides a naphtholactam derivative represented by formula (IV') below.

[Chemical Formula 1]

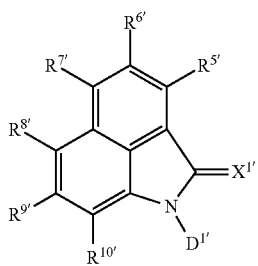

(IV')

wherein $X^{1'}$ represents an oxygen atom or a sulfur atom, $R^{5'}$ to $R^{10'}$ and $D^{1'}$ each independently represent a hydrogen atom, a halogen atom, a nitro group, a cyano group, an aldehyde group, a carboxyl group, a hydroxyl group, —NR"R'", an organosilyl group, an optionally substituted alkyl group of 1 to 30 carbon atoms, an optionally substituted aryl group of 6 to 30 carbon atoms, an optionally substituted arylalkyl group of 7 to 30 carbon atoms, or a substituent represented by formula (V'), a methylene chain in the alkyl group or the arylalkyl group represented by each of $R^{5'}$ to $R^{10'}$ and $D^{1'}$ may be interrupted by —O—, —S—, —SO$_2$—, —CO—, —OCO—, or —COO—, the aryl group represented by each of $R^{5'}$ to $R^{10'}$ and $D^{1'}$ and the naphtholactam structure may be linked together via —O—, —S—, —SO$_2$—, —CO—, —OCO—, or —COO—, and the methylene chain may be replaced by —C=C— or —C≡C—, R" and R'" each independently represent a hydrogen atom, an optionally substituted alkyl group of 1 to 30 carbon atoms, or an optionally substituted aryl group of 6 to 30 carbon atoms, a methylene chain in the alkyl group represented by each of R" and R'" may be interrupted by —O—, —S—, —SO$_2$—, —CO—, —OCO—, or —COO—, the aryl group represented by each of R" and R'" and the naphtholactam structure may be linked together via —O—, —S—, —SO$_2$—, —CO—, —OCO—, or —COO—, and or —C≡C—, and at least one of $R^{5'}$ to $R^{10'}$ represents a substituent represented by formula (V'), wherein formula (V') is the following:

[Chemical Formula 2]

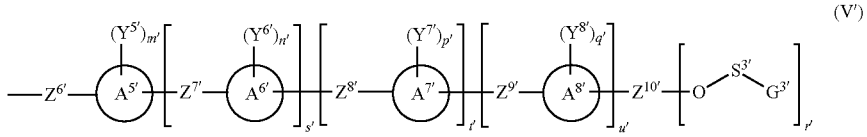

(V')

wherein rings $A^{5'}$, $A^{6'}$, $A^{7'}$, and $A^{8'}$ each independently represent a benzene ring, a cyclohexane ring, a cyclohexene ring, a naphthalene ring, a decahydronaphthalene ring, or a tetrahydronaphthalene ring, $S^{3'}$ represents an alkylene group of 1 to 8 carbon atoms, the alkylene group represented by $S^{3'}$ may be substituted with a halogen atom and branched, and a methylene chain in the alkylene group represented by $S^{3'}$ may be interrupted by —O—, $Z^{6'}$, $Z^{7'}$, $Z^{8'}$, $Z^{9'}$, and $Z^{10'}$ each independently represent a direct bond, $-L^{2'}-$, —O—CO—, —CO—O—, $-L^{2'}$O—, —OL$^{2'}$-, $-L^{2'}$O—CO—, $-L^{2'}$CO—O—, $-L^{2'}$O—CO—O—, —O—COL$^{2'}$-, —CO—OL$^{2'}$-, —O—CO—OL$^{2'}$-, —CO—CH=CH—, —CH=CH—CO—, —CH=CH—COO—, —CH=CH—OCO—, —COO—CH=CH—, —OCO—CH=CH—, or —CH$_2$=N—N=CH$_2$—, $L^{2'}$ represents an alkylene group of 1 to 8 carbon atoms, the alkylene group may be branched and may be substituted with a halogen atom or a cyano group, and a methylene chain in the alkylene group represented by $L^{2'}$ may be interrupted by —O—, —CH=CH—, or —C≡C—, $Y^{5'}$, $Y^{6'}$, $Y^{7'}$, and $Y^{8'}$ each independently represent an alkyl group of 1 to 6 carbon atoms, a halogen atom, or a cyano group, a hydrogen atom of the alkyl group represented by each of $Y^{5'}$, $Y^{6'}$, $Y^{7'}$ and $Y^{8'}$ may be substituted with a halogen atom or a cyano group, and a methylene chain in the alkyl group represented by each of $Y^{5'}$, $Y^{6'}$, $Y^{7'}$ and $Y^{8'}$ may be interrupted by —O— or —CO—, m', n', p', and q' are each independently from 0 to 8, s', t', and u' are each independently 0 or 1, r' is 1 or 2, and $G^{3'}$ represents a substituent selected from the group consisting of substituents represented by formulae (5') to (14') below:

[Chemical Formula 3]

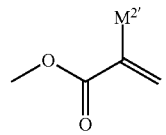 (5')

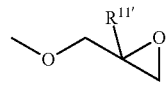 (6')

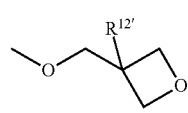 (7')

-continued

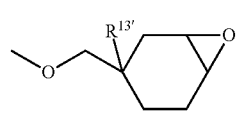 (8')

 (9')

-continued

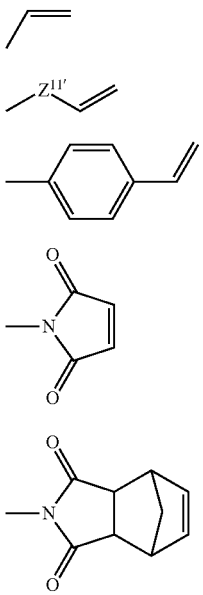

wherein in formula (5'), $M^{2'}$ represents a hydrogen atom, a methyl group, or a halogen atom; in formula (6'), $R^{11'}$ represents a hydrogen atom or an alkyl group of 1 to 6 carbon atoms; in formula (7'), $R^{12'}$ represents a hydrogen atom or an alkyl group of 1 to 6 carbon atoms; in formula (8'), $R^{13'}$ represents a hydrogen atom or an alkyl group of 1 to 6 carbon atoms; in formula (9'), $R^{14'}$ represents a hydrogen atom or an alkyl group of 1 to 6 carbon atoms; and in formula (11'), $Z^{11'}$ represents methylene, an oxygen atom, or —CO—.

The invention also provides a coumarin derivative represented by formula (VI') below.

[Chemical Formula 4]

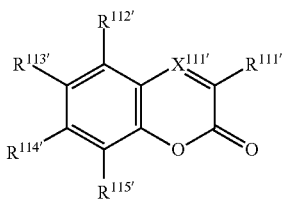

wherein $X^{111'}$ represents a nitrogen atom or $CR^{116'}$, $R^{111'}$ to $R^{116'}$ each independently represent a hydrogen atom, a halogen atom, a nitro group, a cyano group, an aldehyde group, a carboxyl group, a hydroxyl group, —NR''R''', an organosilyl group, an optionally substituted alkyl group of 1 to 30 carbon atoms, an optionally substituted aryl group of 6 to 30 carbon atoms, an optionally substituted arylalkyl group of 7 to 30 carbon atoms, an optionally substituted heterocyclic group of 2 to 30 carbon atoms, or a substituent represented by formula (V') above, a methylene chain in the alkyl group or the arylalkyl group represented by each of $R^{111'}$ to $R^{116'}$ may be interrupted by —O—, —S—, —SO$_2$—, —CO—, —OCO—, or —COO—, the aryl group represented by each of $R^{111'}$ to $R^{116'}$ and the coumarin structure may be linked together via —O—, —S—, —SO$_2$—, —CO—, —OCO—, or —COO—, and the methylene chain may be replaced by —CH=CH— or —C≡C—, adjacent two or more of $R^{111'}$ to $R^{116'}$ may be linked together to form a ring, or when any one of $R^{111'}$ to $R^{116'}$ is —NR'R''', R'' or R''' and any other one of $R^{111'}$ to $R^{116'}$ adjacent thereto may be linked together to form a ring, R'' and R''' each independently represent a hydrogen atom, an optionally substituted alkyl group of 1 to 30 carbon atoms, or an optionally substituted aryl group of 6 to 30 carbon atoms, a methylene chain in the alkyl group represented by each of R'' and R''' may be interrupted by —O—, —S—, —SO$_2$—, —CO—, —OCO—, or —COO—, the aryl group represented by each of R'' and R''' and the coumarin structure may be linked together via —O—, —S—, —SO$_2$—, —CO—, —OCO—, or —COO—, and the methylene chain may be replaced by —C=C— or —C≡C—, and at least one of $R^{111'}$ to $R^{116'}$ represents a substituent represented by formula (V') above.

The invention also provides a Nile Red derivative represented by formula (VII') below.

[Chemical Formula 5]

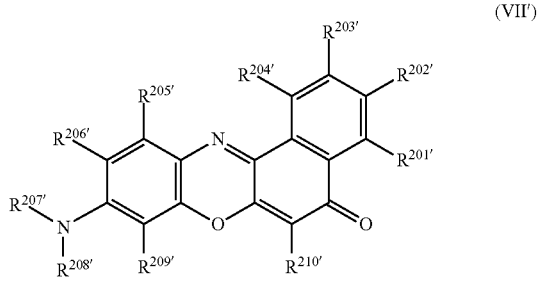

wherein $R^{201'}$ to $R^{206'}$, $R^{209'}$, and $R^{210'}$ each independently represent a hydrogen atom, a halogen atom, a nitro group, a cyano group, an aldehyde group, a carboxyl group, a hydroxyl group, —NR''R''', an organosilyl group, an optionally substituted alkyl group of 1 to 30 carbon atoms, an optionally substituted aryl group of 6 to 30 carbon atoms, an optionally substituted arylalkyl group of 7 to 30 carbon atoms, an optionally substituted heterocyclic group of 2 to 30 carbon atoms, or a substituent represented by formula (V') above, a methylene chain in the alkyl group or the arylalkyl group represented by each of $R^{201'}$ to $R^{206'}$, $R^{209'}$, and $R^{210'}$ may be interrupted by —O—, —S—, —SO$_2$—, —CO—, —OCO—, or —COO—, the aryl group represented by each of $R^{201'}$ to $R^{206'}$, $R^{209'}$, and $R^{210'}$ and the Nile Red structure may be linked together via —O—, —S—, —SO$_2$—, —CO—, —OCO—, or —COO—, and the methylene chain may be replaced by —CH=CH— or —C≡C—, adjacent two or more of $R^{201'}$ to $R^{206'}$ may be linked together to form a ring, or when any one of $R^{201'}$ to $R^{206'}$ is —NR'R''', R'' or R''' and any other one of $R^{201'}$ to $R^{206'}$ adjacent thereto may be linked together to form a ring, $R^{207'}$ and $R^{208'}$ each independently represent an alkyl group of 1 to 10 carbon atoms, R'' and R''' each independently represent a hydrogen atom, an optionally substituted alkyl group of 1 to 30 carbon atoms, or an optionally substituted aryl group of 6 to 30 carbon atoms, a methylene chain in the alkyl group represented by each of R'' and R''' may be interrupted by —O—, —S—, —SO$_2$—, —CO—, —OCO—, or —COO—, the aryl group represented by each of R" and R'" and the Nile Red structure may be linked together via —O—, —S—, —SO$_2$—, —CO—, —OCO—, or —COO—, and the methylene chain may be replaced by —C=C— or —C≡C—, and at least one of R$^{R201'}$ to R$^{206'}$, R$^{209'}$, and R$^{210'}$ represents a substituent represented by formula (V') above.

The invention also provides an anthracene derivative represented by formula (VIII') below.

[Chemical Formula 6]

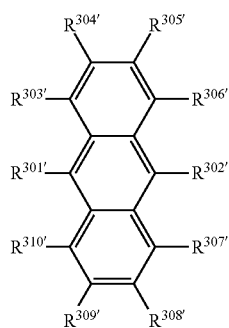

(VIII')

wherein

R$^{301'}$ to R$^{310'}$ each independently represent a hydrogen atom, a halogen atom, a nitro group, a cyano group, an aldehyde group, a carboxyl group, a hydroxyl group, —NR"R'", an organosilyl group, an optionally substituted alkyl group of 1 to 30 carbon atoms, an optionally substituted aryl group of 6 to 30 carbon atoms, an optionally substituted arylalkyl group of 7 to 30 carbon atoms, an optionally substituted heterocyclic group of 2 to 30 carbon atoms, a substituent represented by formula (V') above, or a substituent represented by formula (IX'), at least one of R$^{301'}$ to R$^{310'}$ represents a substituent represented by formula (IX'), a methylene chain in the alkyl group or the arylalkyl group represented by each of R$^{301'}$ to R$^{310'}$ may be interrupted by —O—, —S—, —SO$_2$—, —CO—, —OCO—, or —COO—, the aryl group represented by each of R$^{301'}$ to R$^{310'}$ and the anthracene structure may be linked together via —O—, —S—, —SO$_2$—, —CO—, —OCO—, or —COO—, and the methylene chain may be replaced by —CH=CH— or —C≡C—, adjacent two or more of R$^{301'}$ to R$^{310'}$ may be linked together to form a ring, or when any one of R$^{301'}$ to R$^{310'}$ is —NR'R'", R" or R'" and any other one of R$^{301'}$ to R$^{310'}$ adjacent thereto may be linked together to form a ring, R" and R'" each independently represent a hydrogen atom, an optionally substituted alkyl group of 1 to 30 carbon atoms, or an optionally substituted aryl group of 6 to 30 carbon atoms, a methylene chain in the alkyl group represented by each of R" and R'" may be interrupted by —O—, —S—, —SO$_2$—, —CO—, —OCO—, or —COO—, the aryl group represented by each of R" and R'" and the anthracene structure may be linked together via —O—, —S—, —SO$_2$—, —CO—, —OCO—, or —COO—, and the methylene chain may be replaced by —C=C— or —C≡C—, and at least one of R$^{301'}$ to R$^{310'}$ represents a substituent represented by formula (V') above, wherein formula (IX') is the following:

[Chemical Formula 7]

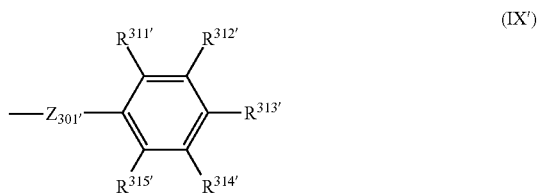

(IX')

wherein

Z$^{301'}$ represents a single bond, an alkylene group of 1 to 4 carbon atoms, —O—, —S—, —SO$_2$—, —CO—, —OCO—, —COO—, —CH=CH—, or —C≡C—, R$^{311'}$ to R$^{315'}$ each independently represent a hydrogen atom, a halogen atom, a nitro group, a cyano group, an aldehyde group, a carboxyl group, a hydroxyl group, —NR"R'", an organosilyl group, an optionally substituted alkyl group of 1 to 30 carbon atoms, an optionally substituted aryl group of 6 to 30 carbon atoms, an optionally substituted arylalkyl group of 7 to 30 carbon atoms, an optionally substituted heterocyclic group of 2 to 30 carbon atoms, or a substituent represented by formula (V') above, and R" and R'" each independently represent a hydrogen atom, an optionally substituted alkyl group of 1 to 30 carbon atoms, or an optionally substituted aryl group of 6 to 30 carbon atoms.

Advantageous Effects of Invention

The polymerizable liquid crystal composition of the invention can produce polarized light suitable for polarizing devices. In particular, polarized light with a high degree of polarization can be generated using the novel naphtholactam derivative, the novel coumarin derivative, the novel Nile Red derivative, or the novel anthracene derivative of the invention as a dye compound. In addition, even selective refection can be obtained at a specific wavelength using an optically active group-containing polymerizable liquid crystal compound as the liquid crystal compound.

DESCRIPTION OF EMBODIMENTS

Hereinafter, the invention will be described in detail with reference to preferred embodiments.

The polymerizable liquid crystal composition of the invention contains (A) at least one liquid crystal compound having a polymerizable functional group (hereinafter also referred to as the polymerizable liquid crystal compound (A)), (B) at least one colorant, and (C) a polymerization initiator. Hereinafter, each component will be described in turn.

<Polymerizable Liquid Crystal Compound (A)>

The liquid crystal compound having a polymerizable functional group may be of any known type. In particular, however, the liquid crystal compound having a polymerizable functional group is preferably the compound represented by formula (I) below because it is low-cost, shows a liquid crystal phase in a wide temperature range, and has good heat resistance.

[Chemical Formula 8]

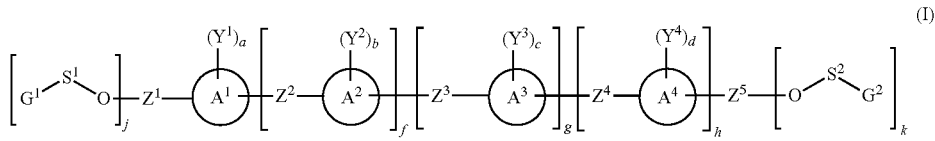

wherein rings $A^1$, $A^2$, $A^3$, and $A^4$ each independently represent a benzene ring, a cyclohexane ring, a cyclohexene ring, a naphthalene ring, an anthracene ring, a phenanthrene ring, a decahydronaphthalene ring, a tetrahydronaphthalene ring, or an optically active linking group, $S^1$ and $S^2$ each independently represent an alkylene group of 1 to 8 carbon atoms, the alkylene group represented by each of $S^1$ and $S^2$ may be substituted with a halogen atom and may be branched, and a methylene chain in the alkylene group represented by each of $S^1$ and $S^2$ may be interrupted by —O—, $Z^1$, $Z^2$, $Z^3$, $Z^4$, and $Z^5$ each independently represent a direct bond, -$L^1$-, —O—CO—, —CO—O—, -$L^1$O—, —O$L^1$-, -$L^1$O—CO—, -$L^1$CO—O—, -$L^1$O—CO—O—, —O—CO$L^1$-, —CO—O$L^1$-, —O—CO—O$L^1$-, —CO—CH=CH—, —CH=CH—CO—, —CH=CH—COO—, —CH=CH—OCO—, —COO—CH=CH—, —OCO—CH=CH—, or —CH$_2$=N—N=CH$_2$—, $L^1$ represents an alkylene group of 1 to 8 carbon atoms, the alkylene group may be branched and may be substituted with a halogen atom or a cyano group, and the alkylene group represented by $L^1$ may be interrupted by —O—, —CH=CH—, or —C≡C—, $Y^1$, $Y^2$, $Y^3$, and $Y^4$ each independently represent an alkyl group of 1 to 6 carbon atoms, a halogen atom, or a cyano group, a hydrogen atom of the alkyl group represented by each of $Y^1$, $Y^2$, $Y^3$ and $Y^4$ may be substituted with a halogen atom or a cyano group, and a methylene chain in the alkyl group represented by each of $Y^1$, $Y^2$, $Y^3$ and $Y^4$ may be interrupted by —O— or —CO—, a, b, c, and d are each independently from 0 to 8, and f, g, and h are each independently 0 or 1, j and k are each independently 0, 1, or 2, provided that j+k≥2, and $G^1$ and $G^2$ each independently represent a substituent selected from the group consisting of substituents represented by formulae (1) to (4):

[Chemical Formula 9]

(1)

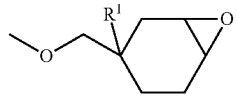

(2)

(3)

-continued (4)

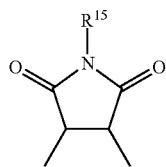

wherein in formula (1), $M^1$ represents a hydrogen atom, a methyl group, or a halogen atom; in formula (2), $R^1$ represents a hydrogen atom or an alkyl group of 1 to 6 carbon atoms; in formula (3), $R^2$ represents a hydrogen atom or an alkyl group of 1 to 6 carbon atoms; and in formula (4), $R^3$ represents a hydrogen atom or an alkyl group of 1 to 6 carbon atoms.

In formula (I), the optically active linking group represented by each of rings $A^1$, $A^2$, $A^3$, and $A^4$ is preferably the linking group of each chiral agent for TN or STN or each chiral agent described in Liquid Crystal Device Handbook, Chapter 3, Section 4-3 or page 200, 201, or 202, or is preferably a linking group represented by each of formulae (15) to (21) below:

[Chemical Formula 10]

(15)

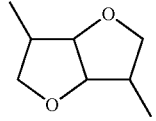

(16)

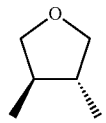

(17)

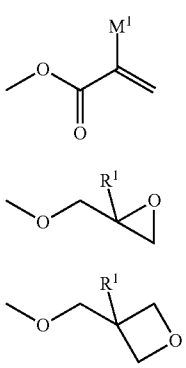

(18)

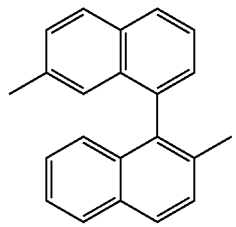

-continued

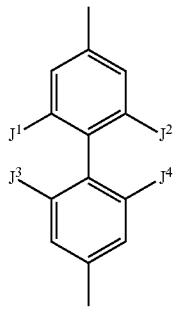
(19)

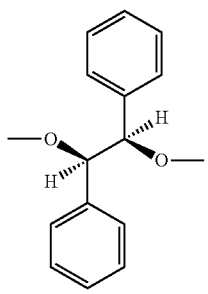
(20)

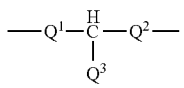
(21)

wherein in formula (15), $R^{15}$ represents an alkyl group of 1 to 10 carbon atoms, an aryl group of 6 to 20 carbon atoms, or an arylalkyl group of 7 to 20 carbon atoms, a hydrogen atom in $R^{15}$ may be substituted with a halogen atom, and a methylene chain in $R^{15}$ may be interrupted by —O—, —COO—, or —OCO—. In formula (19), $J^1$ to $J^4$ each independently represent an alkyl group of 1 to 6 carbon atoms, an alkoxy group of 1 to 6 carbon atoms, a halogen atom, —COOR', —OCOR', —OCOOR', —CONHR', or —NHCOR', wherein R' represents a hydrogen atom or an alkyl group of 1 to 6 carbon atoms. In formula (21), $Q^1$ and $Q^2$ each independently represent a direct bond, an alkylene group of 1 to 10 carbon atoms, or an alkylene-oxy group of 1 to 10 carbon atoms, and $Q^3$ represents a halogen atom, a cyano group, an alkyl group of 1 to 4 carbon atoms, or an alkoxy group of 1 to 4 carbon atoms.

In formula (I), the alkylene group of 1 to 8 carbon atoms represented by each of $S^1$ and $S^2$ may be ethylene, propylene, trimethylene, tetramethylene, butane-1,3-diyl, 2-methylpropane-1,3-diyl, 2-methylbutane-1,3-diyl, pentane-2,4-diyl, pentane-1,4-diyl, 3-methylbutane-1,4-diyl, 2-methylpentane-1,4-diyl, pentamethylene, hexamethylene, heptamethylene, octamethylene, nonamethylene, decamethylene, or any other alkylene group.

The alkylene group may be substituted with a halogen atom or may be branched. A methylene chain in the alkylene group may be interrupted by —O—. There is no restriction to the position and number of halogen atom substituents, the position and number of the branched moieties, or the position and number of the interrupting —O— moieties in the alkylene group.

In formula (I), $L^1$ represents an alkylene group of 1 to 8 carbon atoms, the alkylene group may be branched and may be substituted with a halogen atom or a cyano group. Examples of the alkylene group represented by $L^1$ include those of the alkylene group of 1 to 8 carbon atoms listed above for $S^1$ and $S^2$ in formula (I).

There is no restriction to the position and number of halogen atom or cyano group substituents or the position or number of the branched moieties in the alkylene group. A methylene chain in the alkylene group may be interrupted by —O—, —CH═CH—, or —C≡C—. There is no restriction to the position or number of the interrupting —O—, —CH═CH—, or —C≡C— moieties in the alkylene group.

In formula (I), the alkyl group of 1 to 6 carbon atoms represented by each of $Y^1$, $Y^2$, $Y^3$, and $Y^4$ may be methyl, chloromethyl, trifluoromethyl, cyanomethyl, ethyl, dichloroethyl, propyl, isopropyl, cyclopropyl, butyl, sec-butyl, tert-butyl, isobutyl, amyl, isoamyl, tert-amyl, cyclopentyl, hexyl, 2-methylpentyl, 3-methylpentyl, cyclohexyl, bicyclohexyl, 1-methylcyclohexyl, or the like.

A hydrogen atom of the alkyl group may be substituted with a halogen atom or a cyano group. A methylene chain in the alkyl group may be interrupted by —O— or —CO—. There is no restriction to the position and number of halogen atom or cyano group substituents or the position and number of the interrupting —O— or —CO— moieties in the alkyl group.

In each of $Y^1$, $Y^2$, $Y^3$, and $Y^4$, the halogen atom may be fluorine, chlorine, bromine, iodine, or the like.

Examples of the halogen atom represented by $M^1$ in formula (1) and examples of the alkyl group of 1 to 6 carbon atoms represented by $R^1$ in formula (2), $R^2$ in formula (3), and $R^3$ in formula (4) include those listed above for $Y^1$, $Y^2$, $Y^3$, and $Y^4$ in formula (I).

Among the polymerizable liquid crystal compounds represented by formula (I), compounds having benzene rings or naphthalene rings as rings $A^1$, $A^2$, $A^3$, and $A^4$ are preferred in that they have low crystallinity and can show a liquid crystal phase at 25° C. or lower and emit linearly polarized light. Among the polymerizable liquid crystal compounds represented by formula (I), compounds in which at least one of rings $A^1$, $A^2$, $A^3$, and $A^4$ has a certain content of an optically active linking group are preferred in that they can emit circularly polarized light.

Compounds represented by formula (I) in which both $G^1$ and $G^2$ are substituents represented by formula (1) are preferred because they are rapidly curable by UV irradiation in the air.

Compounds represented by formula (I) in which $Z^1$, $Z^2$, $Z^3$, $Z^4$, and $Z^5$ are each —CO—O— or —OCO— are preferred because they have a higher level of liquid crystal orientation properties.

Among the compounds represented by formula (I), compounds represented by formula (II) below are preferred because they show a liquid crystal phase in a wide temperature range, have low crystallinity, and have high liquid-crystal-phase stability in a low temperature region.

[Chemical Formula 11]

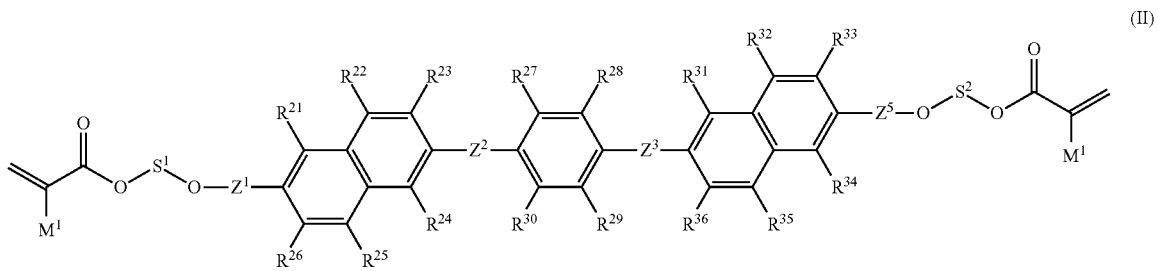

(II)

In the formula, $S^1$, $S^2$, $M^1$, $Z^1$, $Z^2$, $Z^3$, and $Z^5$ are the same as defined in formula (I), $R^{21}$ to $R^{36}$ each independently represent an alkyl group of 1 to 6 carbon atoms, a halogen atom, or a cyano group, a hydrogen atom of the alkyl group represented by each of $R^{21}$ to $R^{36}$ may be substituted with a halogen atom or a cyano group, and a methylene chain in the alkyl group represented by each of $R^{21}$ to $R^{36}$ may be interrupted by —O— or —CO—.

Examples of the alkyl group of 1 to 6 carbon atoms represented by each of $R^{21}$ to $R^{36}$ in formula (II) include those of the alkyl group of 1 to 6 carbon atoms listed above for $Y^1$, $Y^2$, $Y^3$, and $Y^4$ in formula (I).

Among the compounds represented by formula (I), compounds represented by formula (III) below are preferred because they show a liquid crystal phase in a wide temperature range, have low crystallinity, and have high liquid-crystal-phase stability in a low temperature region.

Examples of the alkyl group of 1 to 6 carbon atoms represented by each of $R^{41}$ to $R^{52}$ in formula (III) include those of the alkyl group of 1 to 6 carbon atoms listed above for $Y^1$, $Y^2$, $Y^3$, and $Y^4$ in formula (I).

The polymerizable liquid crystal compound (A) may have optical activity (such as A-124 to A-132 shown below). The polymerizable liquid crystal compound (A) having optical activity may be used in combination with a non-optically active polymerizable liquid crystal compound to form a macromolecule having an inner spiral structure of liquid crystal skeleton.

In this case, the content of the optically active compound is preferably from 0.1 to 10 parts by weight, more preferably from 1 to 5 parts by weight. If the content of the optically active compound is less than 0.1 parts by weight, the desired pitch length (reflection characteristics) may fail to be

[Chemical Formula 12]

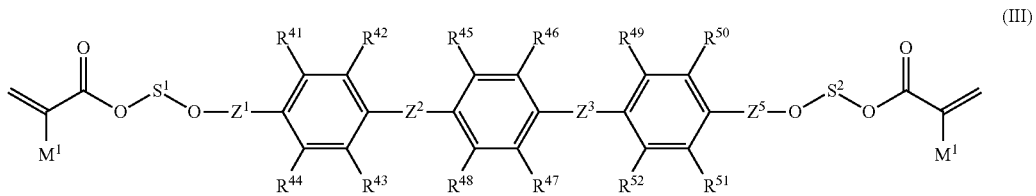

(III)

In the formula, $S^1$, $S^2$, $M^1$, $Z^1$, $Z^2$, $Z^3$, and $Z^5$ are the same as defined in formula (I), $R^{41}$ to $R^{52}$ each independently represent an alkyl group of 1 to 6 carbon atoms, a halogen atom, or a cyano group, a hydrogen atom of the alkyl group represented by each of $R^{41}$ to $R^{52}$ may be substituted with a halogen atom or a cyano group, and a methylene chain in the alkyl group represented by each of $R^{41}$ to $R^{52}$ may be interrupted by —O— or —CO—.

obtained, and if it is more than 10 parts by weight, the desired characteristics may fail to be obtained.

Examples of the polymerizable liquid crystal compound include the compounds listed in paragraphs [0172] to [0314] of JP-A No. 2005-15473, the compounds listed in paragraphs [0090] to [0093] of JP-A No. 2010-30974, the compounds listed in paragraph [0075] of JP-A No. 2010-105940, and other compounds such as compounds A-1 to A-134 shown below.

[Chemical Formula 13]
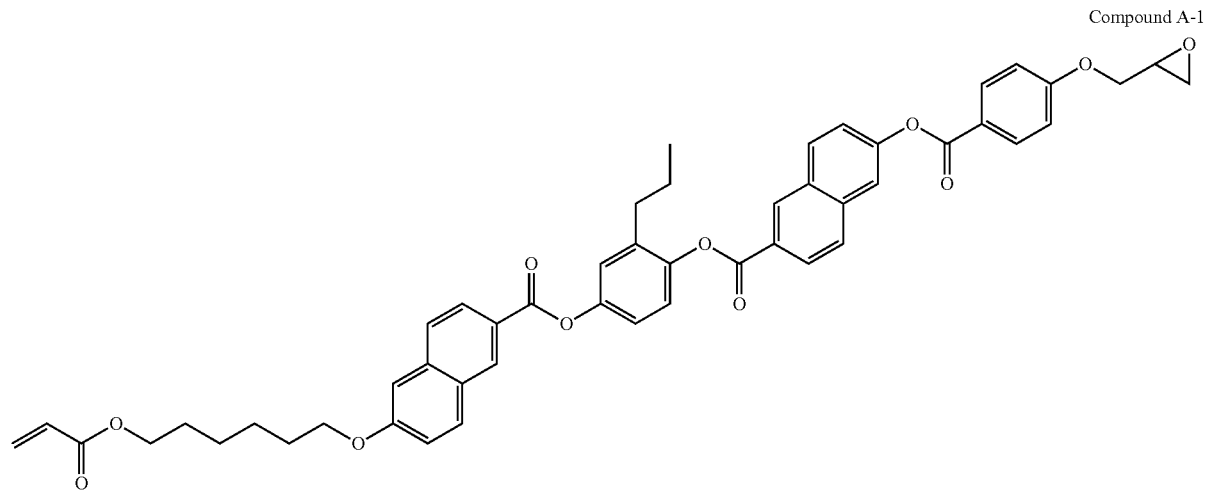
Compound A-1
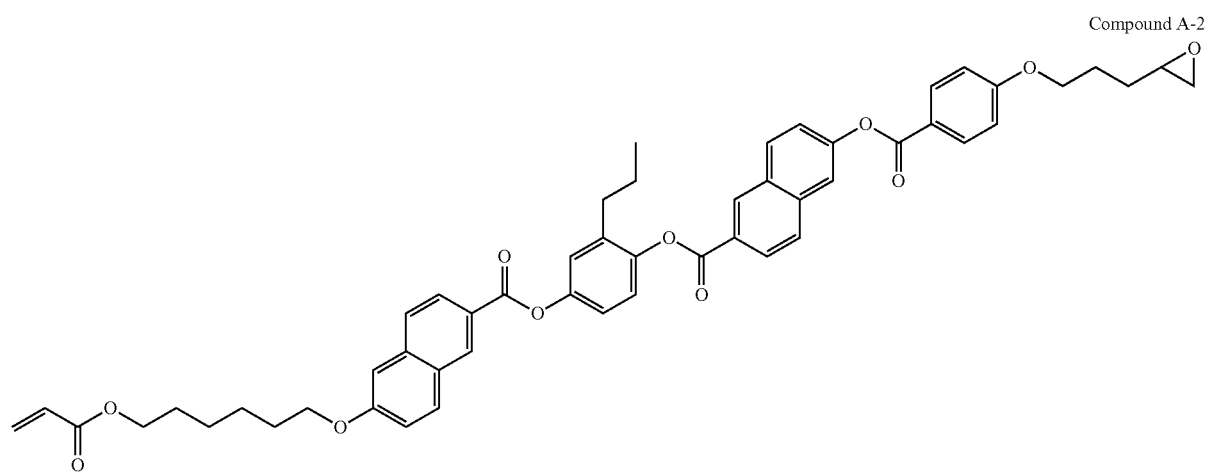
Compound A-2
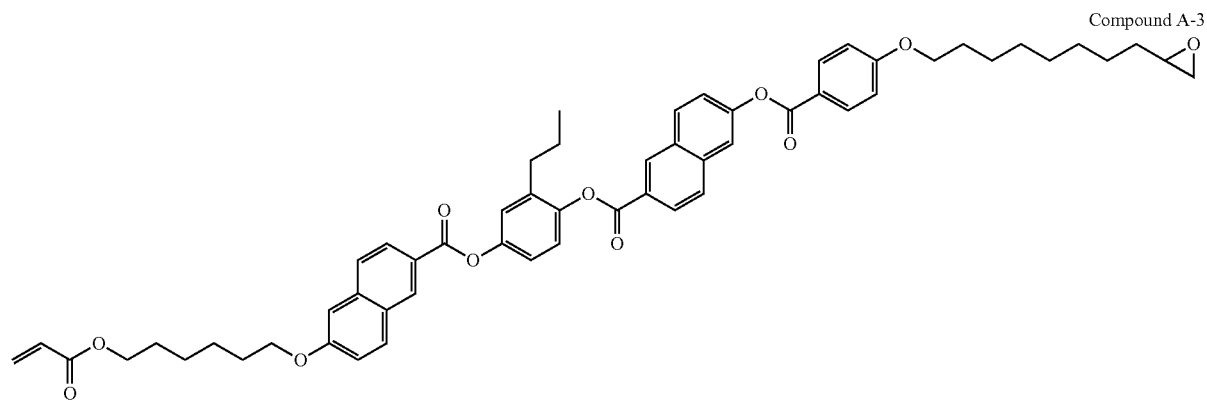
Compound A-3

-continued
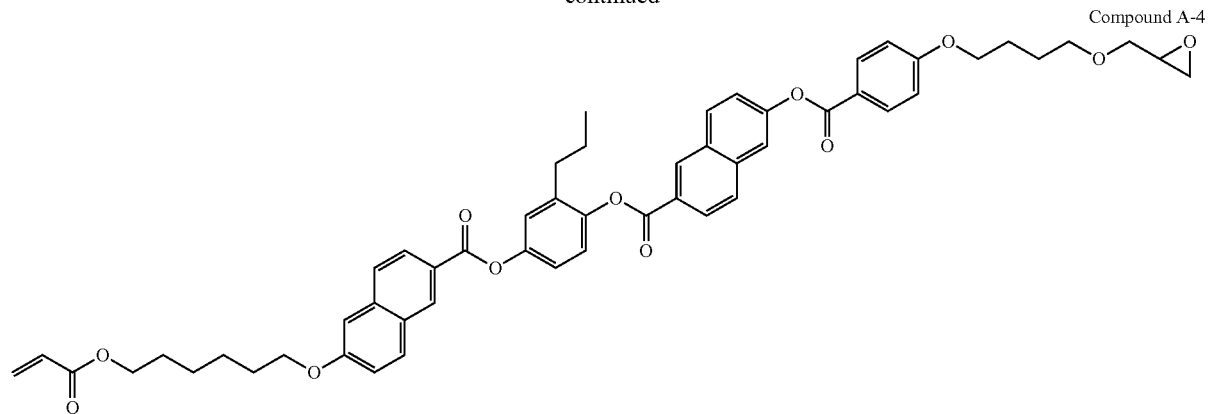
Compound A-4
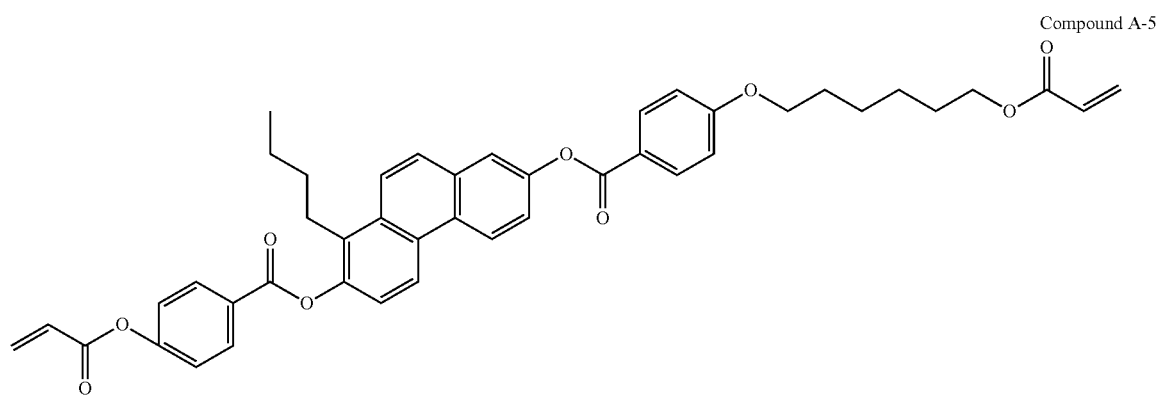
Compound A-5
[Chemical Formula 14]
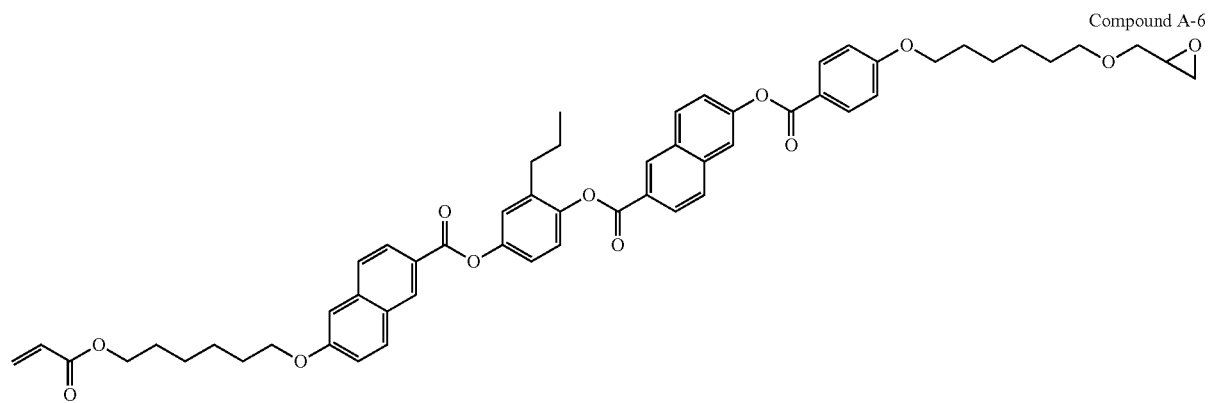
Compound A-6

-continued
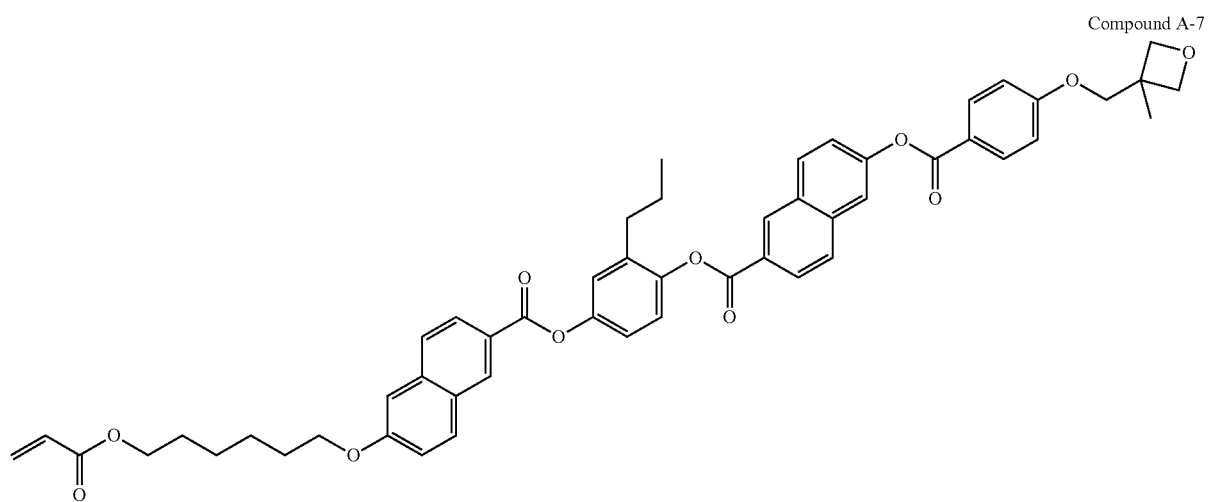
Compound A-7
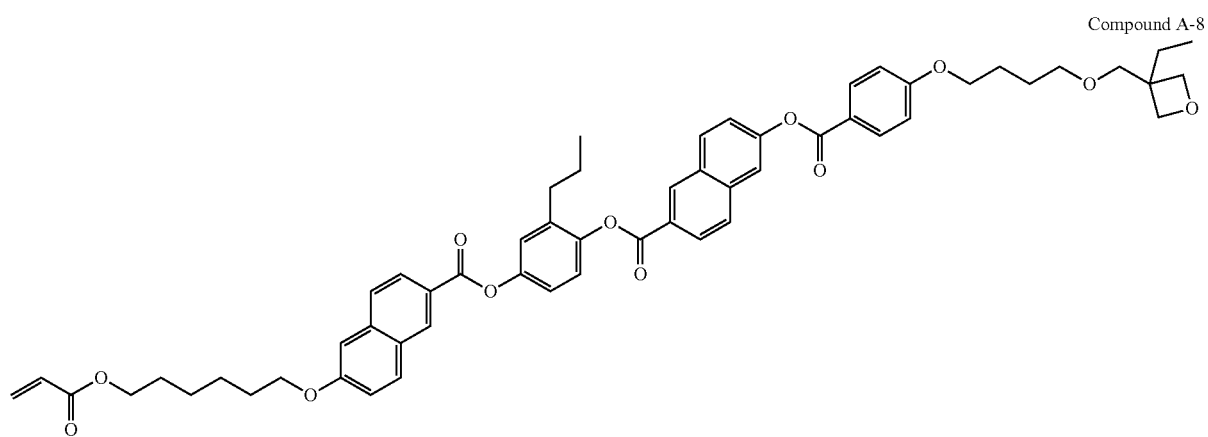
Compound A-8
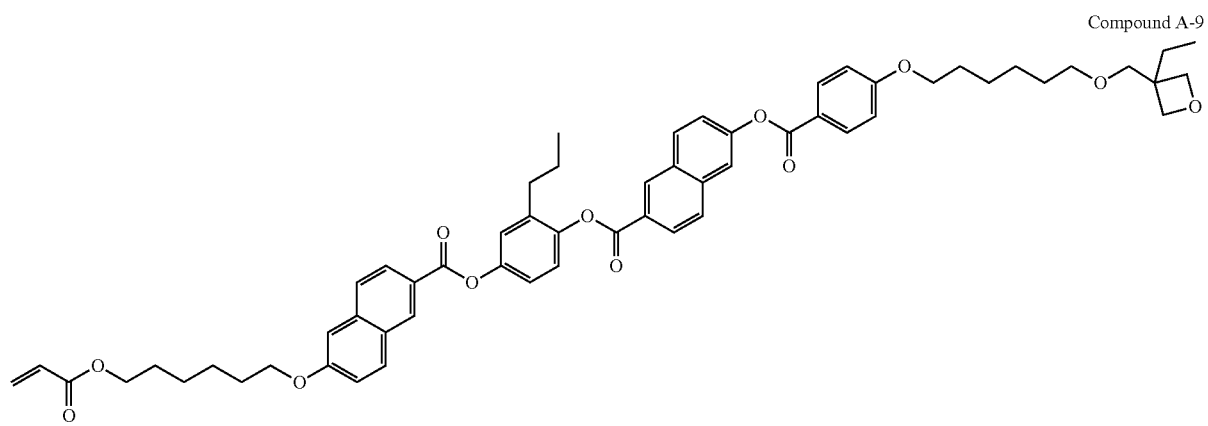
Compound A-9

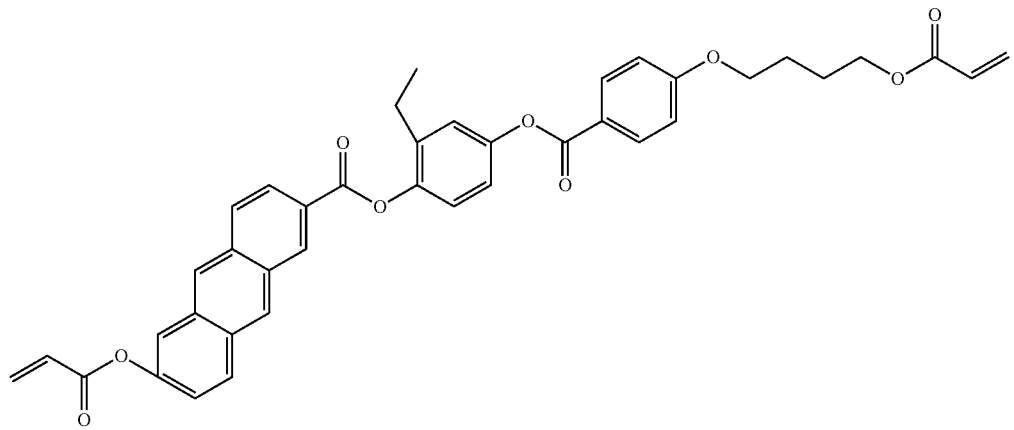
Compound A-10
[Chemical Formula 15]
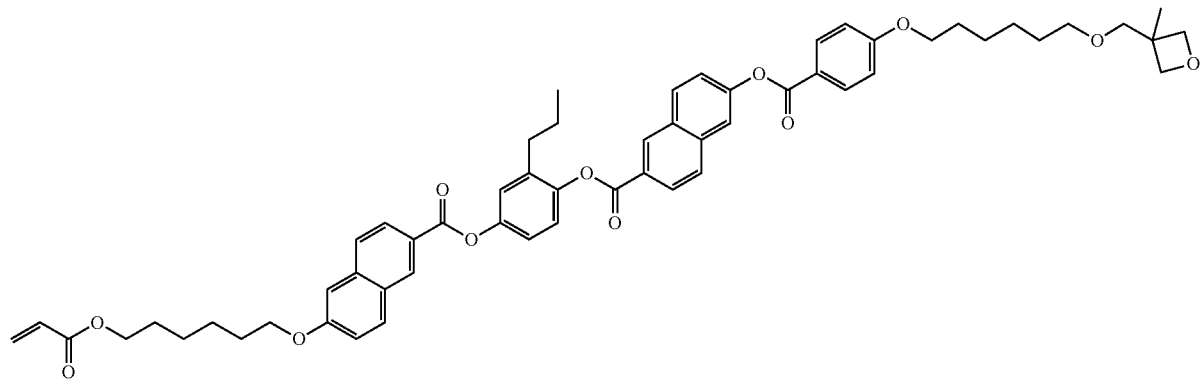
Compound A-11
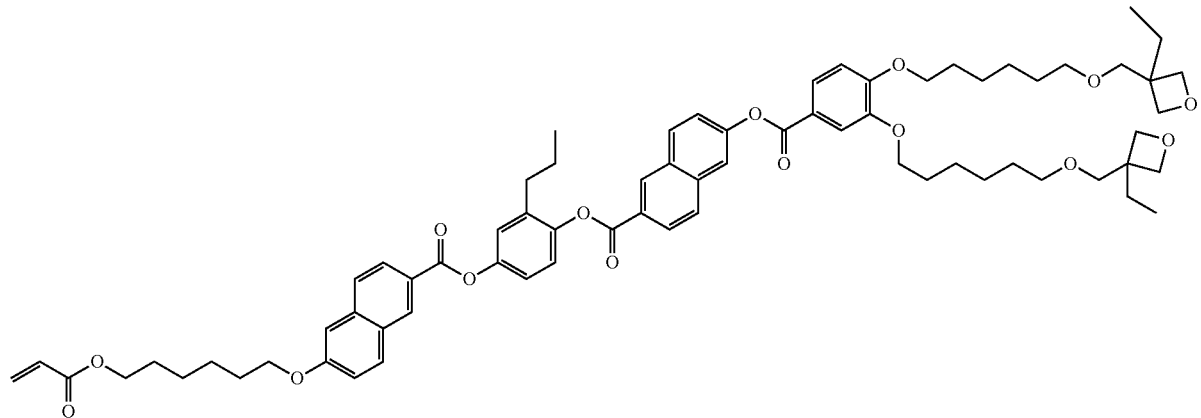
Compound A-12

-continued
Compound A-13
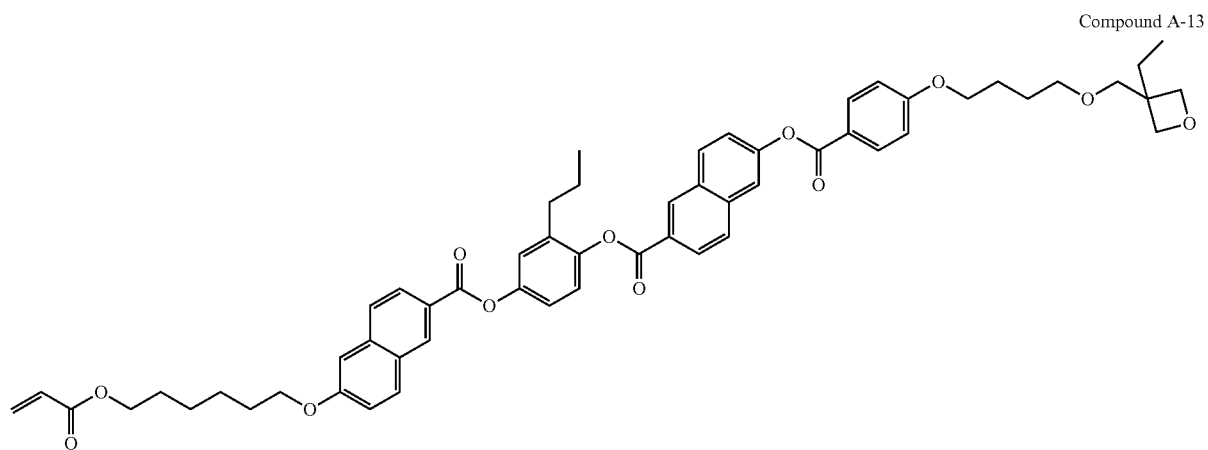
Compound A-14
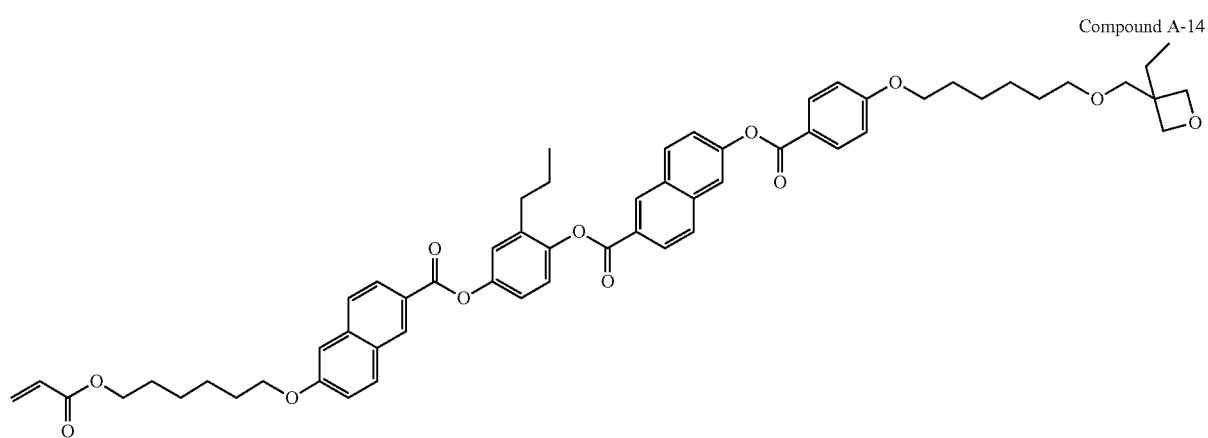
Compound A-15
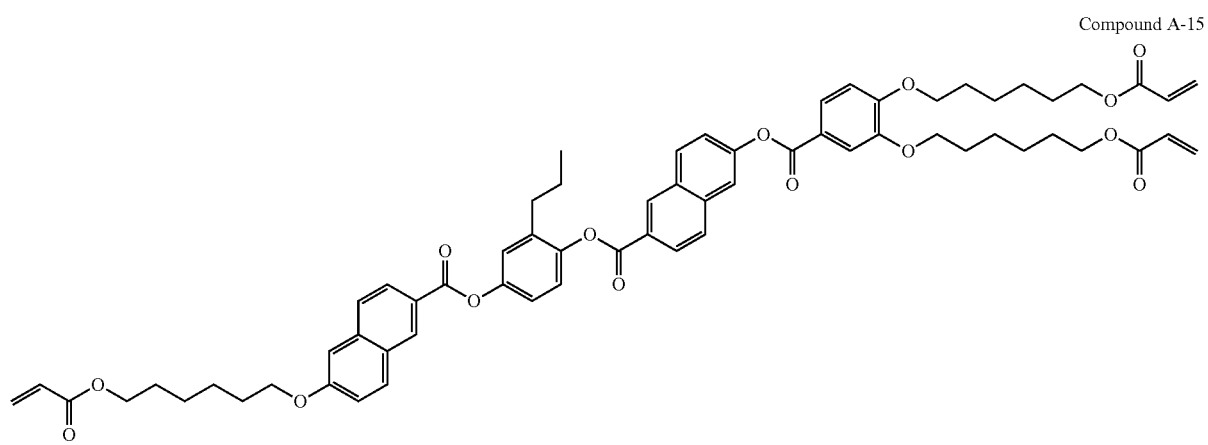

[Chemical Formula 16]
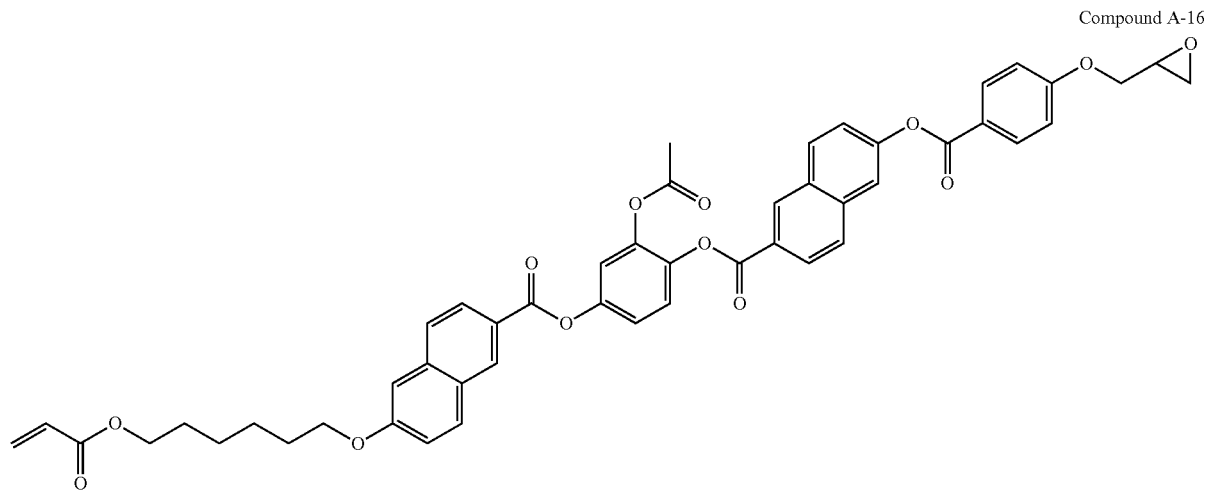
Compound A-16
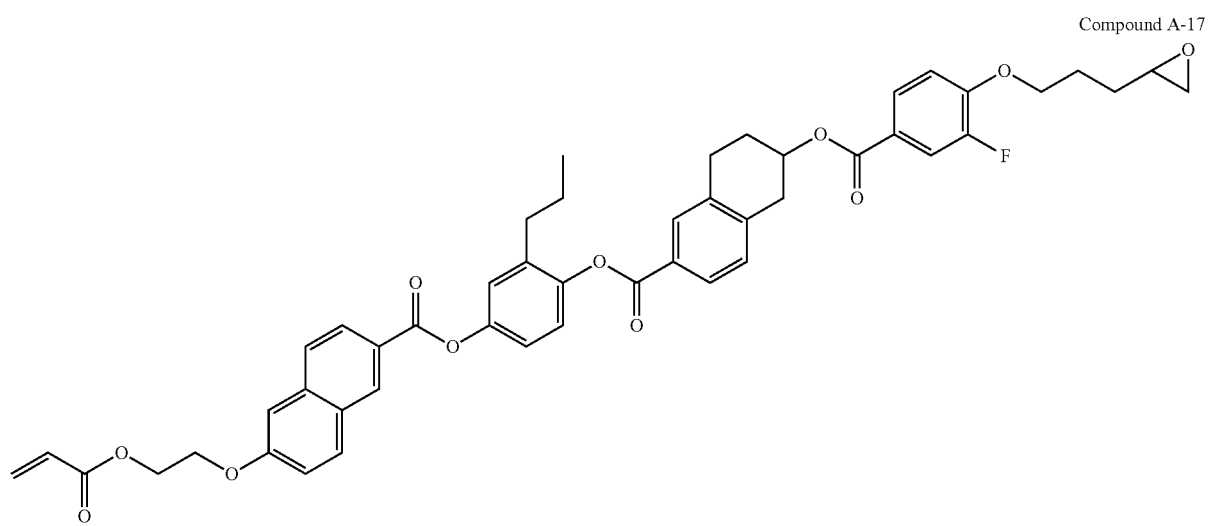
Compound A-17
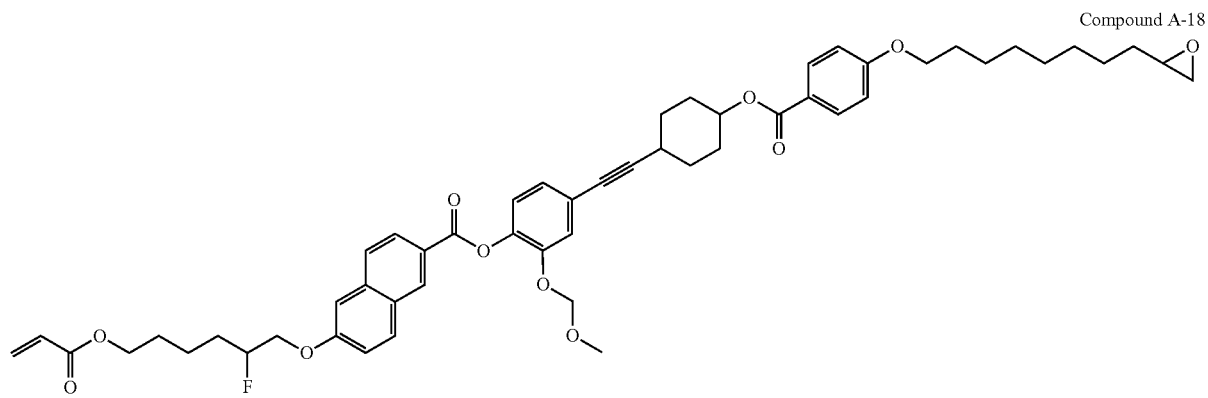
Compound A-18

-continued
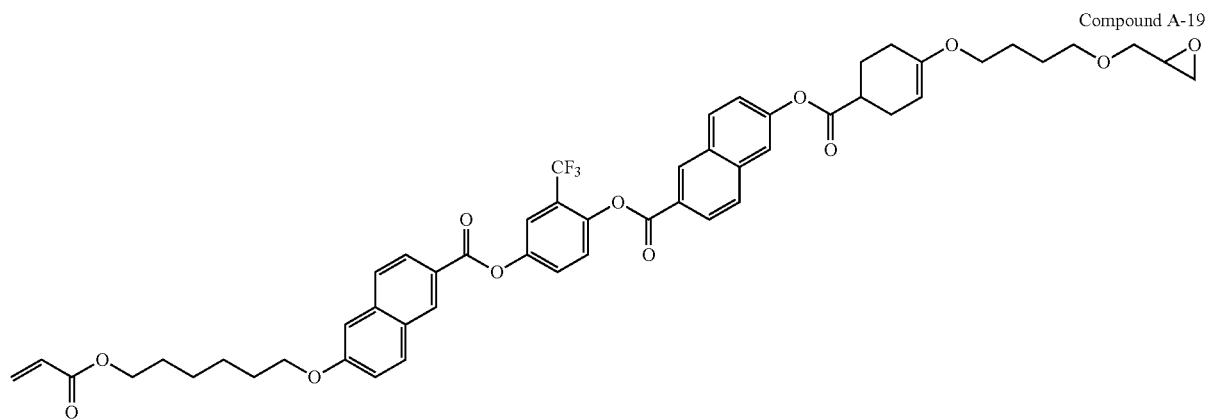
Compound A-19
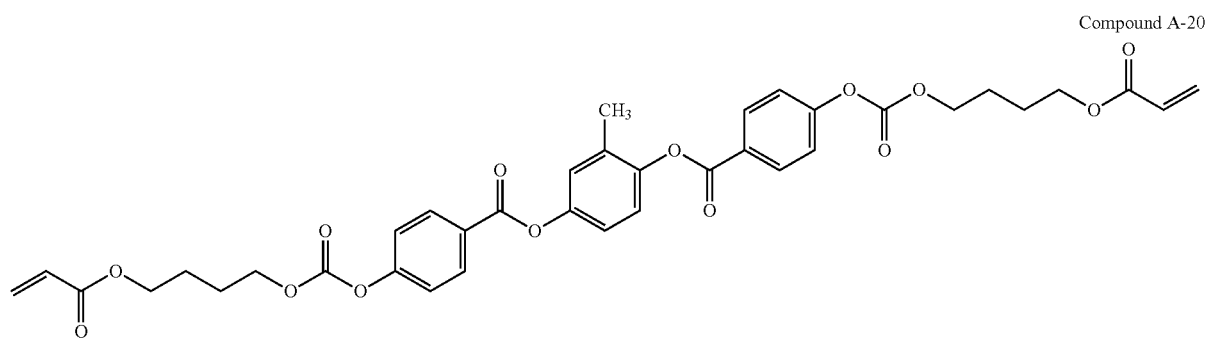
Compound A-20
[Chemical Formula 17]
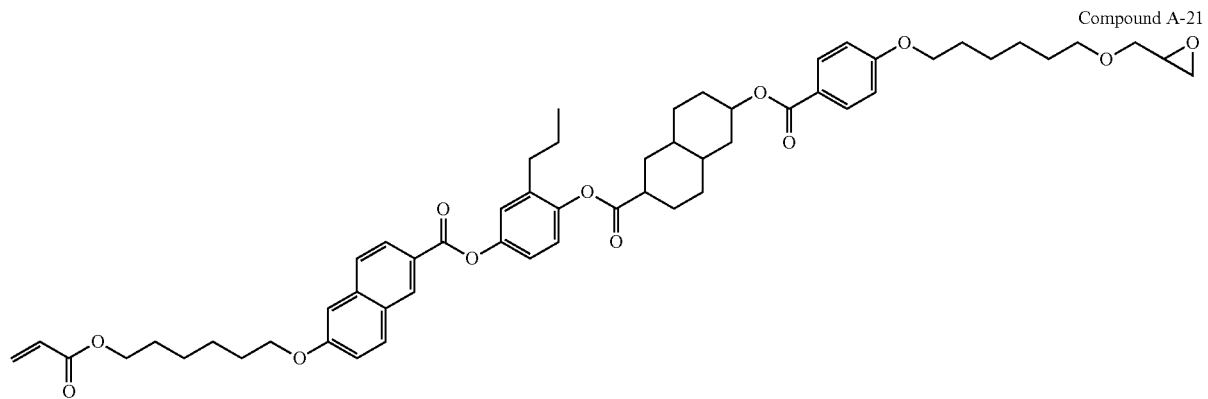
Compound A-21
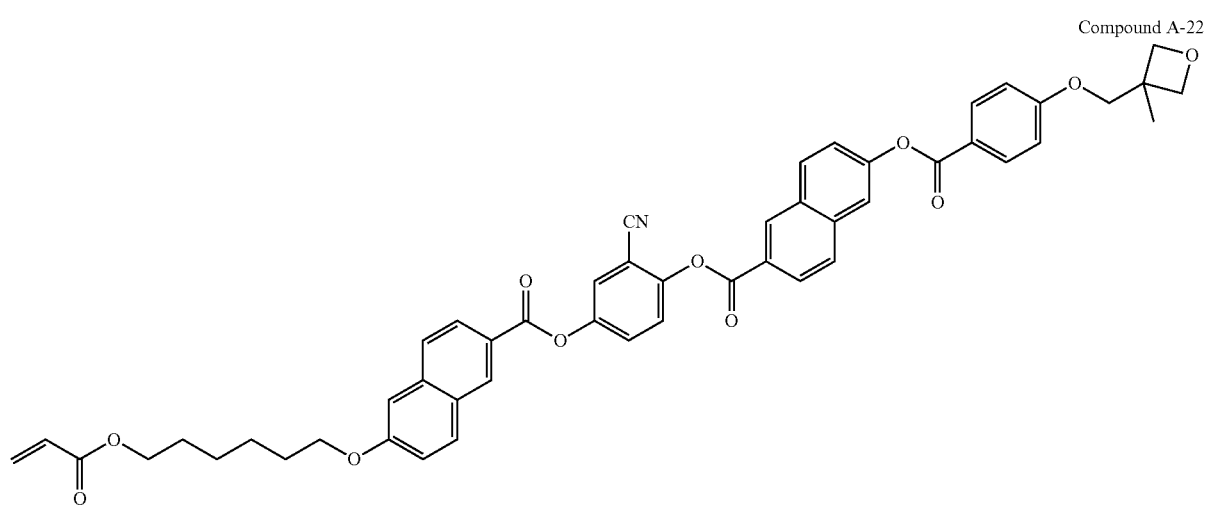
Compound A-22

Compound A-23
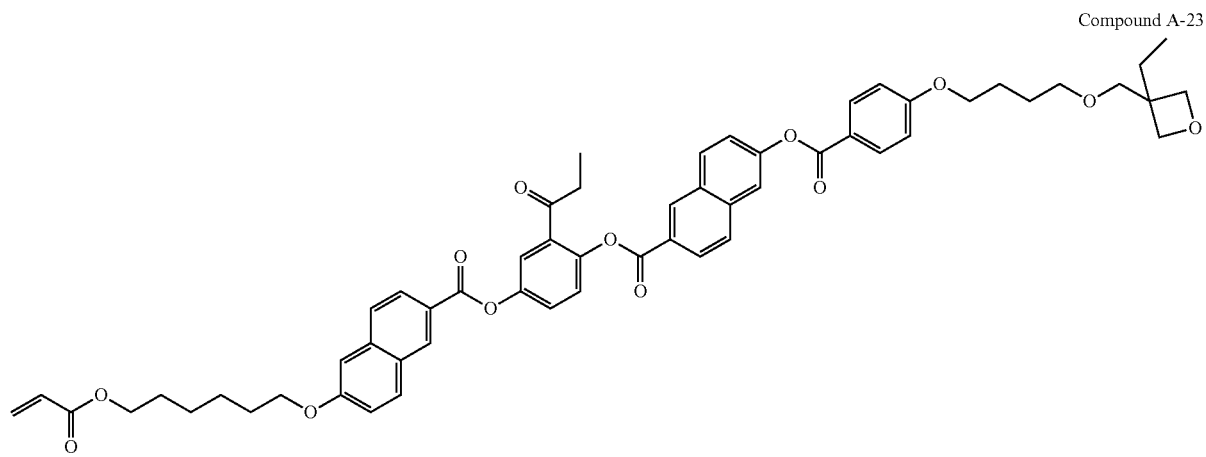
Compound A-24
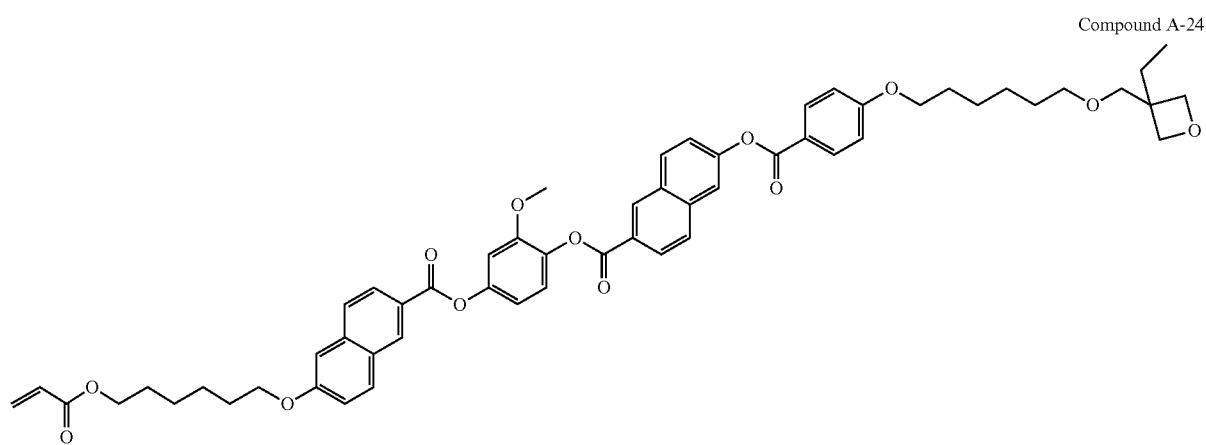
Compound A-25
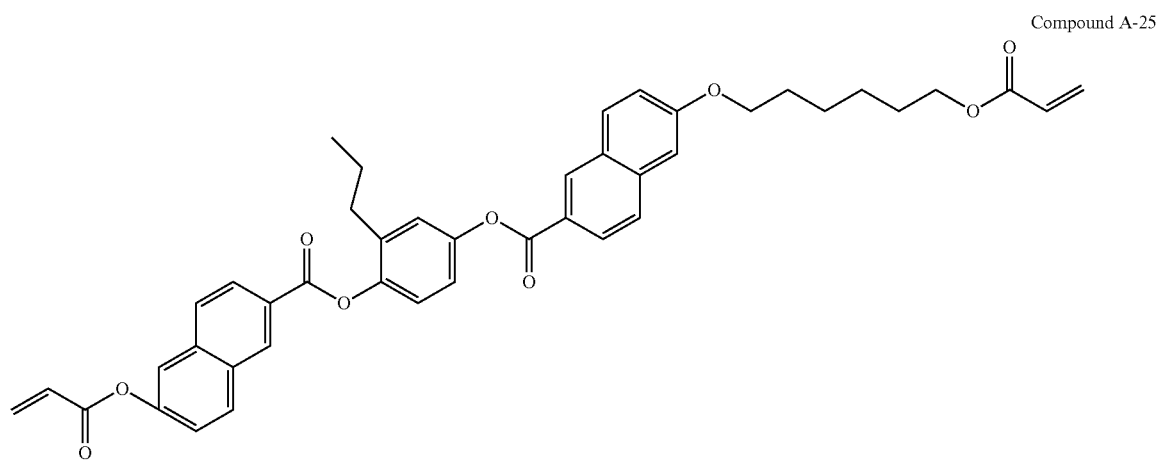

[Chemical Formula 18]
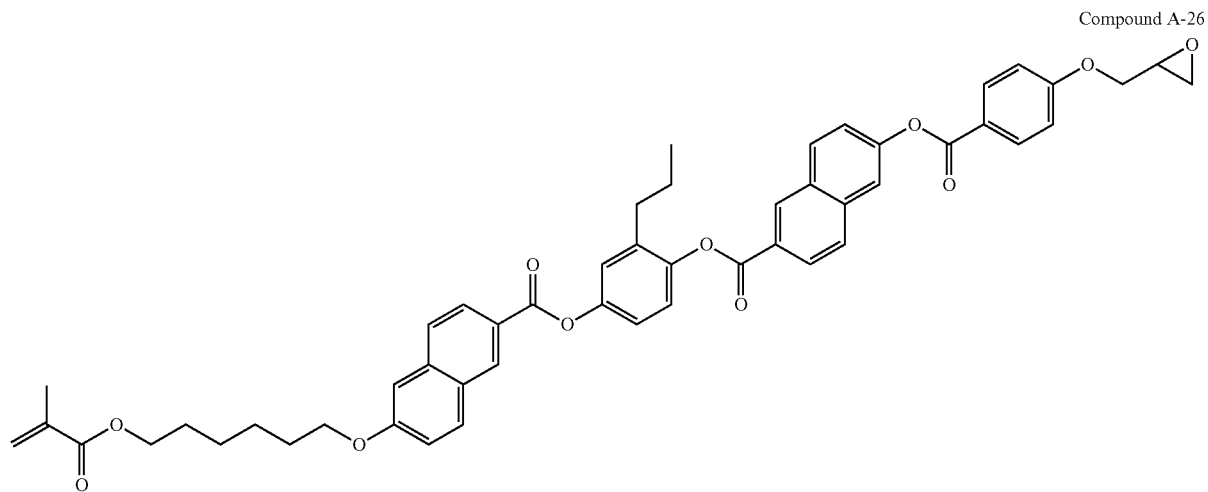
Compound A-26
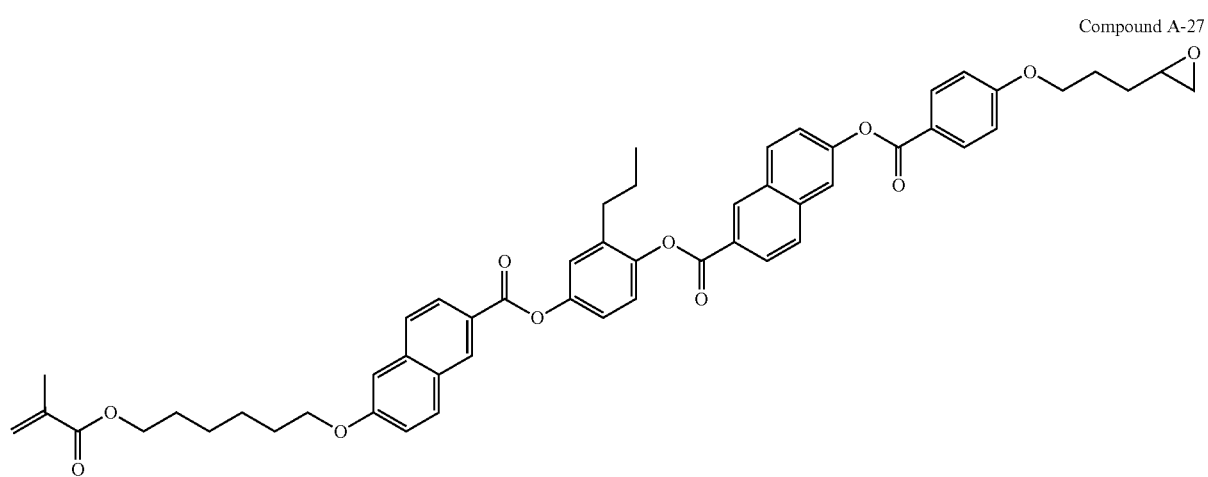
Compound A-27
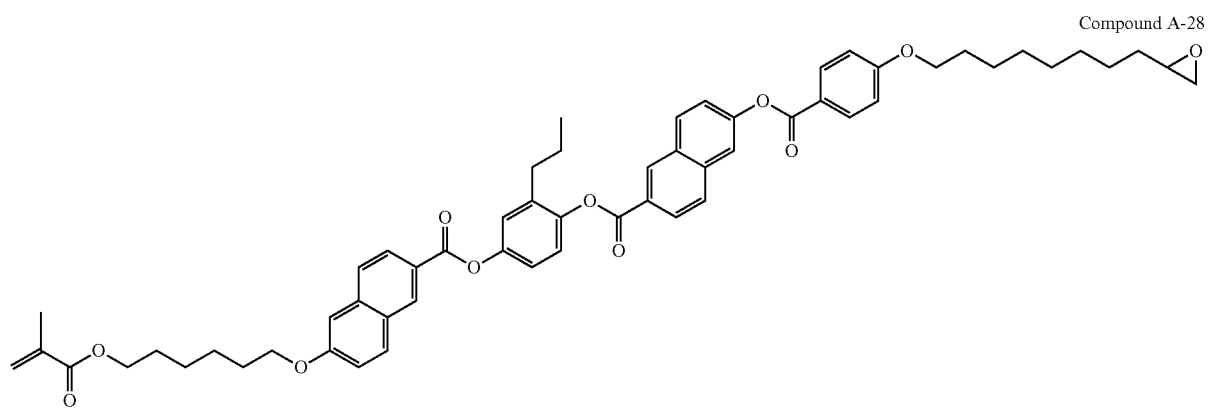
Compound A-28

-continued
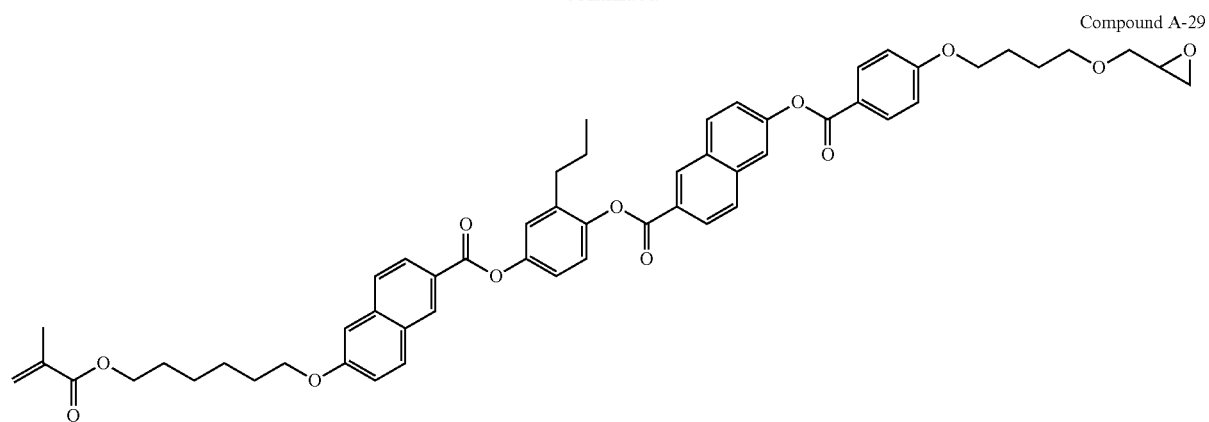
Compound A-29
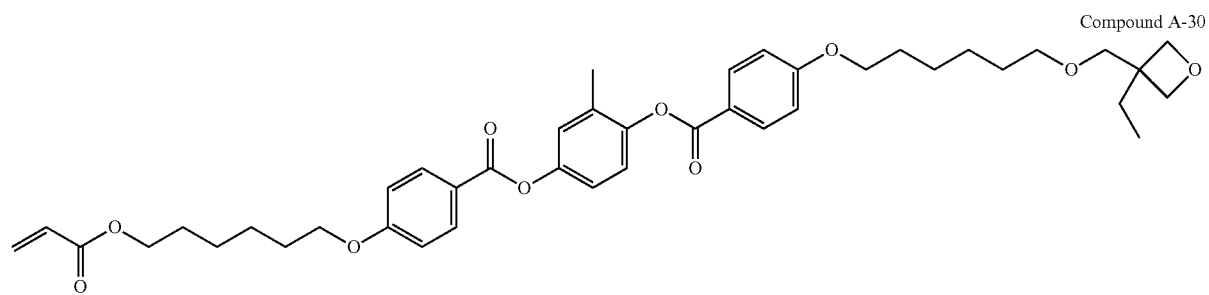
Compound A-30
[Chemical Formula 19]
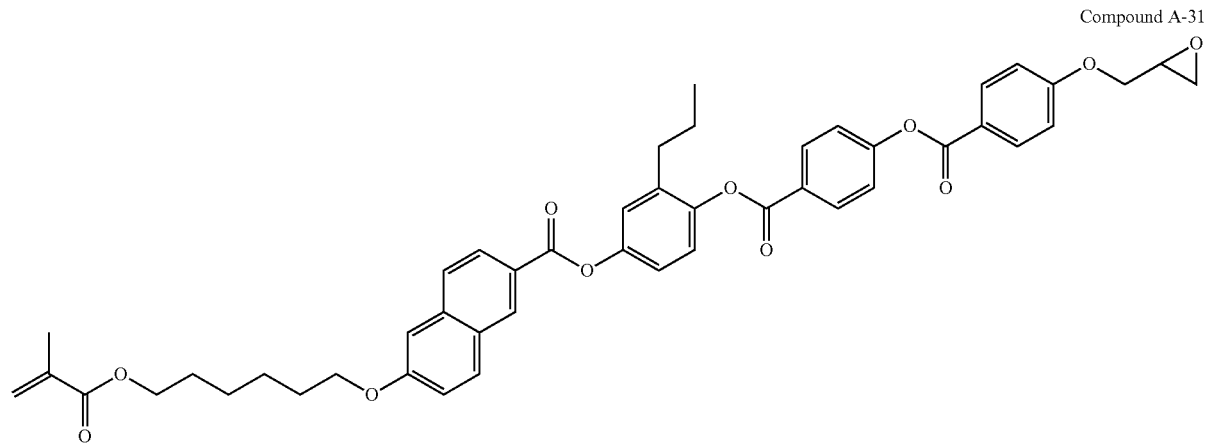
Compound A-31
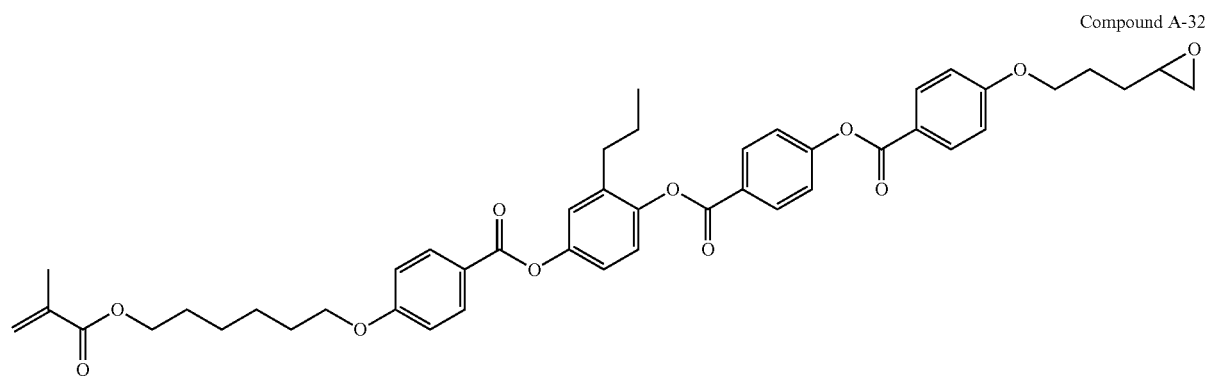
Compound A-32

Compound A-33
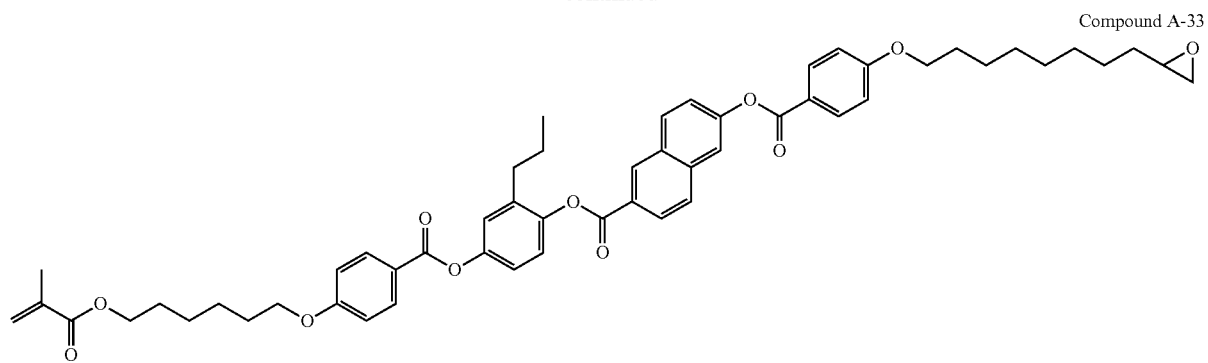
Compound A-34
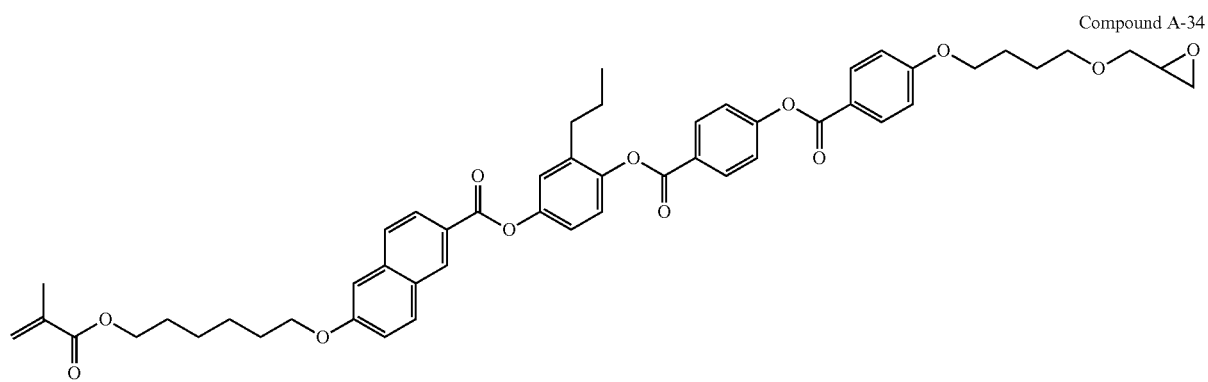
Compound A-35
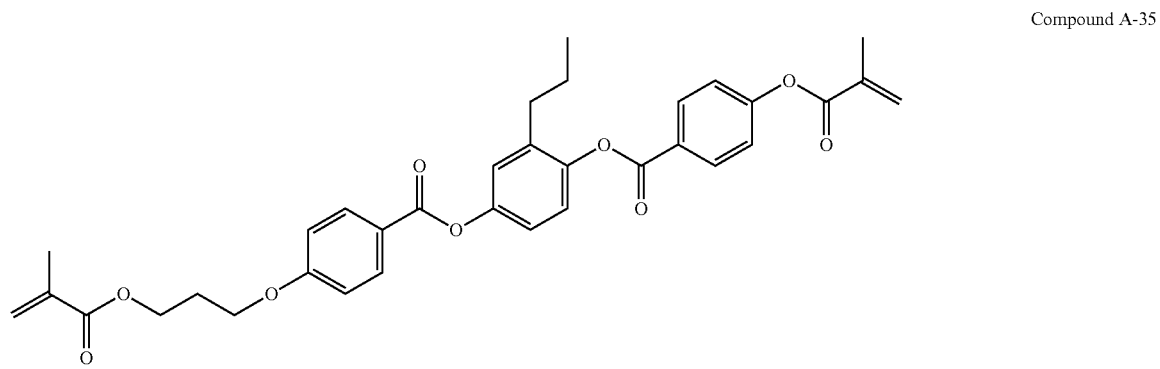
Compound A-36
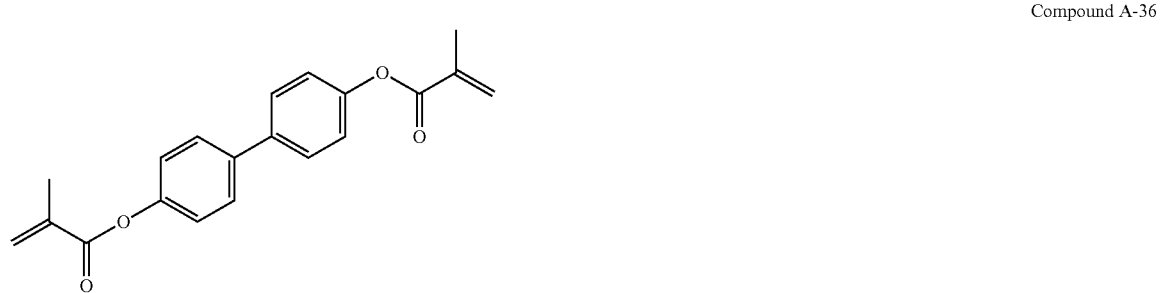

[Chemical Formula 20]
Compound A-37
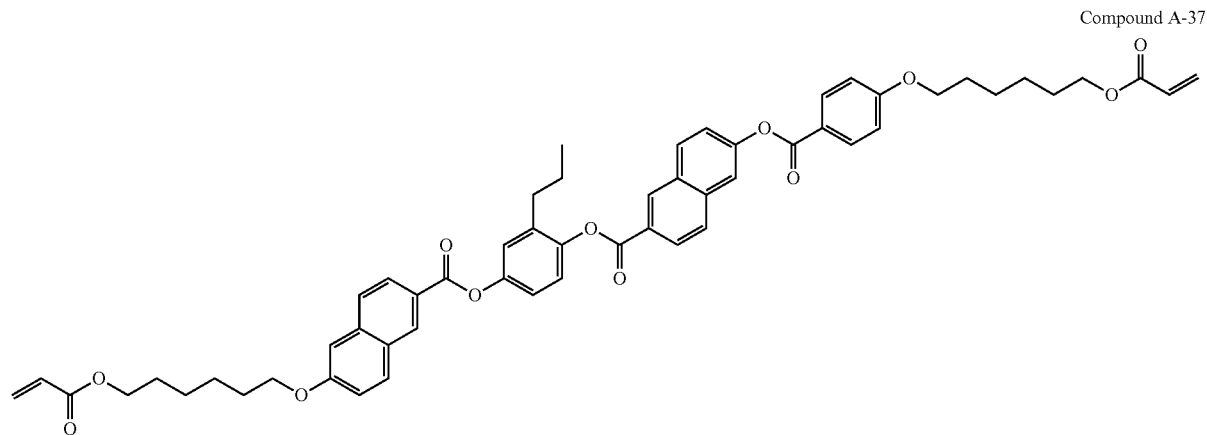
Compound A-38
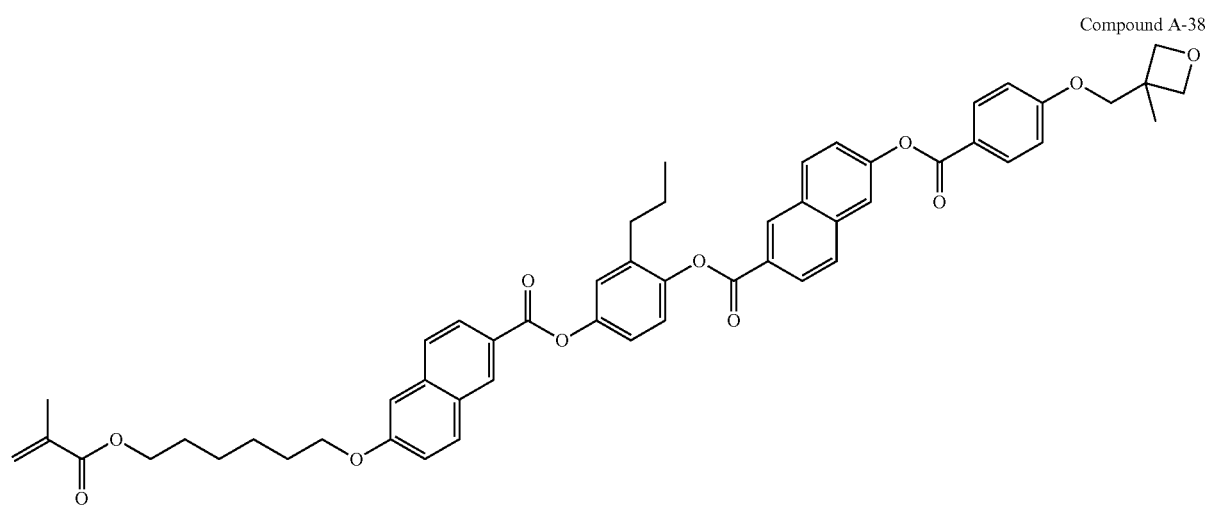
Compound A-39
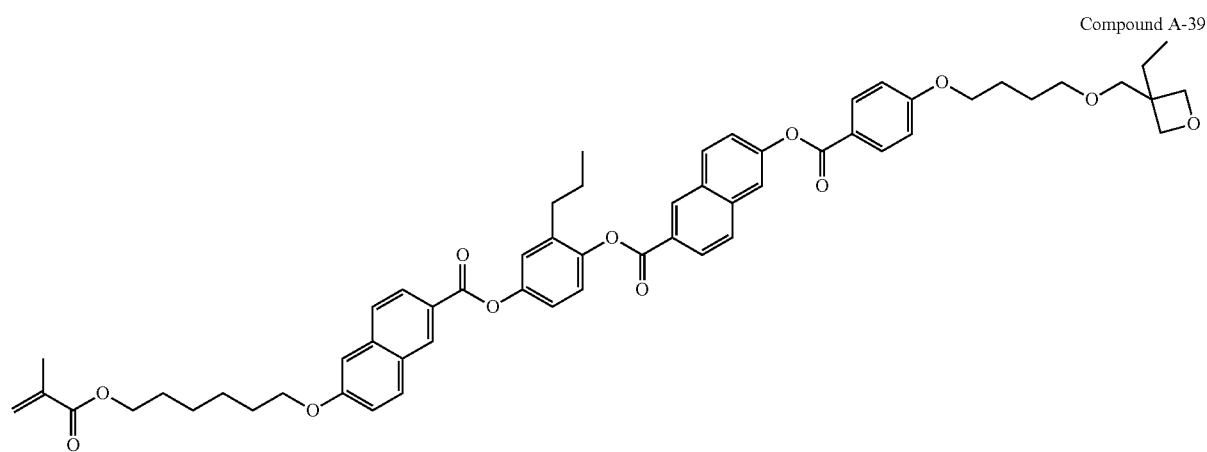

-continued
Compound A-40
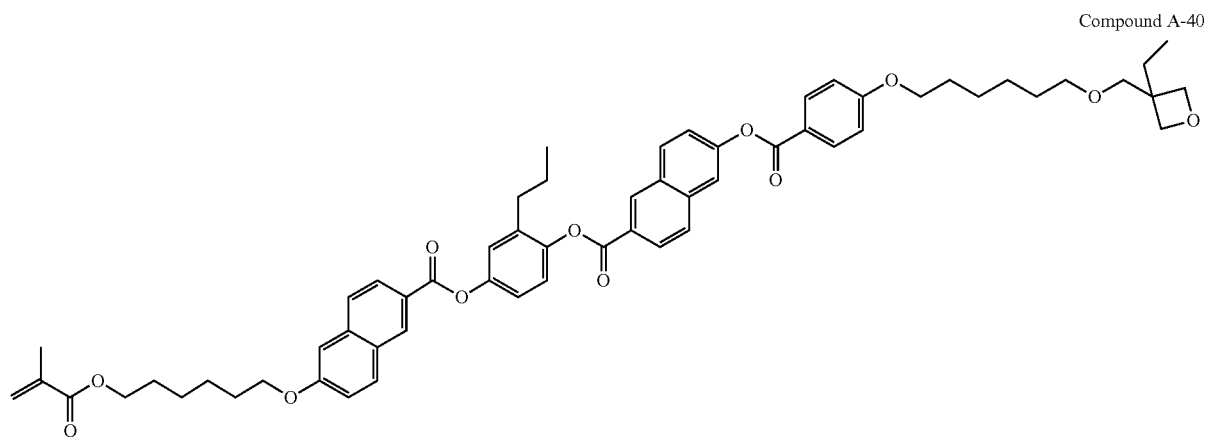
Compound A-41
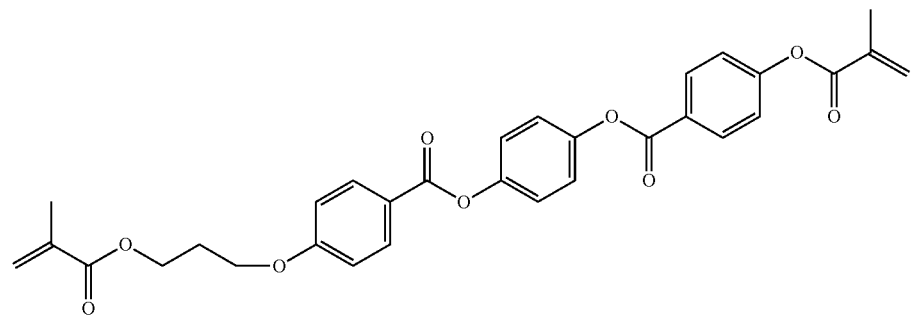
[Chemical Formula 21]
Compound A-42
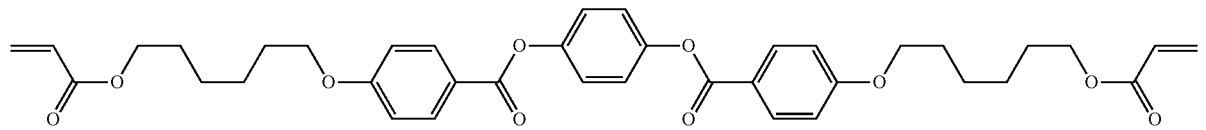
Compound A-43
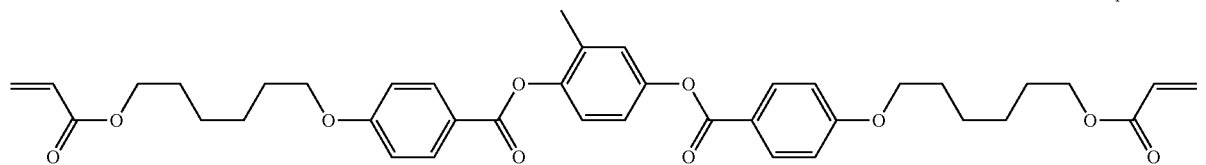
Compound A-44
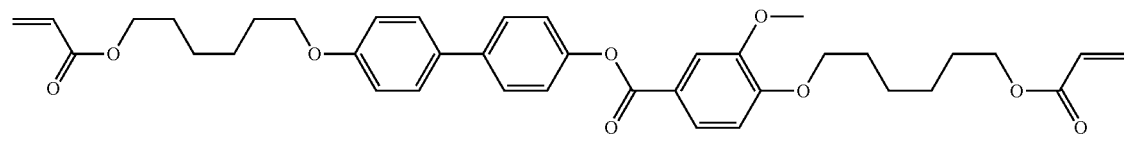
Compound A-45
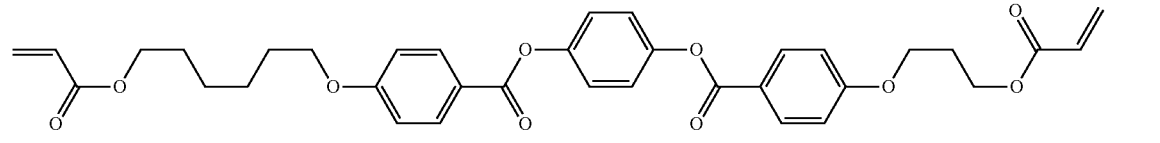
Compound A-46
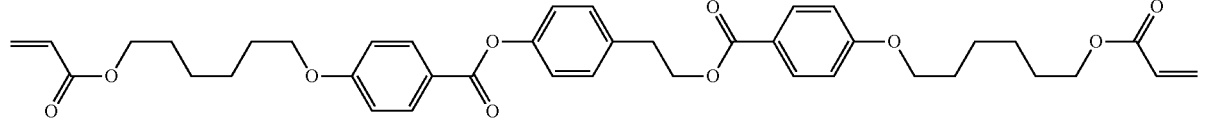

Compound A-47
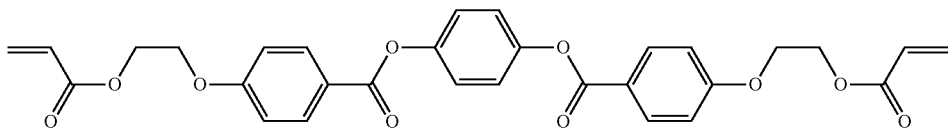
Compound A-48
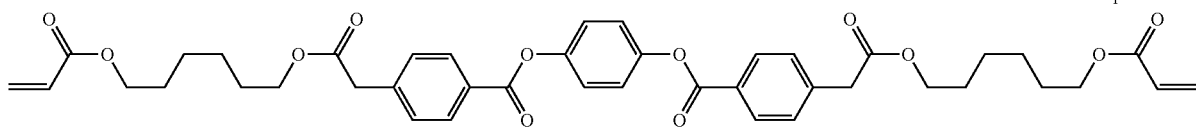
Compound A-49
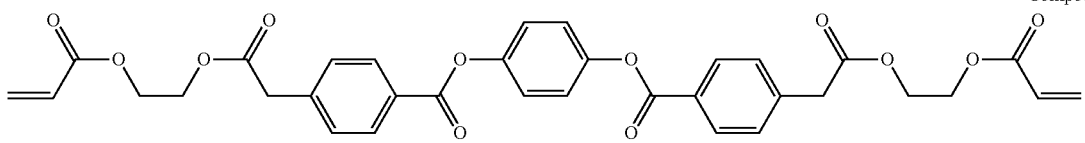
Compound A-50
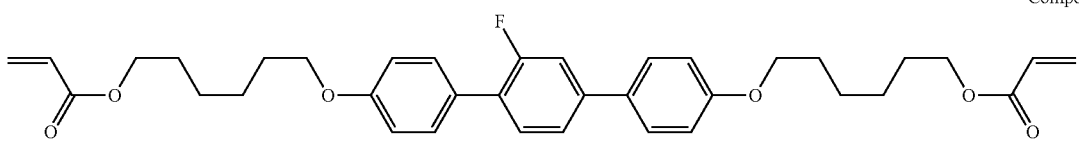
[Chemical Formula 22]
Compound A-51
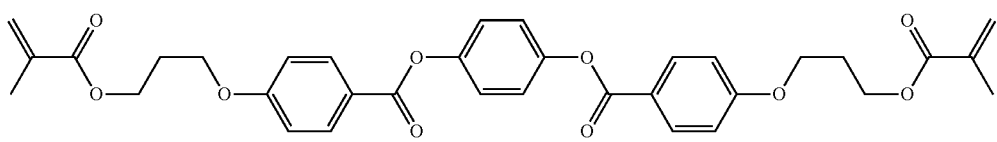
Compound A-52
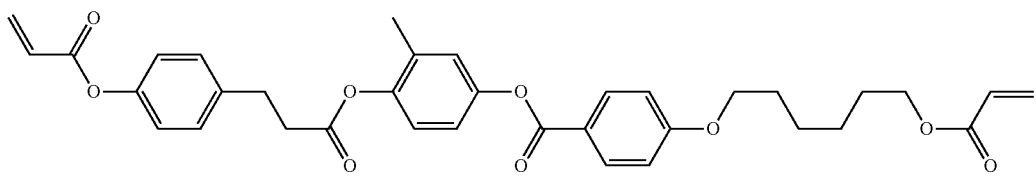
Compound A-53
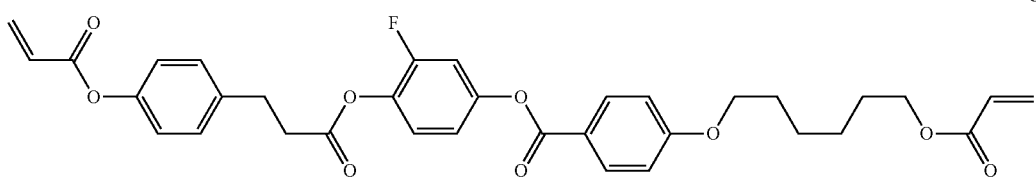
Compound A-54
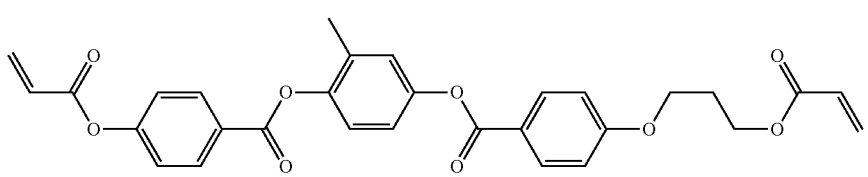
Compound A-55
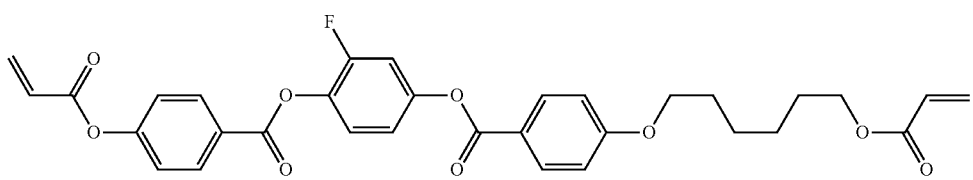

Compound A-56
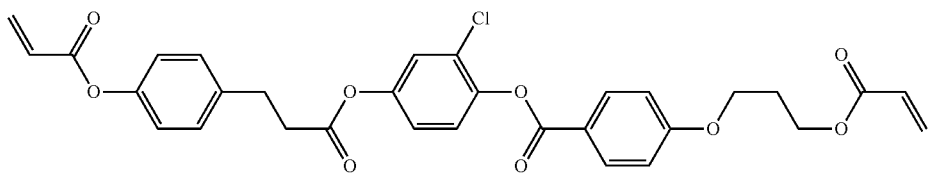
Compound A-57
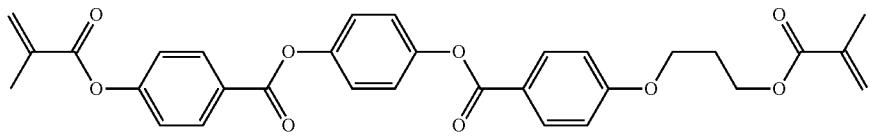
[Chemical Formula 23]
Compound A-58
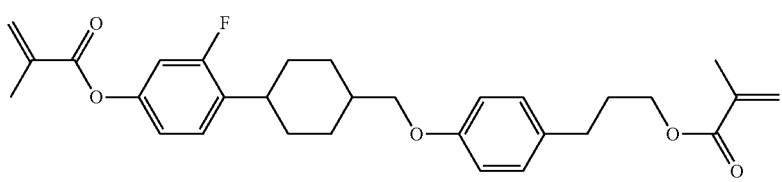
Compound A-59
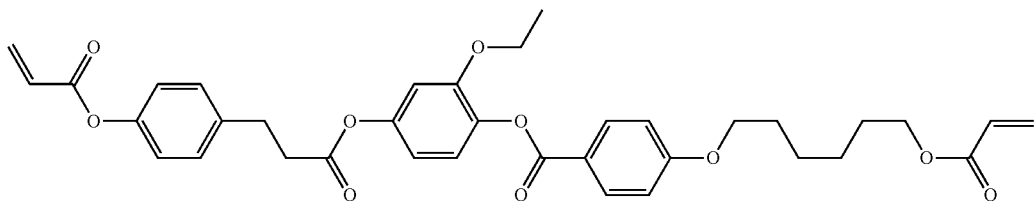
Compound A-60
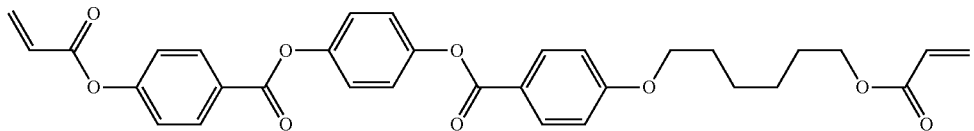
Compound A-61
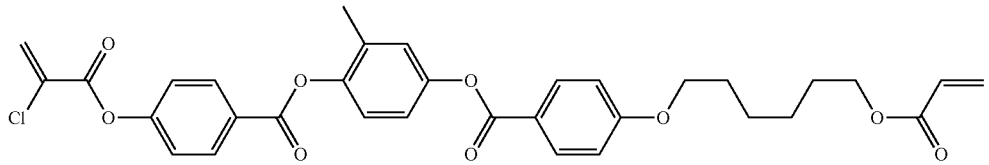
Compound A-62
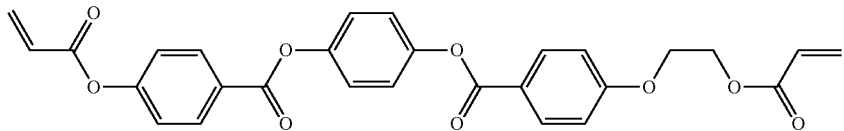
Compound A-63
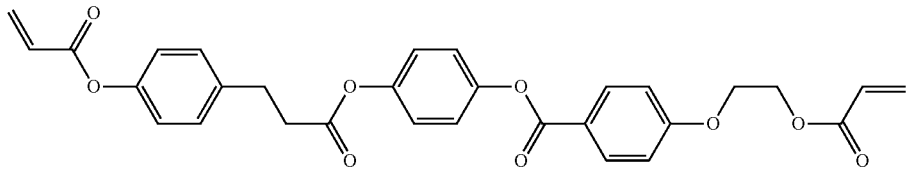

-continued
Compound A-64
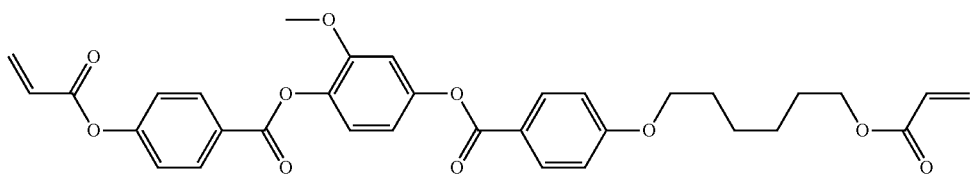
Compound A-65
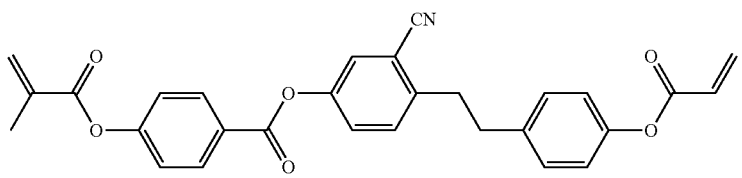
[Chemical Formula 24]
Compound A-66
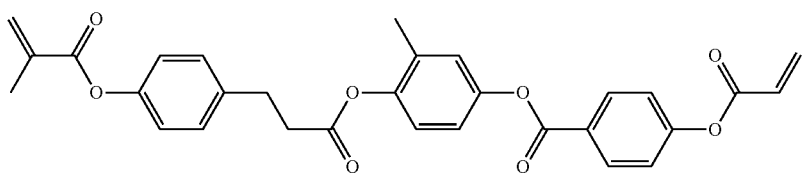
Compound A-67
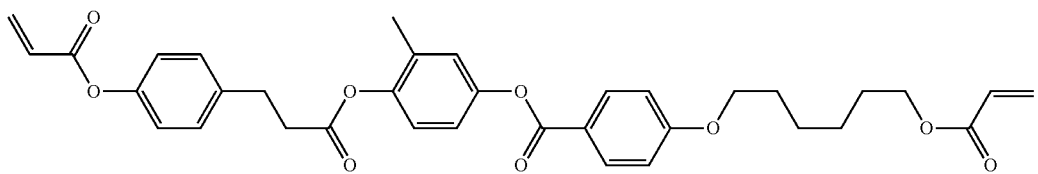
Compound A-68
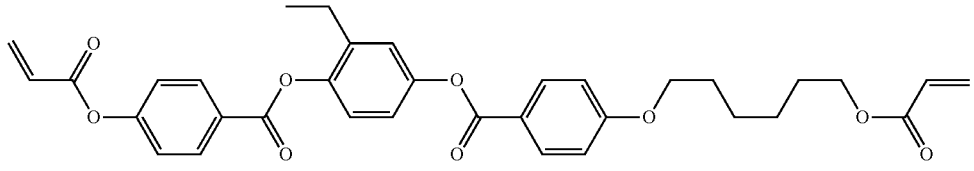
Compound A-69
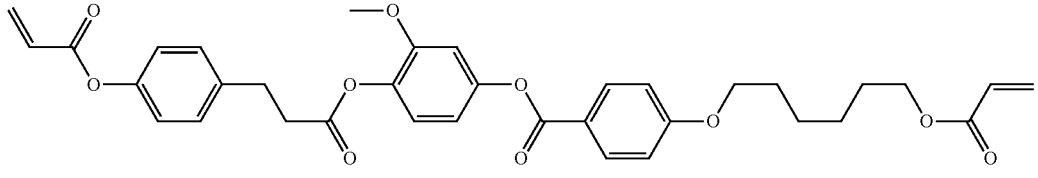
Compound A-70
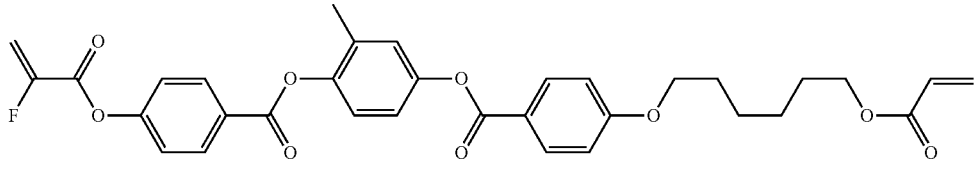
Compound A-71
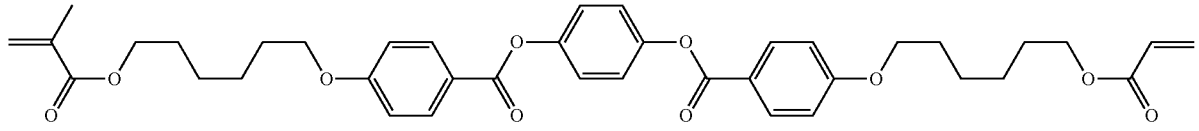

-continued
Compound A-72
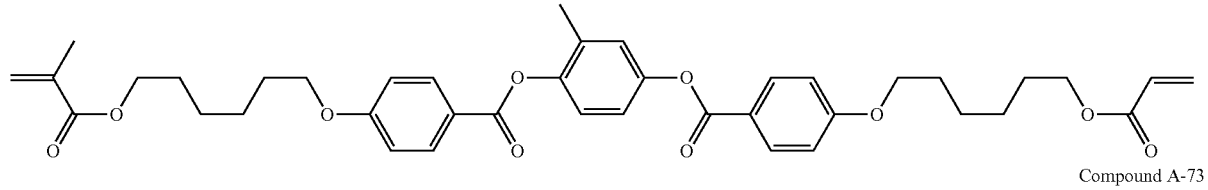
Compound A-73
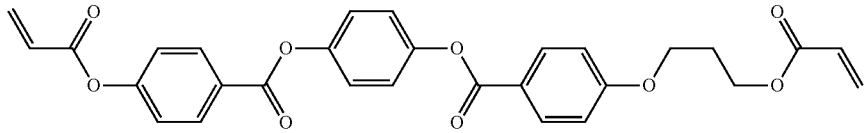
[Chemical Formula 25]
Compound A-74
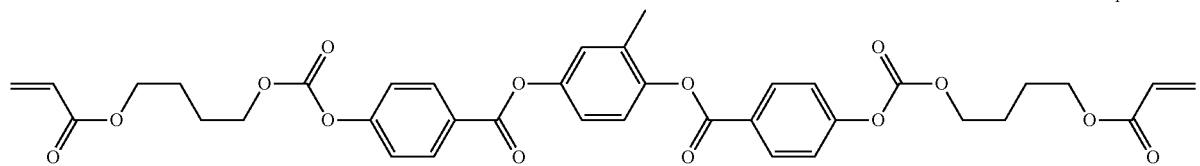
Compound A-75
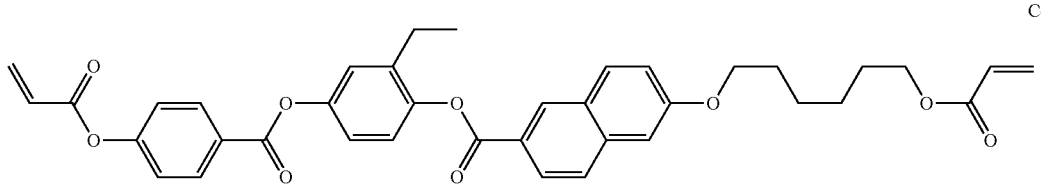
Compound A-76
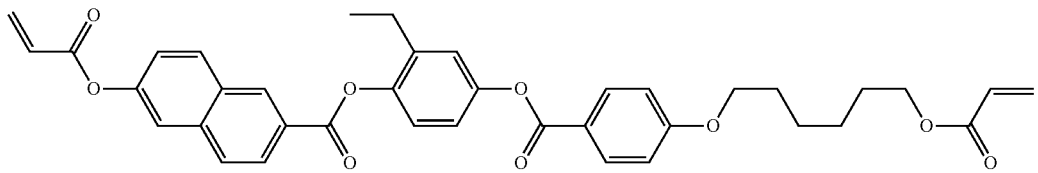
Compound A-77
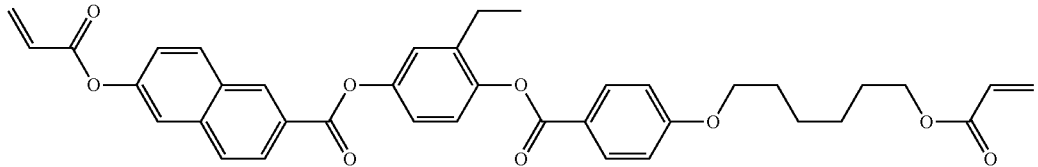
Compound A-78
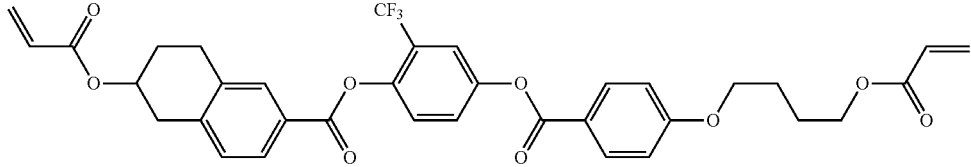
Compound A-79
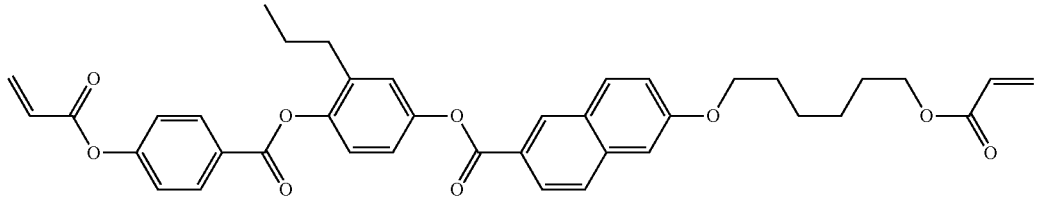

Compound A-80
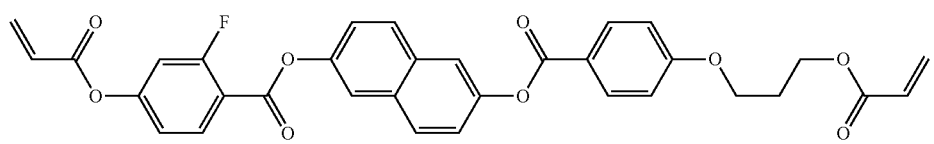
[Chemical Formula 26]
Compound A-81
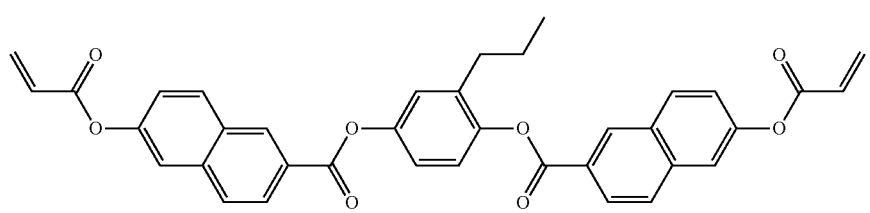
Compound A-82
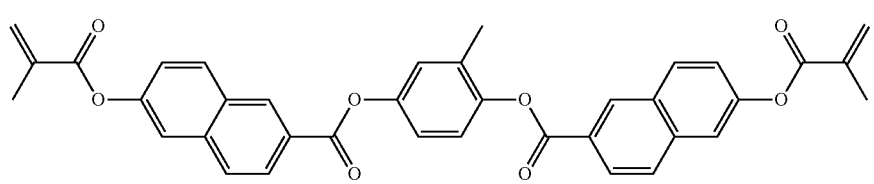
Compound A-83
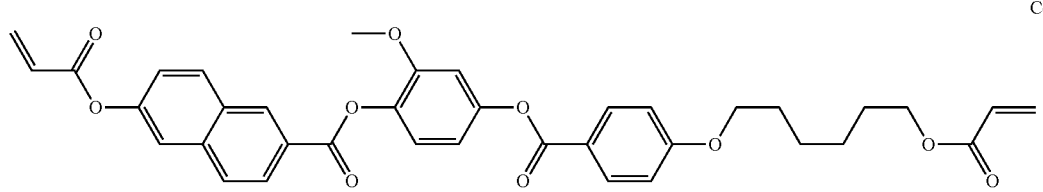
Compound A-84
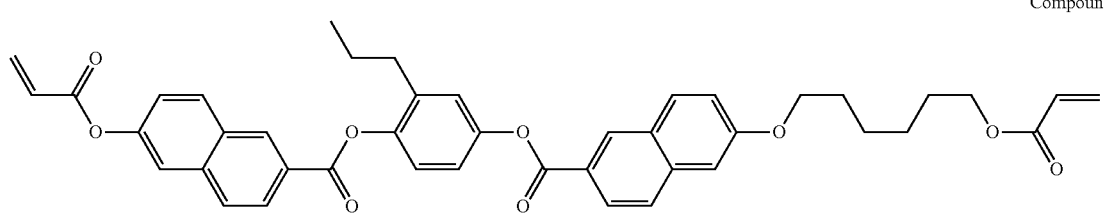
Compound A-85
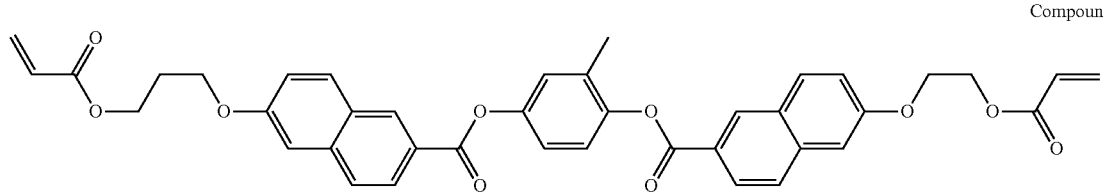
Compound A-86
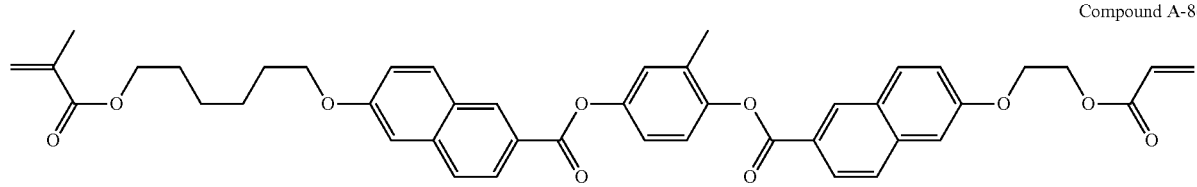
Compound A-87
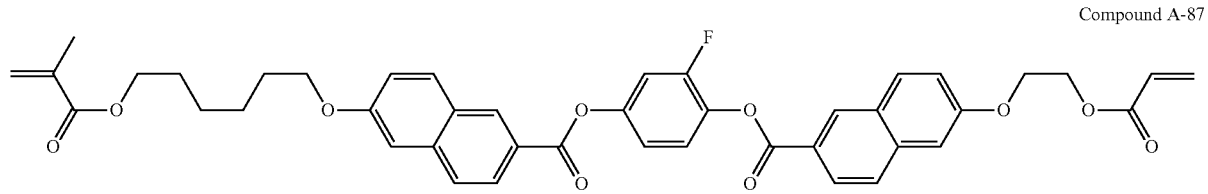

-continued
[Chemical Formula 27]
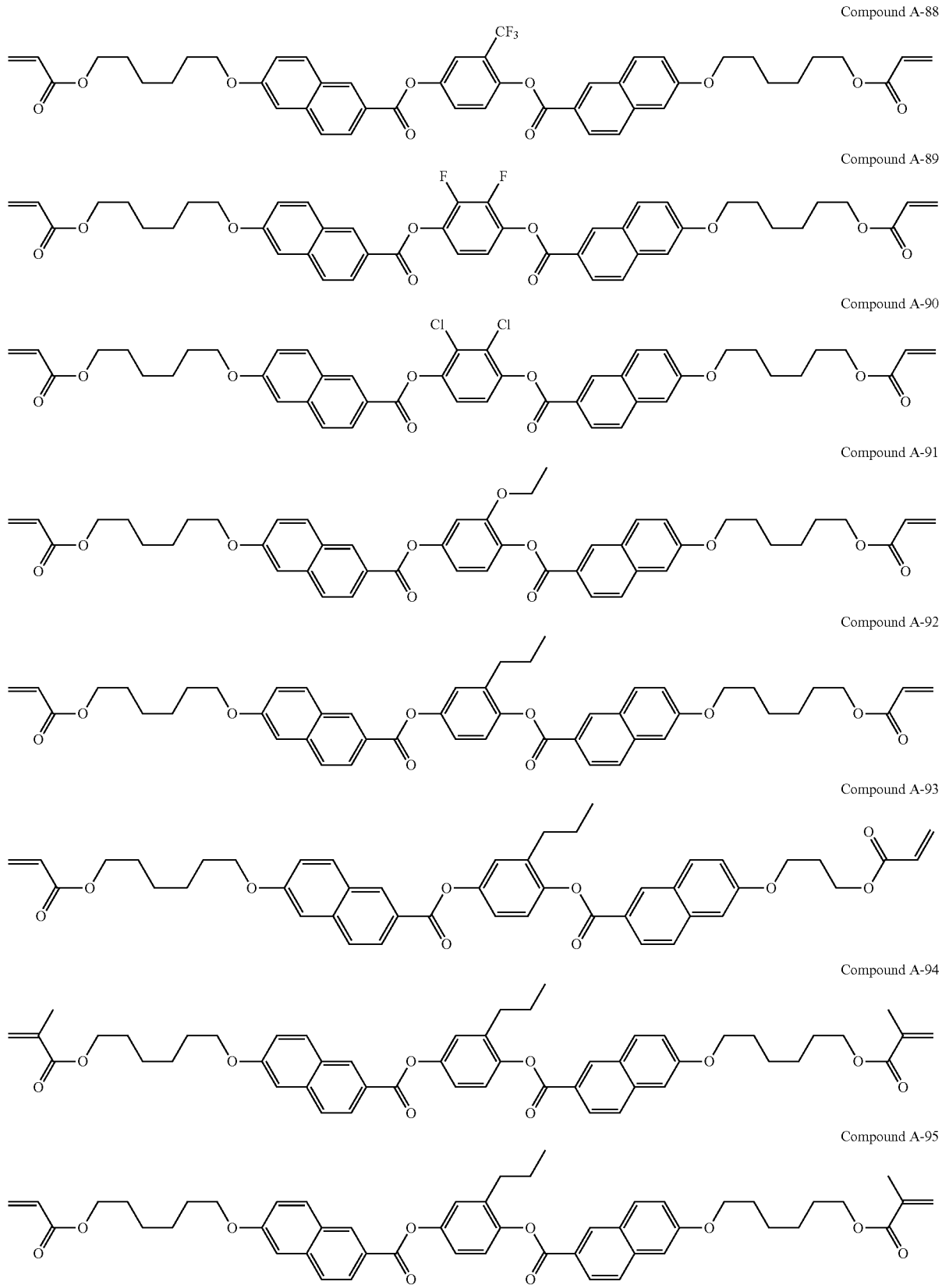
Compound A-88
Compound A-89
Compound A-90
Compound A-91
Compound A-92
Compound A-93
Compound A-94
Compound A-95

-continued
[Chemical Formula 28]
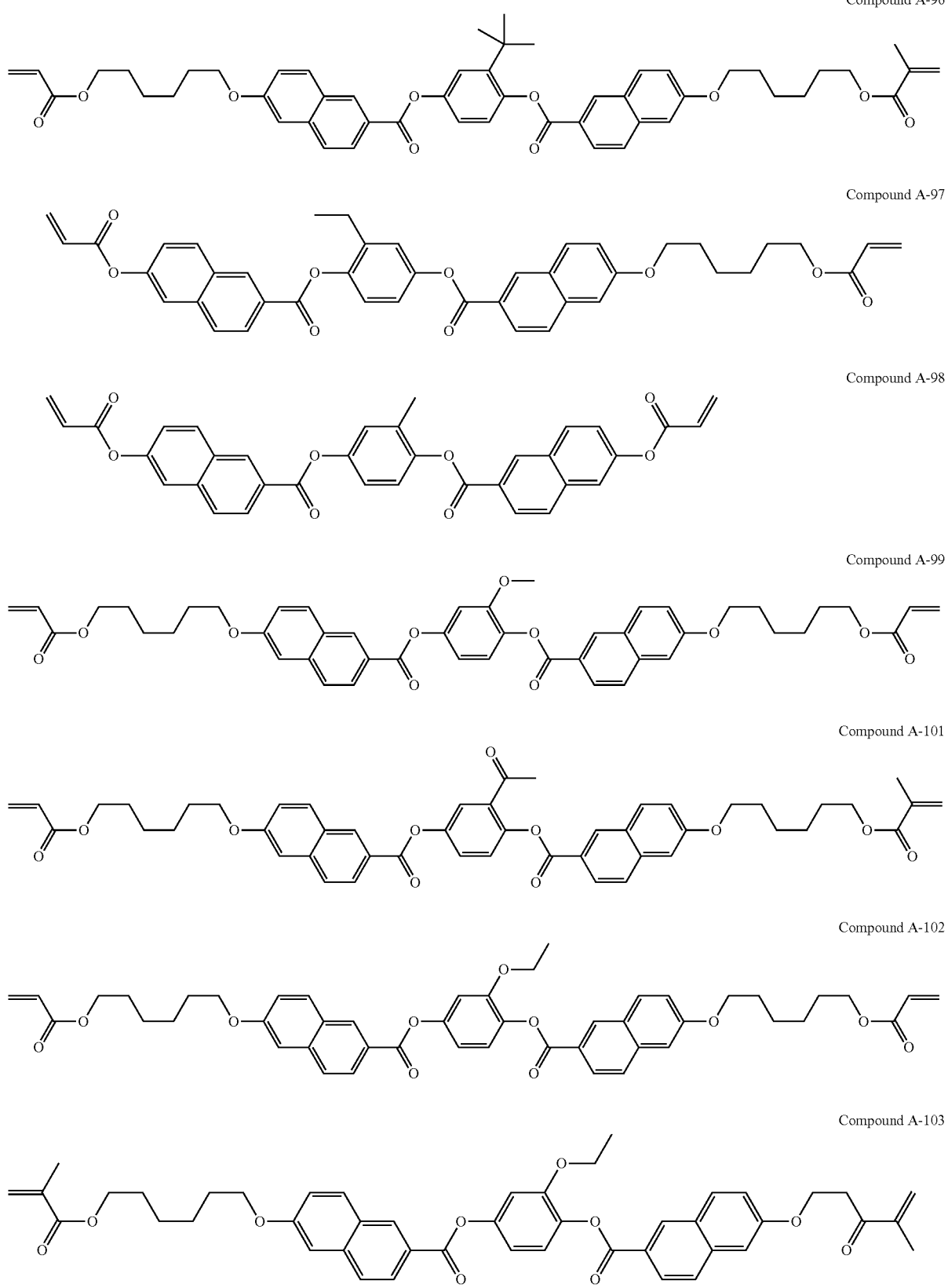
Compound A-96
Compound A-97
Compound A-98
Compound A-99
Compound A-101
Compound A-102
Compound A-103

[Chemical Formula 29]
Compound A-104
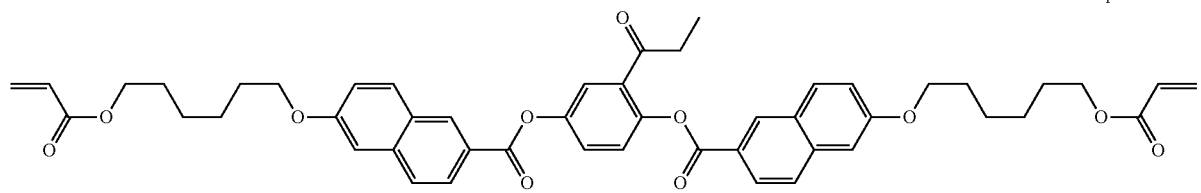
Compound A-105
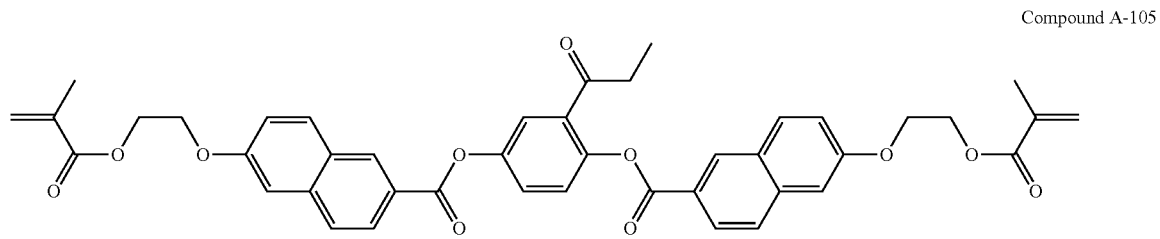
Compound A-106
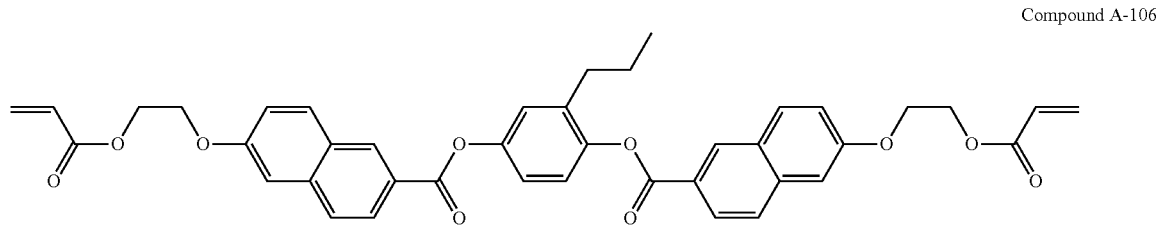
Compound A-107
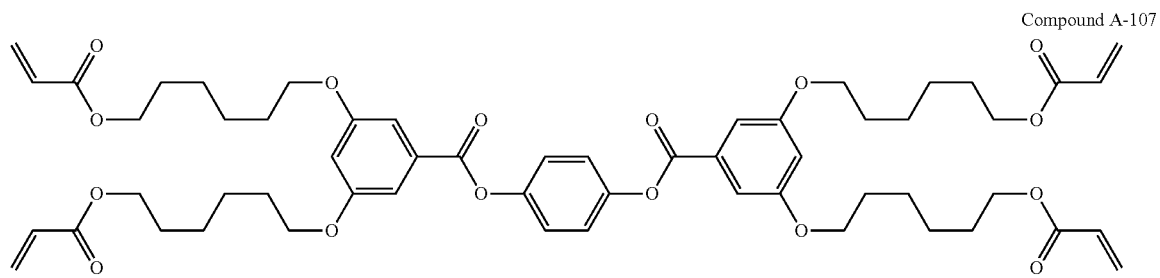
Compound A-108
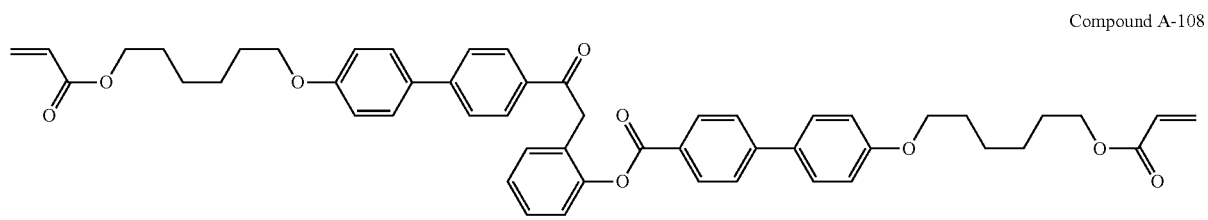
Compound A-109
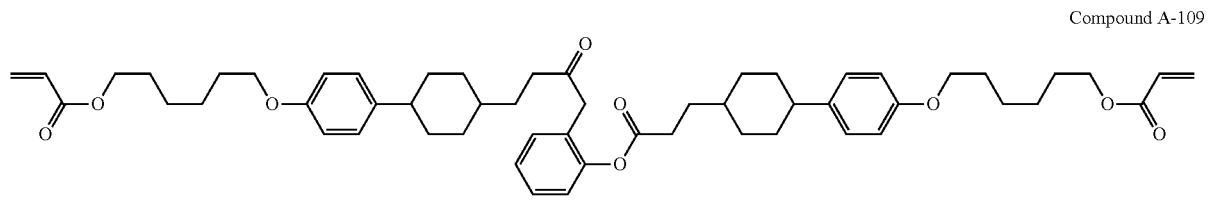

-continued
Compound A-110
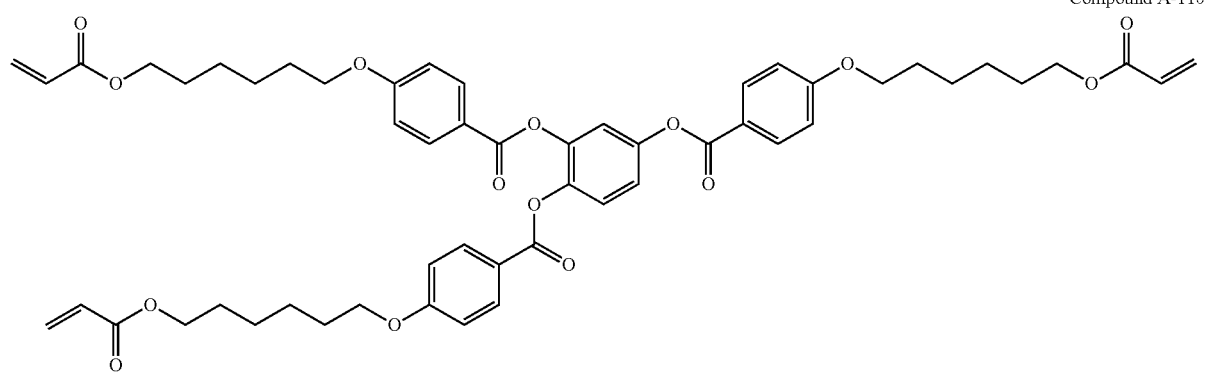
[Chemical Formula 30]
Compound A-111
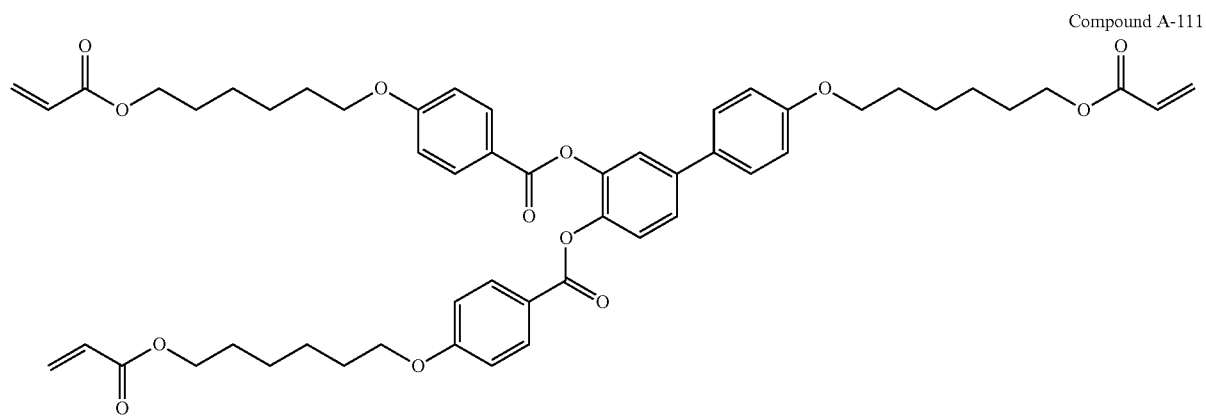
Compound A-112
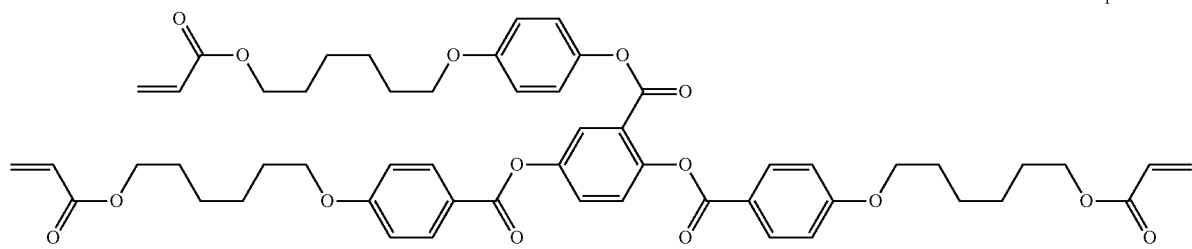
Compound A-113
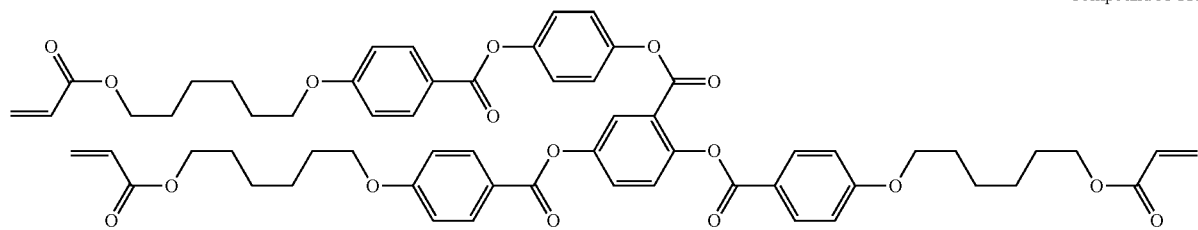
Compound A-114
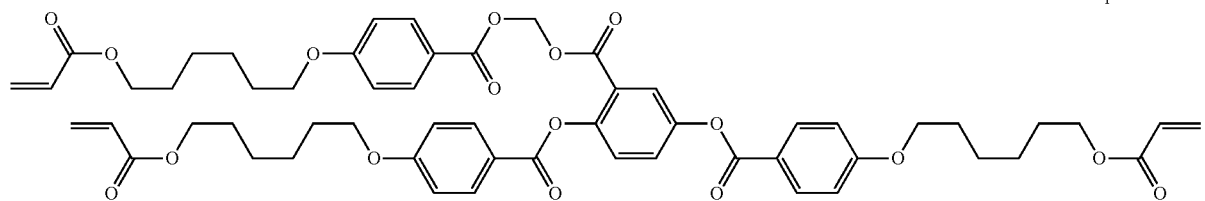

Compound A-115
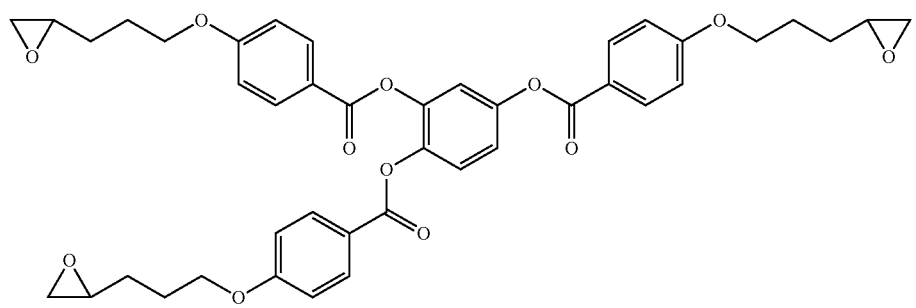
[Chemical Formula 31]
Compound A-116
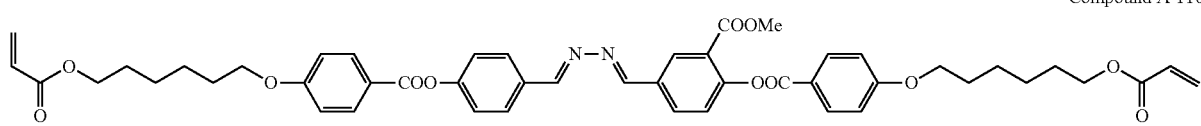
Compound A-117
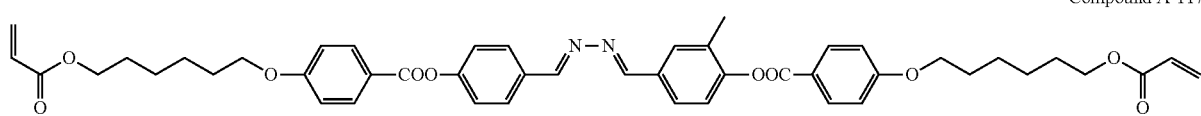
Compound A-118
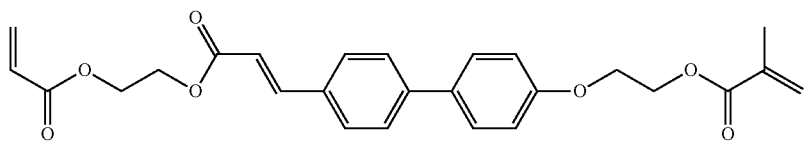
Compound A-119
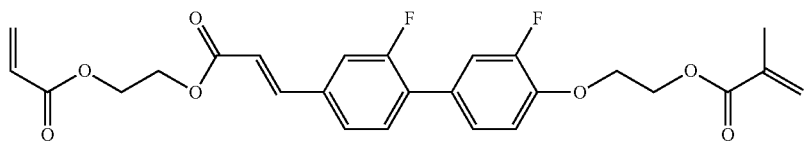
Compound A-120
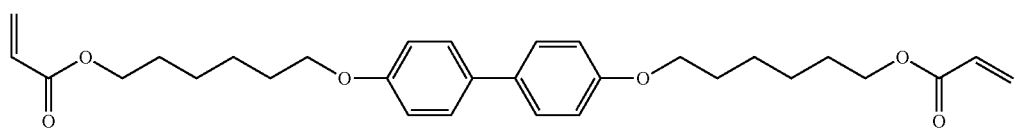
Compound A-121
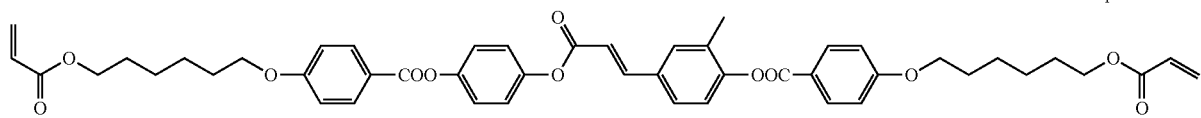
Compound A-122
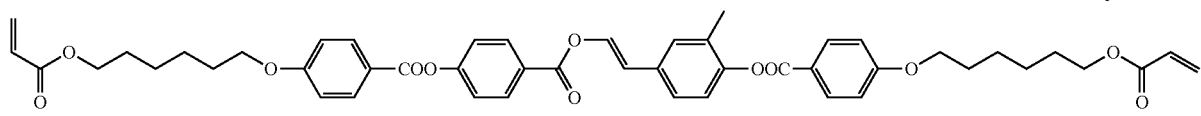

Compound A-123
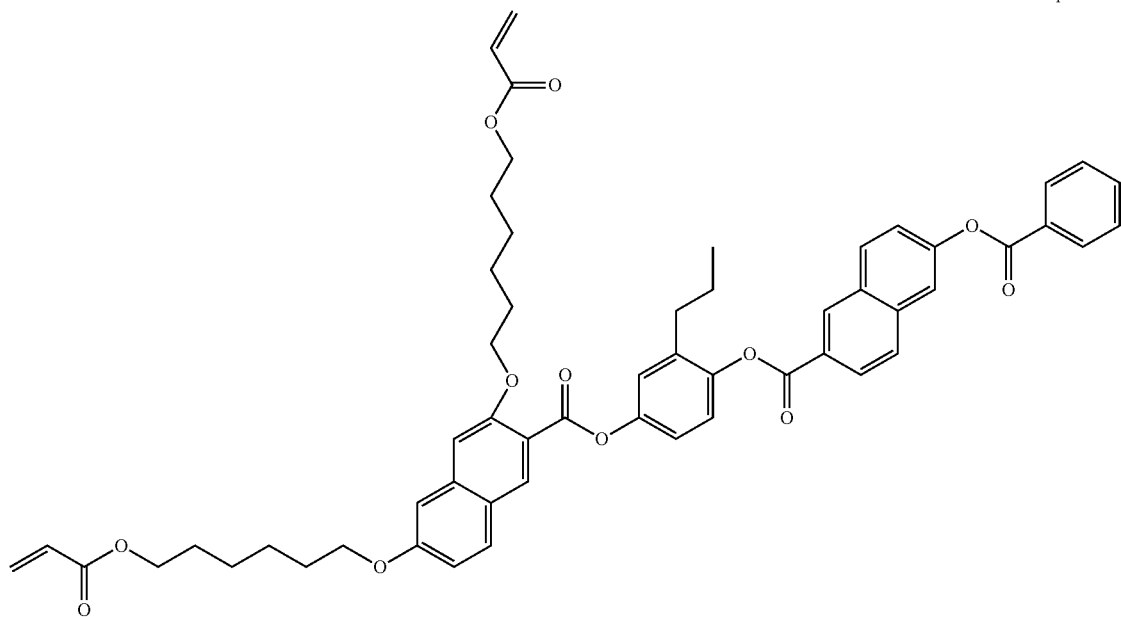
[Chemical Formula 32]
Compound A-124
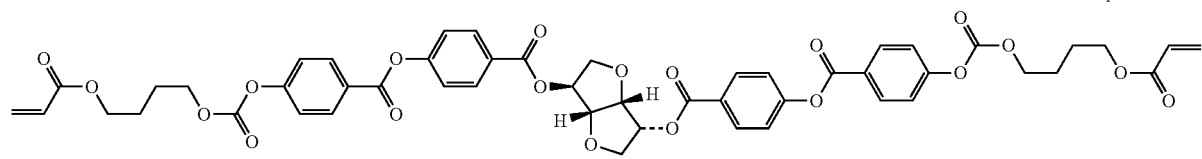
Compound A-125
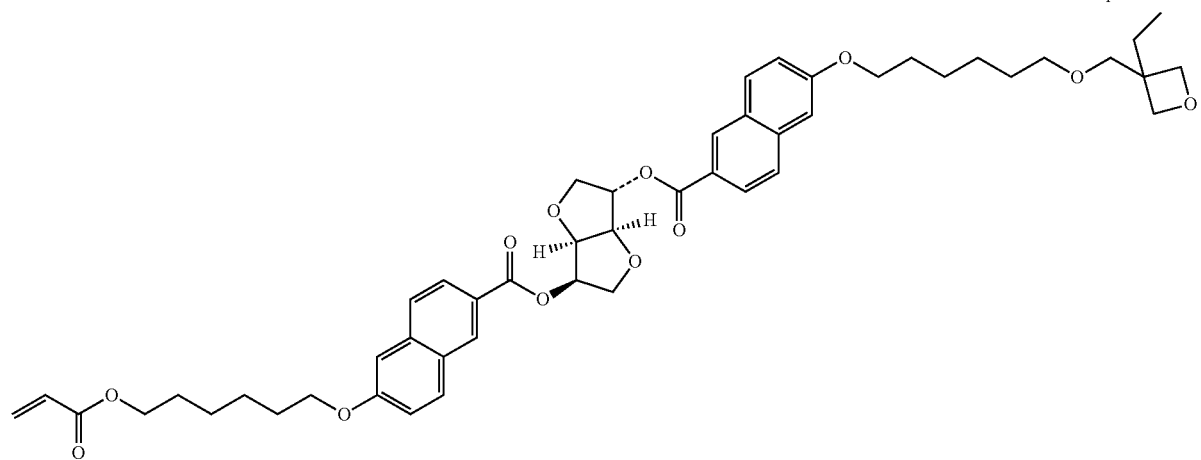

Compound A-126
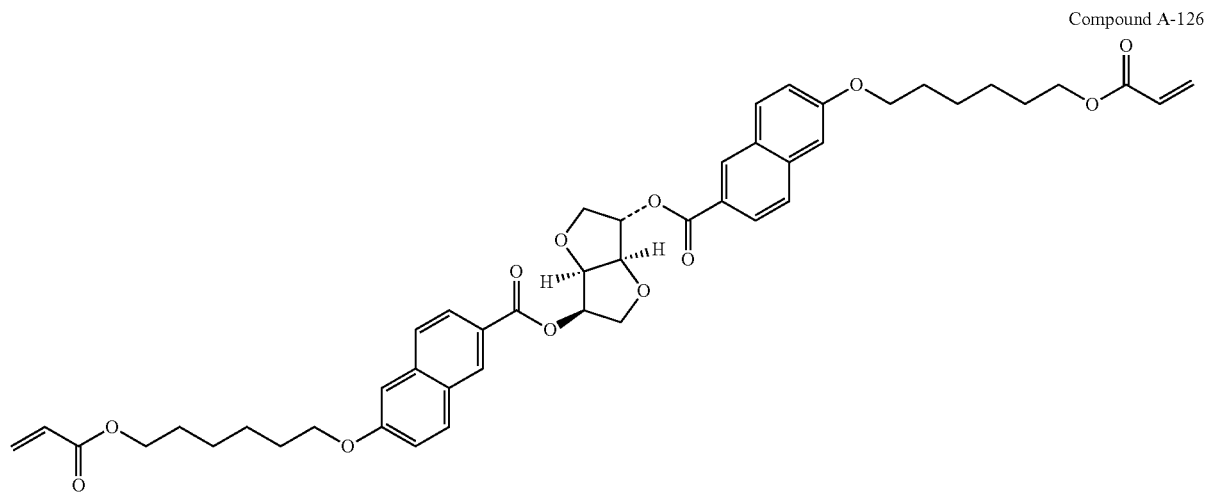
Compound A-127
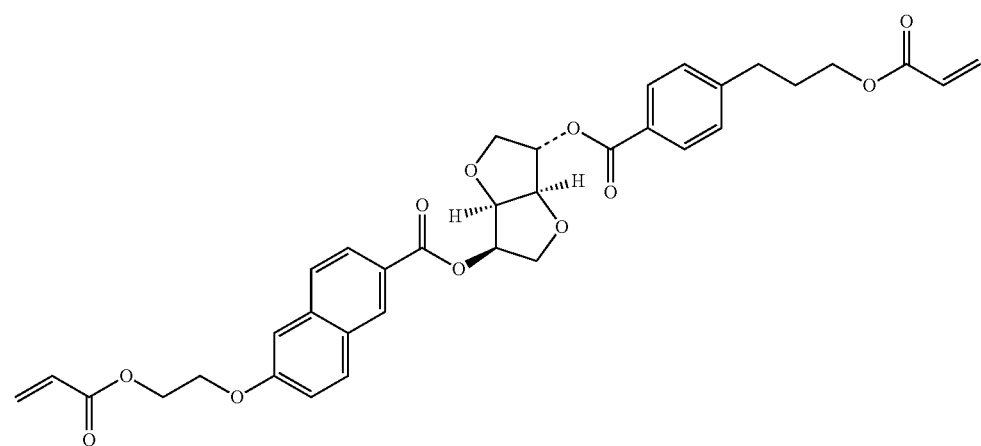
Compound A-128
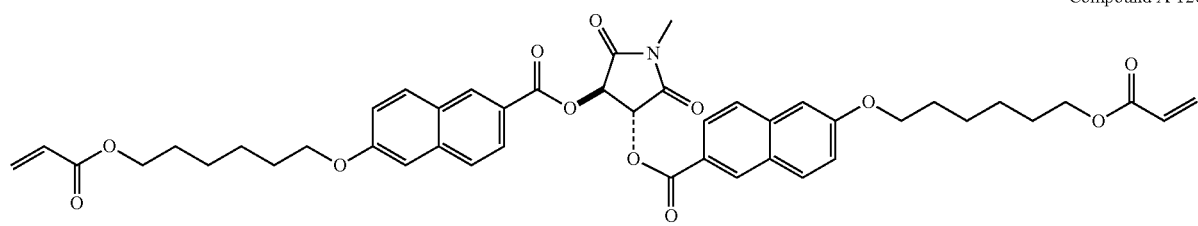
Compound A-129
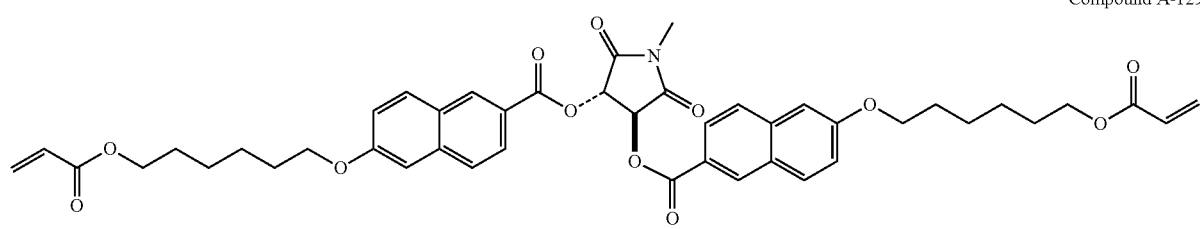
Compound A-130
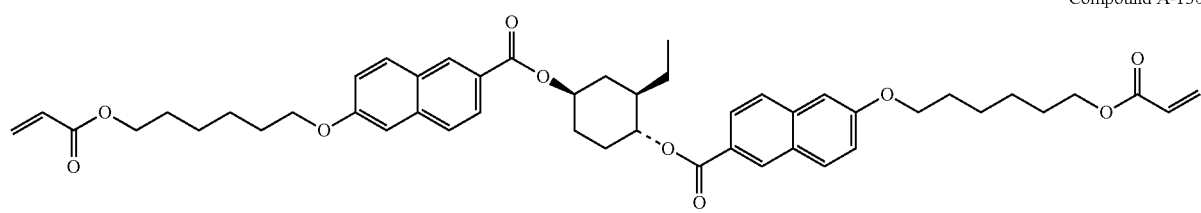

[Chemical Formula 33]

Compound A-131
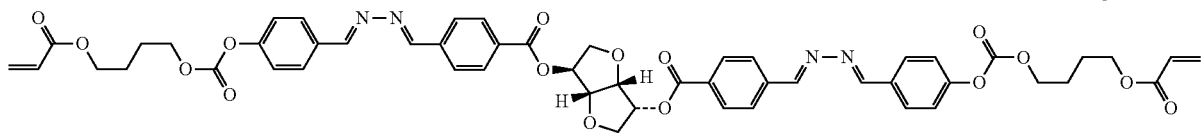

Compound A-132
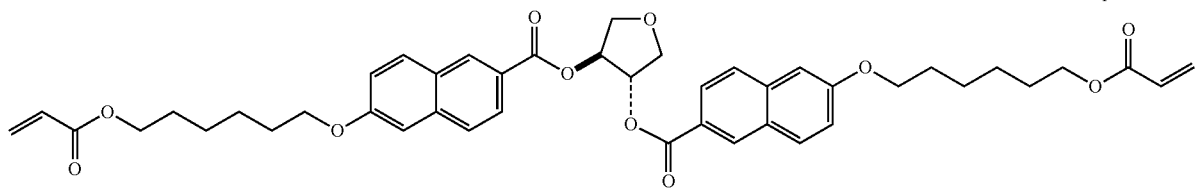

Compound A-133
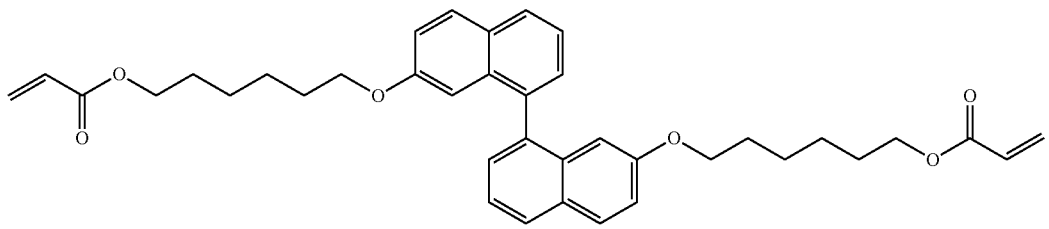

Compound A-134
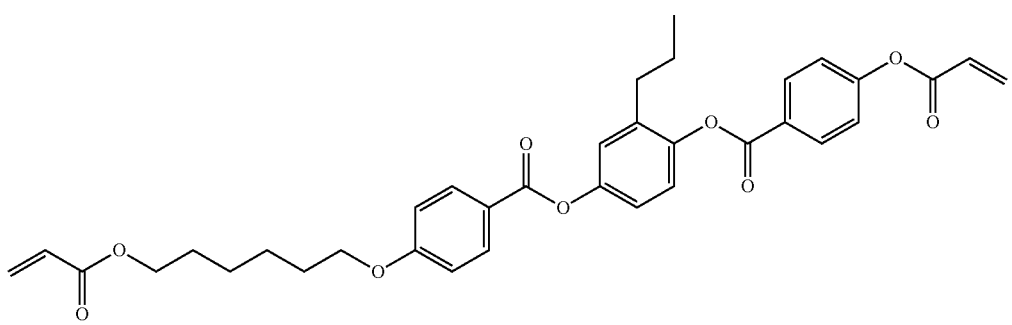

These polymerizable liquid crystal compounds may be used alone as a polymerizable liquid crystalline monomer or in combination of two or more as polymerizable liquid crystalline monomers, and subjected to homopolymerization or copolymerization. Any of these polymerizable liquid crystal compounds may also be copolymerized with an ethylenically unsaturated bond-containing compound. For example, the ethylenically unsaturated bond-containing compound may be an ethylenically unsaturated bond-containing liquid crystalline monomer (hereinafter referred to as an "additional liquid crystalline monomer") other than the polymerizable liquid crystal compound or may be a compound such as a (meth)acrylic ester. The ethylenically unsaturated bond-containing compound is preferably used in such an amount that the content of the polymerizable liquid crystal compound in all monomers will be 5% by weight or more, especially in the range of 10 to 100% by weight, although it may be used in any appropriate amount depending on its structure.

Examples of the (meth)acrylic ester and other ethylenically unsaturated bond-containing compounds include methyl (meth)acrylate, ethyl (meth)acrylate, propyl (meth)acrylate, butyl (meth)acrylate, sec-butyl (meth)acrylate, tert-butyl (meth)acrylate, hexyl (meth)acrylate, 2-ethylhexyl (meth)acrylate, tetrahydrofurfuryl (meth)acrylate, glycidyl (meth)acrylate, allyl (meth)acrylate, allyloxyl (meth)acrylate, cyclohexyl (meth)acrylate, benzyl (meth)acrylate, 1-phenylethyl (meth)acrylate, 2-phenylethyl (meth)acrylate, furfuryl (meth)acrylate, diphenylmethyl (meth)acrylate, naphthyl (meth)acrylate, pentachlorophenyl (meth)acrylate, 2-chloroethyl (meth)acrylate, methyl-α-chloro(meth)acrylate, phenyl-α-bromo(meth)acrylate, trifluoroethyl (meth)acrylate, tetrafluoropropyl (meth)acrylate, polyethylene glycol di(meth)acrylate, 1,4-butanediol di(meth)acrylate, 1,6-hexanediol di(meth)acrylate, trimethylolpropane tri(meth)acrylate, pentaerythritol tri(meth)acrylate, pentaerythritol tetra(meth)acrylate, dipentaerythritol penta(meth)acrylate, dipentaerythritol hexa(meth)acrylate, and other (meth)acrylic esters; and diacetone acrylamide, styrene, vinyltoluene, divinylbenzene, etc.

As mentioned above, the polymerizable liquid crystal compound (A) can be (co)polymerized to form a liquid crystalline (co)polymer. Such a liquid crystalline (co)polymer can be obtained by (co)polymerization of the polymerizable liquid crystal composition containing the polymerizable liquid crystal compound (A).

When used to form a medium capable of emitting polarized light, the (co)polymer of the polymerizable liquid crystal compound (A) preferably shows a liquid crystal phase at least near room temperature, and, in particular, preferably shows a liquid crystal phase at 20° C. or lower.

The content of the polymerizable liquid crystal compound (A) in the polymerizable liquid crystal composition of the invention is preferably 10 to 98% by weight, more preferably 70 to 95% by weight, in view of producing a heat-resistant polymer using the polymerizable liquid crystal composition. If the content of the polymerizable liquid crystal compound (A) is less than 10% by weight, the orientation of the polymerizable liquid crystal compound (A) may be lower, and if the content is more than 98% by weight, it may be difficult to cure the polymerizable liquid crystal composition.

<Colorant (B)>

The colorant (B) may be an organic pigment, an inorganic pigment, or an organic-inorganic hybrid pigment, an organic dye, or the like. These materials may be fluorescent or phosphorescent.

Examples of the organic pigment include insoluble dyes, lake dyes, synthetic organic pigments, etc. Examples of the inorganic pigment include fluorescent inorganic materials including nitrides, oxynitrides, sulfides, oxysulfides, and chlorides, and fluorescent rare earth metal complexes, etc. Examples of the organic-inorganic hybrid pigment include pigments obtained by chemically modifying inorganic pigments with organic materials.

The colorant (B) is preferably an organic dye, more preferably a dye compound.

The dye compound is preferably a fluorescent dye that is capable of being excited by light in the wavelength range from UV to near-IR and has an emission region in the visible light range. Such a fluorescent dye may be any known one, and examples include oligophenylenes such as terphenyl, quarterphenyl, polyphenyl 1, and 7H-benzimidazo(2,1-a) benz(de)isoquinolin-7-one (BBQ); oxazole and oxadiazole derivatives such as 2-(4-biphenylyl)-5-phenyl-1,3,4-oxadiazole (PBD) and 1,4-bis(5-phenyloxazol-2-yl)benzene (POPOP); coumarin derivatives such as 7-hydroxycoumarin, 7-hydroxy-4-methylcoumarin (4-MU), 7-diethylamino-4-methylcoumarin (DAMC), coumarin 6, and coumarin 120; quinolinol derivatives; phthalocyanine derivatives; naphtholactam derivatives; fluorene and derivatives thereof; anthracene and derivatives thereof; xanthene (pyronin, rhodamine, fluorescein) dyes such as Rhodamine 6G and Rhodamine 110; oxazine dyes such as cresyl violet and oxazine 1; stilbene dyes such as trans-4,4'-diphenylstilbene; cyanine dyes; anthraquinone dyes; azomethine dyes; indigo dyes; thioindigo dyes; indane dyes; azulene dyes; perylene dyes; phthaloperin dyes; azine dyes: acridine dyes; thiazine dyes; polyacetylene compounds; phenylenevinylene compounds; phenylene ethynylene compounds; five- and six-membered heterocyclic compounds, etc. These compounds may be used alone or in any mixture.

The molecular structure of the dye compound is preferably such that it has a luminophore and a mesogenic structure, has a ratio of its transverse length to its molecular main chain length of less than 1, and has high linearity, so that it can easily undergo molecular orientation and can emit polarized light with a high degree of polarization.

In view of luminous efficiency, the dye compound is preferably a naphtholactam derivative (B-1), more preferably a naphtholactam derivative represented by formula (IV) below.

[Chemical Formula 34]

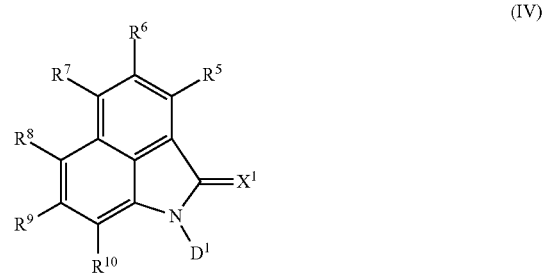

(IV)

wherein $X^1$ represents an oxygen atom or a sulfur atom, $R^5$ to $R^{10}$ and $D^1$ each independently represent a hydrogen atom, a halogen atom, a nitro group, a cyano group, an aldehyde group, a carboxyl group, a hydroxyl group, —NRR', an organosilyl group, an optionally substituted alkyl group of 1 to 30 carbon atoms, an optionally substituted aryl group of 6 to 30 carbon atoms, an optionally substituted arylalkyl group of 7 to 30 carbon atoms, an optionally substituted heterocyclic group of 2 to 30 carbon atoms, or a substituent represented by formula (V), a methylene chain in the alkyl group or the arylalkyl group represented by each of $R^5$ to $R^{10}$ and $D^1$ may be interrupted by —O—, —S—, —SO$_2$—, —CO—, —OCO—, or —COO—, the aryl group represented by each of $R^5$ to $R^{10}$ and $D^1$ and the naphtholactam structure may be linked together via —O—, —S—, —SO$_2$—, —CO—, —OCO—, or —COO—, and the methylene chain may be replaced by —C=C— or —C≡C—, R and R' each independently represent a hydrogen atom, an optionally substituted alkyl group of 1 to 30 carbon atoms, or an optionally substituted aryl group of 6 to 30 carbon atoms, a methylene chain in the alkyl group represented by each of R and R' may be interrupted by —O—, —S—, —SO$_2$—, —CO—, —OCO—, or —COO—, the aryl group represented by each of R and R' and the naphtholactam structure may be linked together via —O—, —S—, —SO$_2$—, —CO—, —OCO—, or —COO—, and the methylene chain may be replaced by —C=C— or —C≡C—, wherein formula (V) is the following:

[Chemical Formula 35]

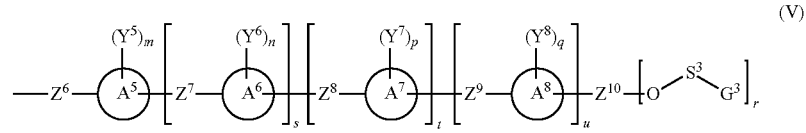

(V)

wherein rings $A^5$, $A^6$, $A^7$, and $A^8$ each independently represent a benzene ring, a cyclohexane ring, a cyclohexene ring, a naphthalene ring, a decahydronaphthalene ring, or a tetrahydronaphthalene ring, $S^3$ represents an alkylene group of 1 to 8 carbon atoms, and the alkylene group represented by $S^3$ may be substituted with a halogen atom, branched, and interrupted by —O—, $Z^6$, $Z^7$, $Z^8$, $Z^9$, and $Z^{10}$ each independently represent a direct bond, -$L^2$-, —O—CO—, —CO—O—, -$L^2$O—, —O$L^2$-, -$L^2$O—CO—, -$L^2$CO—O—, -$L^2$O—CO—O—, —O—CO$L^2$-, —CO—O$L^2$-, —O—CO—O$L^2$-, —CO—CH=CH—, —CH=CH—CO—, —CH=CH—COO—, —COO—CH=CH—, —OCO—CH=CH—, or —CH$_2$=N—N=CH$_2$—, $L^2$ represents an alkylene group of 1 to 8 carbon atoms, the alkylene group may be branched and may be substituted with a halogen atom or a cyano group, and the alkylene group represented by $L^2$ may be interrupted by —O—, —CH=CH—, or —C≡C—, $Y^5$, $Y^6$, $Y^7$, and $Y^8$ each independently represent an alkyl group of 1 to 6 carbon atoms, a halogen atom, or a cyano group, a hydrogen atom of the alkyl group represented by each of $Y^5$, $Y^6$, $Y^7$ and $Y^8$ may be substituted with a halogen atom or a cyano group, and a methylene chain in the alkyl group represented by each of $Y^5$, $Y^6$, $Y^7$ and $Y^8$ may be interrupted by —O— or —CO—, m, n, p, and q are each independently from 0 to 8, s, t, and u are each independently 0 or 1, r is 1 or 2, and $G^3$ represents a substituent selected from the group consisting of substituents represented by formulae (5) to (14):

[Chemical Formula 36]

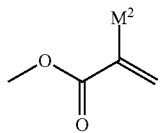
(5)

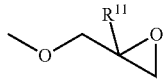
(6)

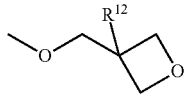
(7)

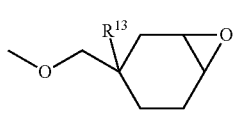
(8)

(9)

(10)

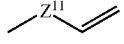
(11)

(12)

-continued

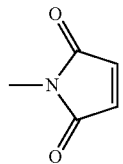
(13)

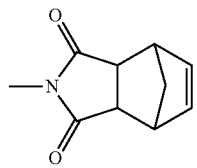
(14)

wherein in formula (5), $M^2$ represents a hydrogen atom, a methyl group, or a halogen atom; in formula (6), $R^{11}$ represents a hydrogen atom or an alkyl group of 1 to 6 carbon atoms; in formula (7), $R^{12}$ represents a hydrogen atom or an alkyl group of 1 to 6 carbon atoms; in formula (8), $R^{13}$ represents a hydrogen atom or an alkyl group of 1 to 6 carbon atoms; in formula (9), $R^{14}$ represents a hydrogen atom or an alkyl group of 1 to 6 carbon atoms; and in formula (11), $Z^1$ represents methylene, —O—, or —CO—.

In formula (IV), the alkyl group of 1 to 30 carbon atoms represented by each of $R^5$ to $R^{10}$, $D^1$, R, and R' may be methyl, ethyl, propyl, isopropyl, butyl, sec-butyl, tert-butyl, isobutyl, amyl, isoamyl, tert-amyl, hexyl, heptyl, isoheptyl, tert-heptyl, n-octyl, isooctyl, tert-octyl, 2-ethylhexyl, n-nonyl, n-decyl, n-dodecyl, n-tridecyl, n-tetradecyl, n-pentadecyl, n-hexadecyl, n-heptadecyl, n-octadecyl, cyclopropyl, cyclobutyl, cyclopentyl, cyclohexyl, cycloheptyl, cyclooctyl, cyclononyl, cyclodecyl, or any other linear, branched, or cyclic alkyl group. A methylene chain in the alkyl group represented by each of $R^5$ to $R^{10}$, $D^1$, R, and R' may be interrupted by —O—, —S—, —SO$_2$—, —CO—, —OCO—, or —COO—, and the methylene chain may be replaced by —C=C— or —C≡C—.

The alkyl group having a methylene chain interrupted by —O— may be methoxy, ethoxy, propyloxy, isopropyloxy, methoxymethyl, ethoxymethyl, 2-methoxyethyl, or the like. The alkyl group having a methylene chain interrupted by —S— may be methylthio, ethylthio, butylthio, pentylthio, or the like. The alkyl group having a methylene chain interrupted by —SO$_2$— may be methylsulfonyl, ethylsulfonyl, butylsulfonyl, pentylsulfonyl, or the like. The alkyl group having a methylene chain interrupted by —CO— may be acetyl, 1-carbonylethyl, acetylmethyl, 1-carbonylpropyl, 2-oxobutyl, 2-acetylethyl, 1-carbonylisopropyl, cyclopentanecarbonyl, or the like. The alkyl group having a methylene chain interrupted by —OCO— may be an acetoxy group, a propionyloxy group, a butyryloxy group, or the like. The alkyl group having a methylene chain interrupted by —COO— may be a methoxycarbonyl group, an ethoxycarbonyl group, an isopropyloxycarbonyl group, or the like.

Some alkyl groups having a methylene chain interrupted by —O—, —S—, —SO$_2$—, —CO—, —OCO—, or —COO— have been listed above, but it should be noted that these are mere examples and that the position and number of the interrupting moieties are not restricted.

In formula (IV), the optionally substituted aryl group of 6 to 30 carbon atoms represented by each of $R^5$ to $R^{10}$, $D^1$, R, and R' may be a phenyl group, a naphthyl group, a biphenyl group, or the like, the aryl group represented by each of $R^5$ to $R^{10}$, $D^1$, R, and R' and the naphtholactam structure may be linked together via —O—, —S—, —SO$_2$—, —CO—, —OCO—, or —COO—, and the methylene chain may be replaced by —C=C— or —C≡C—.

The group having the aryl group and the intervening —O— moiety linked to the naphtholactam structure may be phenoxy, 1-naphthoxy, 2-naphthoxy, or the like. The group having the aryl group and the intervening —S— moiety linked to the naphtholactam structure may be phenylthio, 1-naphthylthio, 2-naphthylthio, or the like. The group having the aryl group and the intervening —SO$_2$— moiety linked to the naphtholactam structure may be phenylsulfone, 1-naphthylsulfone, 2-naphthylsulfone, or the like. The group having the aryl group and the intervening —CO— moiety linked to the naphtholactam structure may be benzoyl, 1-naphthoyl, 2-naphthoyl, or the like. The group having the aryl group and the intervening —OCO— moiety linked to the naphtholactam structure may be benzoyloxy, 1-naphthoyloxy, 2-naphthoyloxy, or the like. The group having the aryl group and the intervening —COO— moiety linked to the naphtholactam structure may be a phenoxycarbonyl group, a 1-naphthoxycarbonyl group, or the like.

Some groups having the aryl group and the intervening —O—, —S—, —SO$_2$—, —CO—, —OCO—, or —COO— moiety linked to the naphtholactam structure have been listed above, but it should be noted that these are mere examples and that the position and number of the intervening moieties are not restricted.

In formula (IV), for example, the optionally substituted arylalkyl group of 7 to 30 carbon atoms represented by each of $R^5$ to $R^{10}$ and $D^1$ may be benzyl, phenethyl, 2-phenylpropyl, diphenylmethyl, triphenylmethyl, 4-chlorophenylmethyl, or the like, and a methylene chain in the alkyl group represented by each of $R^5$ to $R^{10}$ and $D^1$ may be interrupted by —O—, —S—, —SO$_2$—, —CO—, —OCO—, or —COO—, and the methylene chain may be replaced by —C=C— or —C≡C—.

The arylalkyl group having a methylene chain interrupted by —O— may be benzyloxy, phenoxymethyl, phenoxyethyl, a 1-naphthylmethoxy group, a 2-naphthylmethoxy group, 1-anthrylmethoxy, or the like. The arylalkyl group having a methylene chain interrupted by —S— may be benzylthio, phenylthiomethyl, phenylthioethyl, or the like. The arylalkyl group having a methylene chain interrupted by —SO$_2$— may be benzylsulfonyl or the like. The arylalkyl group having a methylene chain interrupted by —CO— may be a benzylcarbonyl group, phenethylcarbonyl, a 1-naphthylmethylcarbonyl group, or the like. The arylalkyl group having a methylene chain interrupted by —OCO— may be a phenylacetate group, a 1-naphthylacetate group, or the like. The arylalkyl group having a methylene chain interrupted by —COO— may be a benzyloxycarbonyl group, a phenethyloxycarbonyl group, or the like.

Some arylalkyl groups having a methylene chain interrupted by —O—, —S—, —SO$_2$—, —CO—, —OCO—, or —COO— have been listed above, but it should be noted that these are mere examples and that the position and number of the interrupting moieties are not restricted.

In formula (IV), for example, the optionally substituted heterocyclic group of 2 to 30 carbon atoms represented by each of $R^5$ to $R^{10}$ and $D^1$ may be pyridyl, pyrimidyl, pyridazyl, piperidyl, pyranyl, pyrazolyl, triazyl, pyrrolyl, quinolyl, isoquinolyl, imidazolyl, benzimidazolyl, triazolyl, furyl, furanyl, benzofuranyl, thienyl, thiophenyl, benzothiophenyl, thiadiazolyl, thiazolyl, benzothiazolyl, oxazolyl, benzoxazolyl, isothiazolyl, isoxazolyl, indolyl, 2-pyrrolidinone-1-yl, 2-piperidone-1-yl, 2,4-dioxyimidazolidine-3-yl, 2,4-dioxyoxazolidine-3-yl, or the like.

In formula (IV), the organosilyl group represented by each of $R^5$ to $R^{10}$ and $D^1$ may be methylsilyl, dimethylsilyl, trimethylsilyl, ethylsilyl, diethylsilyl, triethylsilyl, phenylsilyl, diphenylsilyl, triphenylsilyl, dimethylphenylsilyl, methyldiphenylsilyl, tripropylsilyl, tributylsilyl, trihexylsilyl, tricyclohexylsilyl, trimethylsilylthio, methylsilylamino, or the like.

Examples of the halogen atom represented by each of $R^5$ to $R^{10}$ in formula (IV) include those listed above for formula (I).

In formula (IV), the optionally substituted alkyl group of 1 to 30 carbon atoms and the optionally substituted aryl group of 6 to 30 carbon atoms represented by each of $R^5$ to $R^{10}$, $D^1$, R, and R' and the optionally substituted arylalkyl group of 7 to 30 carbon atoms represented by each of $R^5$ to $R^{10}$ and $D^1$ may have a substituent, examples of which include alkyl groups such as methyl, ethyl, propyl, isopropyl, cyclopropyl, butyl, sec-butyl, tert-butyl, isobutyl, amyl, isoamyl, tert-amyl, cyclopentyl, hexyl, 2-hexyl, 3-hexyl, cyclohexyl, bicyclohexyl, 1-methylcyclohexyl, heptyl, 2-heptyl, 3-heptyl, isoheptyl, tert-heptyl, n-octyl, isooctyl, tert-octyl, 2-ethylhexyl, nonyl, isononyl, and decyl; alkoxy groups such as methyloxy, ethyloxy, propyloxy, isopropyloxy, butyloxy, sec-butyloxy, tert-butyloxy, isobutyloxy, amyloxy, isoamyloxy, tert-amyloxy, hexyloxy, cyclohexyloxy, heptyloxy, isoheptyloxy, tert-heptyloxy, n-octyloxy, isooctyloxy, tert-octyloxy, 2-ethylhexyloxy, nonyloxy, and decyloxy; alkylthio groups such as methylthio, ethylthio, propylthio, isopropylthio, butylthio, sec-butylthio, tert-butylthio, isobutylthio, amylthio, isoamylthio, tert-amylthio, hexylthio, cyclohexylthio, heptylthio, isoheptylthio, tertheptylthio, n-octylthio, isooctylthio, tert-octylthio, and 2-ethylhexylthio; alkenyl groups such as vinyl, 1-methylethenyl, 2-methylethenyl, 2-propenyl, 1-methyl-3-propenyl, 3-butenyl, 1-methyl-3-butenyl, isobutenyl, 3-pentenyl, 4-hexenyl, cyclohexenyl, bicyclohexenyl, heptenyl, octenyl, decenyl, pentadecenyl, eicosenyl, and tricosenyl; arylalkyl groups such as benzyl, phenethyl, diphenylmethyl, triphenylmethyl, styryl, and cinnamyl; aryl groups such as phenyl and naphthyl; aryloxy groups such as phenoxy and naphthyloxy; arylthio groups such as phenylthio and naphthylthio; halogen atoms such as fluorine, chlorine, bromine, and iodine; acyl groups such as acetyl, 2-chloroacetyl, propionyl, octanoyl, acryloyl, methacryloyl, phenylcarbonyl (benzoyl), phthaloyl, 4-trifluoromethylbenzoyl, pivaloyl, salicyloyl, oxaloyl, stearoyl, methoxycarbonyl, ethoxycarbonyl, tert-butoxycarbonyl, n-octadecyloxycarbonyl, and carbamoyl; acyloxy groups such as acetyloxy and benzoyloxy; amino and substituted amino groups such as ethylamino, dimethylamino, diethylamino, butylamino, cyclopentylamino, 2-ethylhexylamino, dodecylamino, anilino, chlorophenylamino, toluidino, anisidino, N-methyl-anilino, diphenylamino, naphthylamino, 2-pyridylamino, methoxycarbonylamino, phenoxycarbonylamino, acetylamino, benzoylamino, formylamino, pivaloylamino, lauroylamino, carbamoylamino, N,N-dimethylaminocarbonylamino, N,N-diethylaminocarbonylamino, morpholinocarbonylamino, methoxycarbonylamino, ethoxycarbonylamino, tert-butoxycarbonylamino, n-octadecyloxycarbonylamino, N-methyl-methoxycarbonylamino, phenoxycarbonylamino, sulfamoylamino, N,N-dimethylaminosulfonylamino, methylsulfonylamino, butylsulfonylamino, and phenylsulfonylamino; and other groups such as a sulfonamide group, a sulfonyl group, a carboxyl group, a cyano group, a sulfo group, a hydroxyl group, a nitro group, a mercapto group, an imide group, a carbamoyl group, and a sulfonamide group. These groups may be further substituted. Carboxyl and sulfo groups may form salts. If the group represented by each of $R^6$ to $R^{10}$, $D^1$, R, and R' is substituted with a carbon atom-containing substituent, the total number of carbon atoms in the group, including those in the substituent, shall fall within the specified range.

In formula (V), examples of the alkylene group of 1 to 8 carbon atoms represented by $S^3$, the optionally branched alkylene group of 1 to 8 carbon atoms represented by $L^2$ optionally substituted with a halogen atom or a cyano group, the alkyl group of 1 to 6 carbon atoms represented by each of $Y^5$, $Y^6$, $Y^7$, and $Y^8$, the halogen atom represented by each of $Y^5$, $Y^6$, $Y^7$, and $Y^8$, the halogen atom represented by $M^2$ in formula (5), and the alkyl group of 1 to 6 carbon atoms represented by each of $R^{11}$ in formula (6), $R^{12}$ in formula (7), $R^{13}$ in formula (8), and $R^{14}$ in formula (9) include those listed above for formula (I).

The naphtholactam derivative represented by formula (IV) is preferably such that $X^1$ is an oxygen atom, and at least one of $R^5$ to $R^{10}$, especially $R^8$, is a substituent represented by formula (V), because such a naphtholactam derivative has a structure having a ratio of its transverse length to its molecular main chain length of less than 1 and having high linearity, so that it can easily undergo molecular orientation and can emit polarized light with a high degree of polarization.

Besides the substituent represented by formula (V), the moiety represented by each of $R^5$ to $R^{10}$ is preferably a hydrogen atom, a halogen atom, a nitro group, a cyano group, an aldehyde group, a carboxyl group, a hydroxyl group, —NRR', an alkyl group of 1 to 30 carbon atoms, an aryl group of 6 to 30 carbon atoms, an arylalkyl group of 7 to 30 carbon atoms, an alkyl group of 1 to 30 carbon atoms with a methylene chain interrupted by —O—, —CO—, or —COO—, a halogen-substituted alkyl group of 1 to 30 carbon atoms, an arylalkyl group of 7 to 30 carbon atoms with a methylene chain interrupted by —SO$_2$—, or an alkyl group of 1 to 30 carbon atoms with a methylene chain replaced by —C=C— or —C≡C—, because raw materials for these moieties are easily available.

$D^1$ is preferably a hydrogen atom, an alkyl group of 1 to 30 carbon atoms, an aryl group of 6 to 30 carbon atoms, an arylalkyl group of 7 to 30 carbon atoms, a halogen atom, a carboxyl group, a hydroxyl- or haloalkyl-substituted alkyl group of 1 to 30 carbon atoms, an alkoxy- or haloalkyl-substituted aryl group of 6 to 30 carbon atoms, or an alkyl group of 1 to 30 carbon atoms with a methylene chain interrupted by —CO—, because raw materials for such moieties are easily available.

In formula (V), rings $A^5$, $A^6$, $A^7$, and $A^8$ are preferably benzene rings because they can increase linearity, and $Z^6$, $Z^7$, $Z^8$, $Z^9$, and $Z^{10}$ are each preferably a direct bond, —O—CO—, or —CO—O— because raw materials for such moieties are easily available.

$G^3$ is preferably the group represented by formula (5) because in this case, the copolymerization with the polymerizable liquid crystal compound (A) will be easy.

Examples of the naphtholactam derivative represented by formula (IV) according to the invention include, but are not limited to, compounds B-1 to B-52 shown below.

[Chemical Formula 37]

Compound B-1

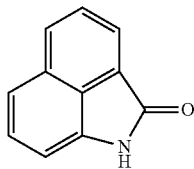

Compound B-2

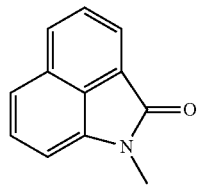

Compound B-3

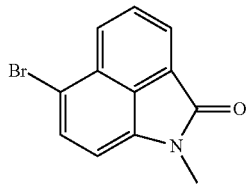

Compound B-4

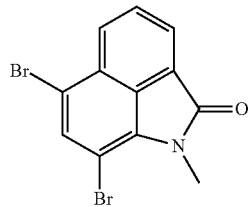

Compound B-5

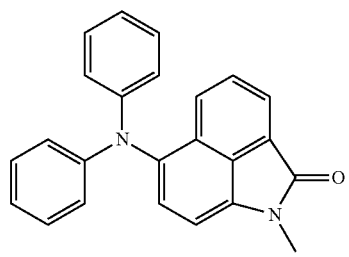

Compound B-6

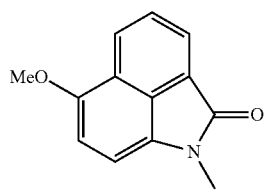

-continued
Compound B-7
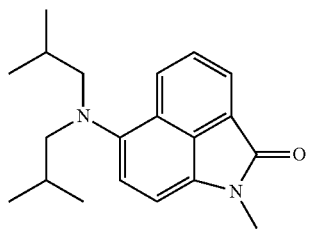
Compound B-8
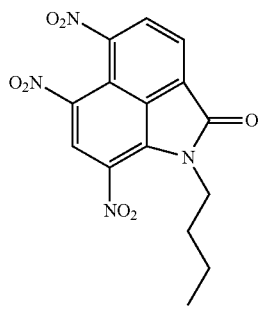
Compound B-9
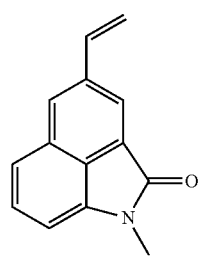
Compound B-10
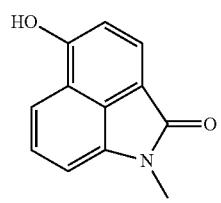
Compound B-11
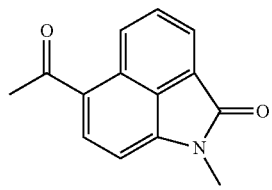
Compound B-12
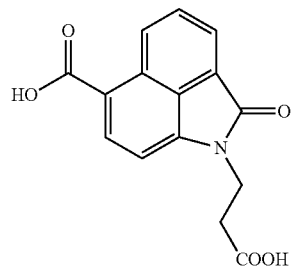
Compound B-13
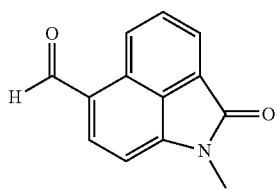
Compound B-14
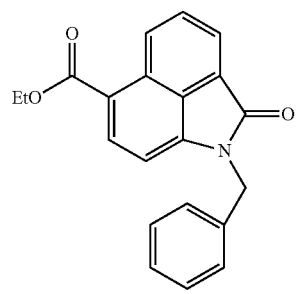
Compound B-15
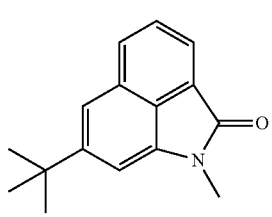
Compound B-16
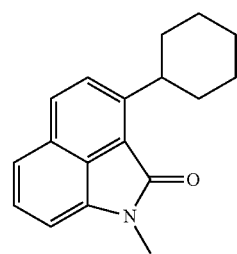

[Chemical Formula 38]
Compound B-17
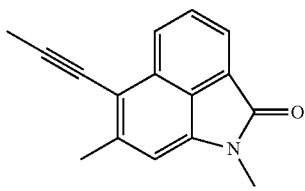
Compound B-18
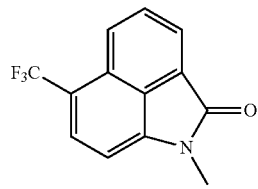
Compound B-19
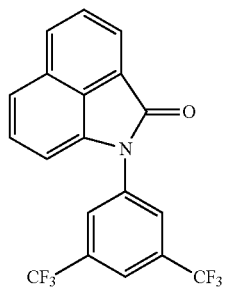
Compound B-20
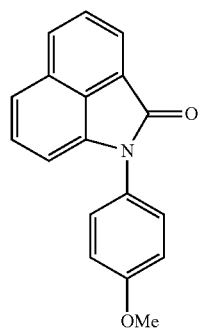
Compound B-21
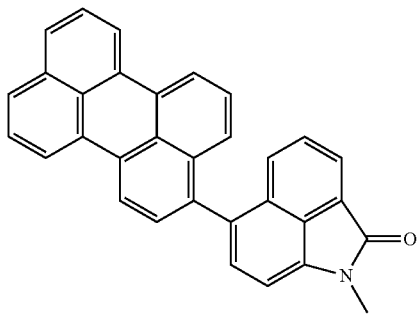
Compound B-22
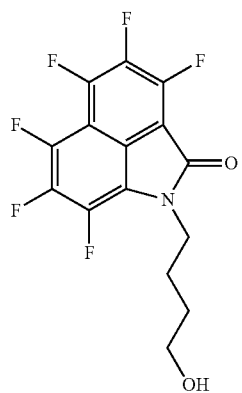
Compound B-23
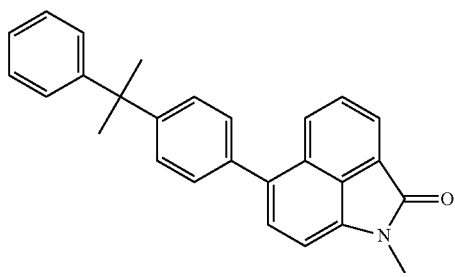
Compound B-24
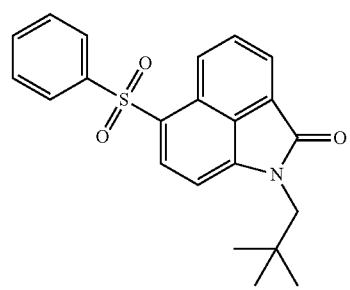

-continued
Compound B-25
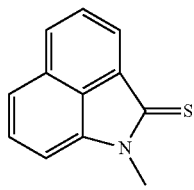
Compound B-26
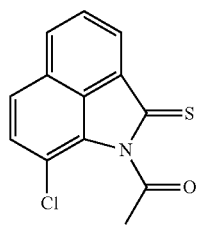
Compound B-27
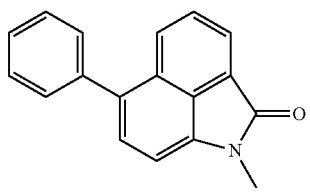
Compound B-28
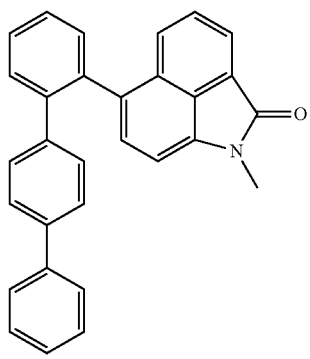
Compound B-29
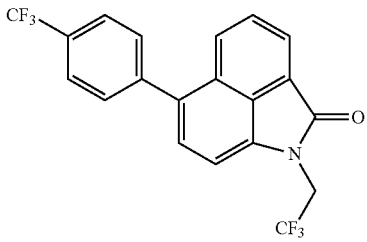
Compound B-30
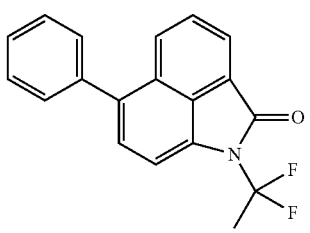
[Chemical Formula 39]
Compound B-31
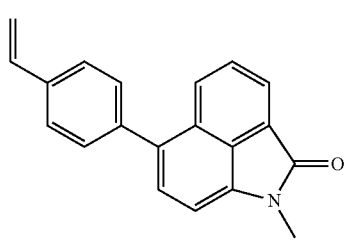
Compound B-32
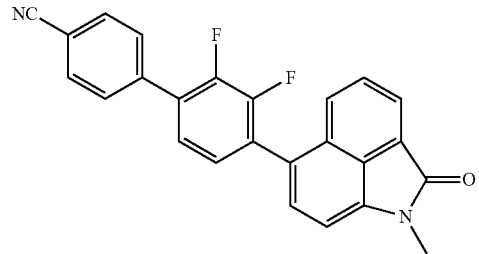
Compound B-33
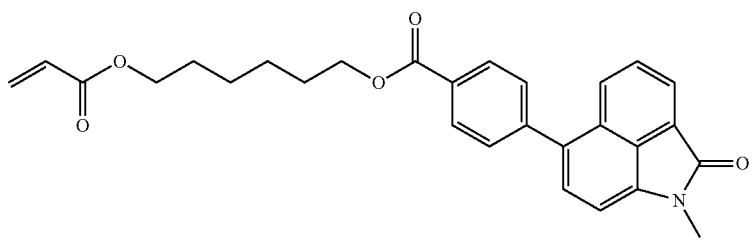

-continued
Compound B-34
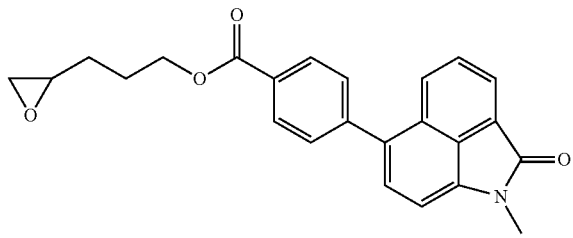
Compound B-35
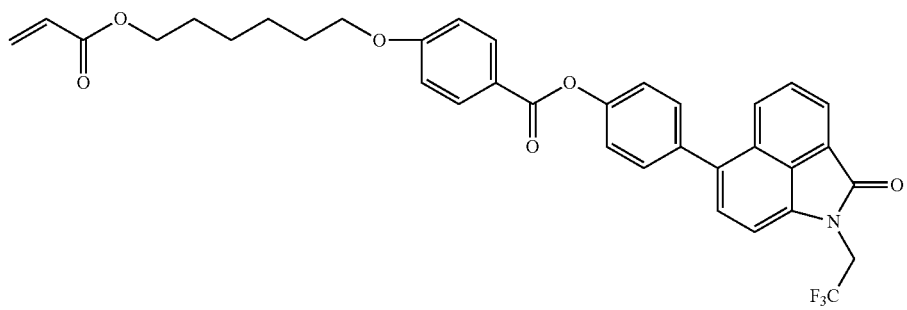
Compound B-36
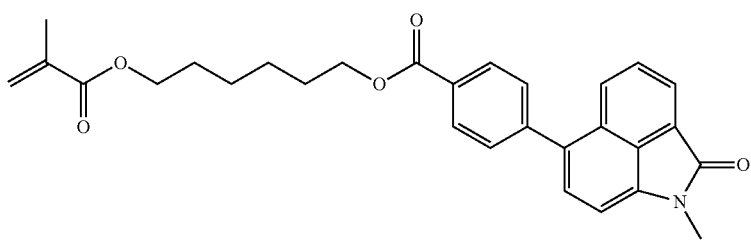
Compound B-37
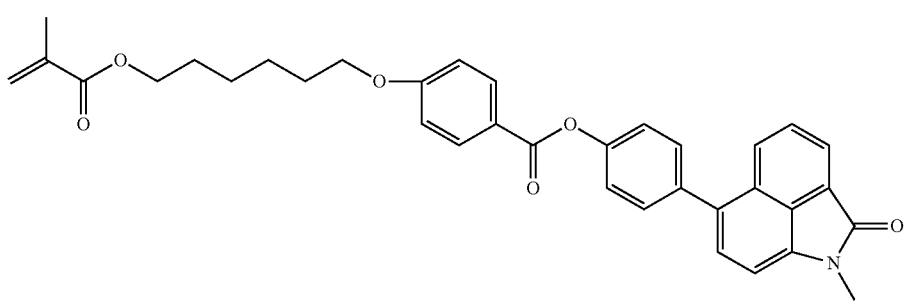
Compound B-38
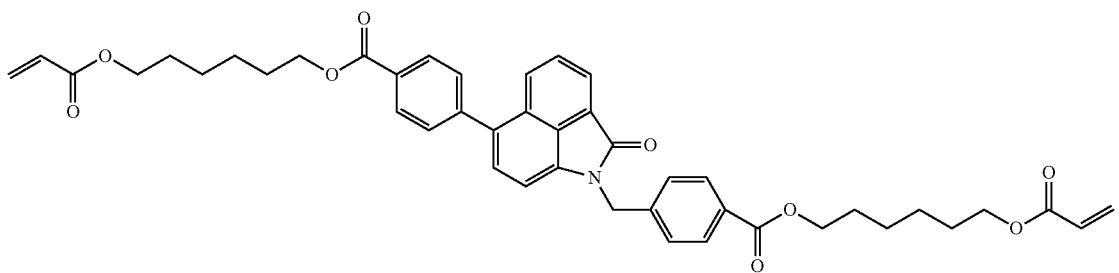

[Chemical Formula 40]
Compound B-39
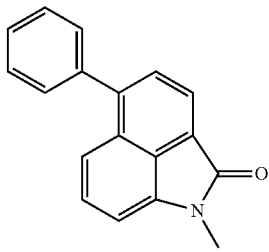
Compound B-40
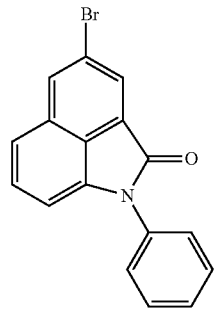
Compound B-41
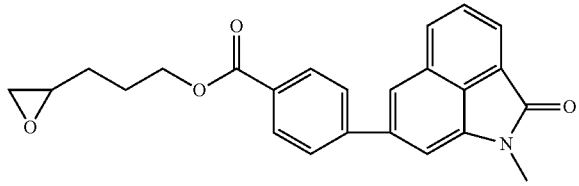
Compound B-42
Compound B-43
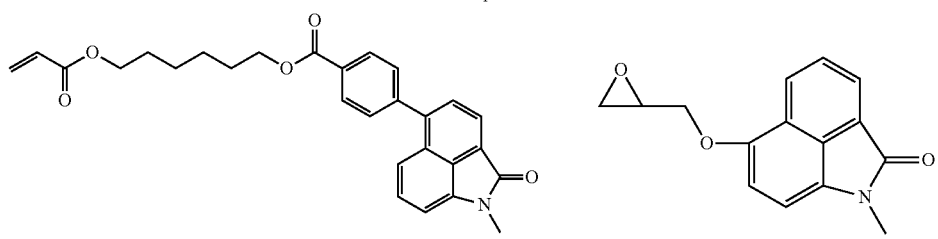
Compound B-44
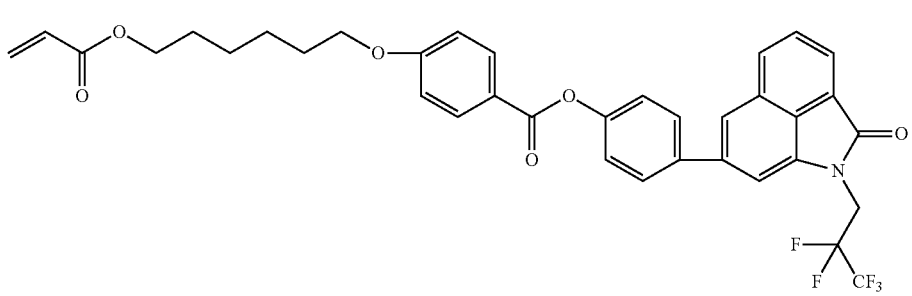
Compound B-45
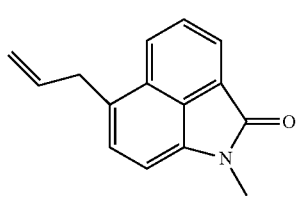

-continued
Compound B-46
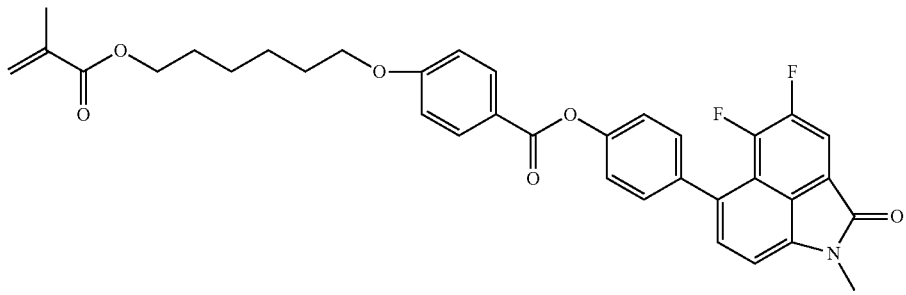
Compound B-47
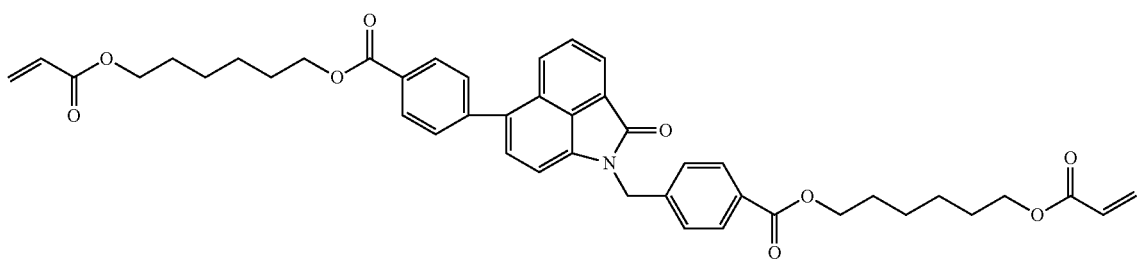
Compound B-48
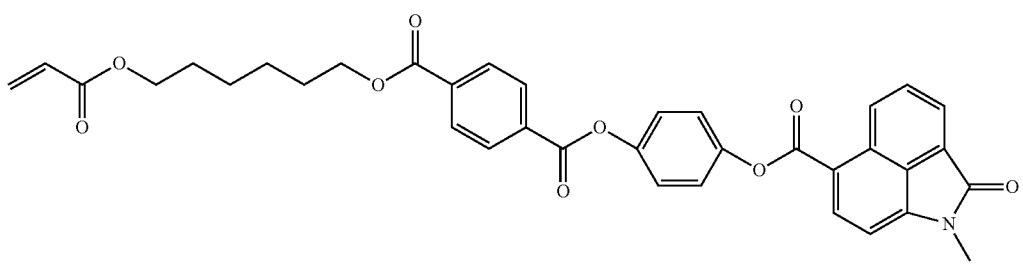
[Chemical Formula 41]
Compound B-49
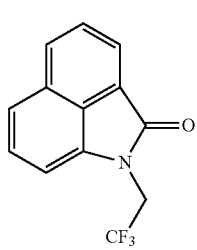
Compound B-50
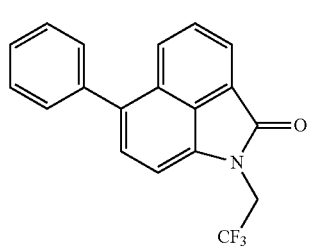
Compound B-51
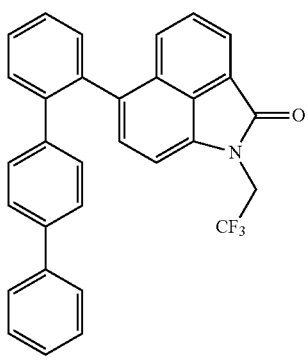
Compound B-52
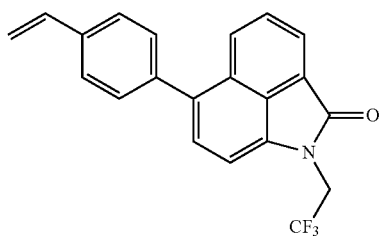

The method for producing the naphtholactam derivative represented by formula (IV) is not restricted. For example, the naphtholactam derivative represented by formula (IV) in which $R^8$ is represented by formula (V) can be produced according to methods used for the synthesis of common liquid crystal compounds, and more specifically can be produced according to scheme 1 or 2 shown below.

Although the schemes below show the synthesis of a naphtholactam derivative with a substituent of formula (V) in which ring $A^5$ is a benzene ring, $Z^6$ is a single bond, $Z^7$ is —COO—, and s is 1, other naphtholactam derivatives can also be produced in a similar manner according to the process shown below.

Scheme 1

[Chemical Formula 42]

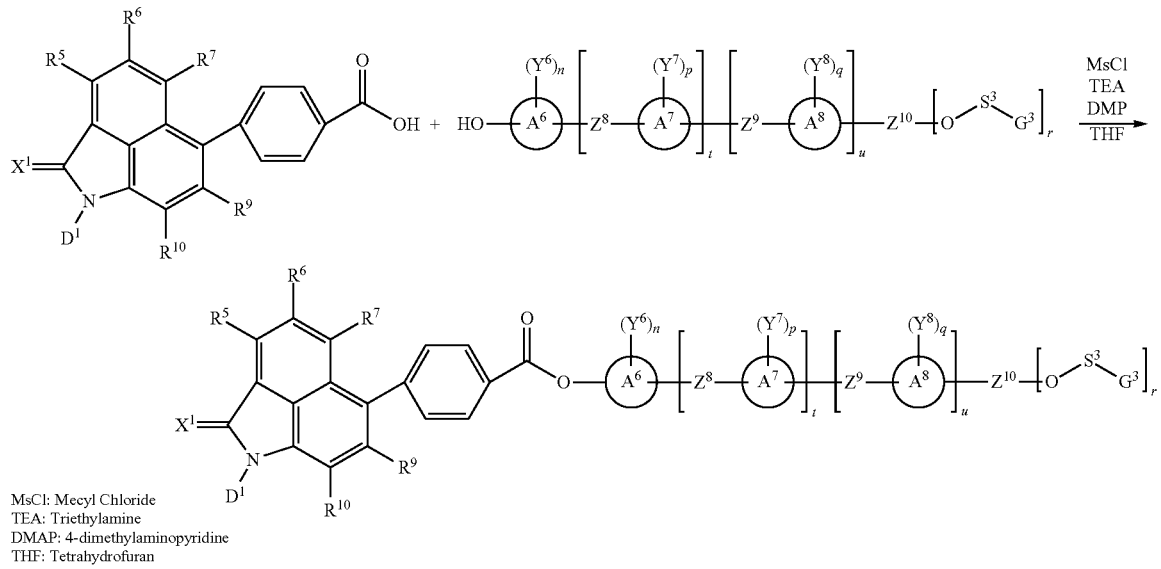

MsCl: Mecyl Chloride
TEA: Triethylamine
DMAP: 4-dimethylaminopyridine
THF: Tetrahydrofuran In the formula, $X^1$, $R^5$ to $R^7$, $R^9$, $R^{10}$, and $D^1$ are the same as defined in formula (IV), and $A^6$, $A^7$, $A^8$, $S^3$, $Z^8$, $Z^9$, $Z^{10}$, $Y^6$, $Y^7$, $Y^8$, n, p, q, t, u, r, and $G^3$ are the same as defined in formula (V).

Scheme 2

[Chemical Formula 43]

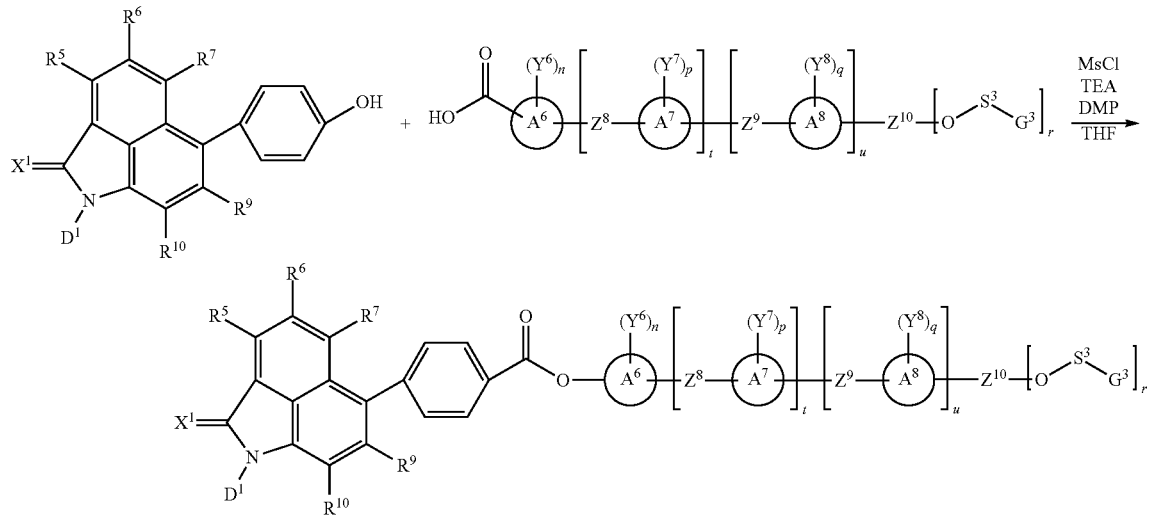

MsCl: Mecyl Chloride
TEA: Triethylamine
DMAP: 4-dimethylaminopyridine
THF: Tetrahydrofuran In the formula, $X^1$, $R^5$ to $R^7$, $R^9$, $R^{10}$, and $D^1$ are the same as defined in formula (IV), and $A^6$, $A^7$, $A^8$, $S^3$, $Z^8$, $Z^9$, $Z^{10}$, $Y^6$, $Y^7$, $Y^8$, n, p, q, t, u, r, and $G^3$ are the same as defined in formula (V).

In view of luminous efficiency, the dye compound is preferably a coumarin derivative (B-2). Examples of such a coumarin derivative include 7-hydroxycoumarin, 7-hydroxy-4-methylcoumarin (4-MU), 7-diethylamino-4-methylcoumarin (DAMC), coumarin 6, coumarin 120, and others such as coumarin derivatives represented by formula (VI) below. These compounds may be used alone or in any mixture. Among the coumarin derivatives, coumarin derivatives represented by formula (VI) are more preferred in term of luminous efficiency.

[Chemical Formula 44]

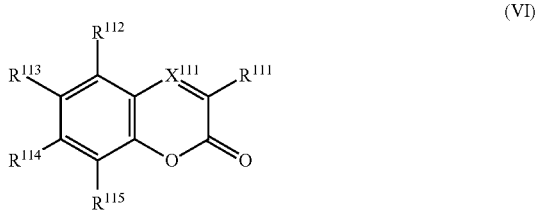

(VI)

wherein $X^{111}$ represents a nitrogen atom or $CR^{116}$, $R^{111}$ to $R^{116}$ each independently represent a hydrogen atom, a halogen atom, a nitro group, a cyano group, an aldehyde group, a carboxyl group, a hydroxyl group, —NRR', an organosilyl group, an optionally substituted alkyl group of 1 to 30 carbon atoms, an optionally substituted aryl group of 6 to 30 carbon atoms, an optionally substituted arylalkyl group of 7 to 30 carbon atoms, an optionally substituted heterocyclic group of 2 to 30 carbon atoms, or a substituent represented by formula (V) above, a methylene chain in the alkyl group or the arylalkyl group represented by each of $R^{111}$ to $R^{116}$ may be interrupted by —O—, —S—, —SO$_2$—, —CO—, —OCO—, or —COO—, the aryl group represented by each of $R^{111}$ to $R^{116}$ and the coumarin structure may be linked together via —O—, —S—, —SO$_2$—, —CO—, —OCO—, or —COO—, and the methylene chain may be replaced by —CH=CH— or —C≡C—, adjacent two or more of $R^{111}$ to $R^{116}$ may be linked together to form a ring, or when any one of $R^{111}$ to $R^{116}$ is —NRR', R or R' and any other one of $R^{111}$ to $R^{116}$ adjacent thereto may be linked together to form a ring, R and R' each independently represent a hydrogen atom, an optionally substituted alkyl group of 1 to 30 carbon atoms, or an optionally substituted aryl group of 6 to 30 carbon atoms, a methylene chain in the alkyl group represented by each of R and R' may be interrupted by —O—, —S—, —SO$_2$—, —CO—, —OCO—, or —COO—, the aryl group represented by each of R and R' and the coumarin structure may be linked together via —O—, —S—, —SO$_2$—, —CO—, —OCO—, or —COO—, and the methylene chain may be replaced by —C=C— or —C≡C—.

The alkyl group of 1 to 30 carbon atoms and the optionally substituted aryl group of 6 to 30 carbon atoms represented by each of $R^{111}$ to $R^{116}$, R, and R' in formula (VI); the halogen atom, the organosilyl group, the optionally substituted arylalkyl group of 7 to 30 carbon atoms, and the optionally substituted heterocyclic group of 2 to 30 carbon atoms represented by each of $R^{111}$ to $R^{116}$ in formula (VI); the optionally substituted alkyl group of 1 to 30 carbon atoms and the optionally substituted aryl group of 6 to 30 carbon atoms represented by each of $R^{111}$ to $R^{116}$, R, and R' in formula (VI); and the optionally substituted arylalkyl group of 7 to 30 carbon atoms and the optionally substituted heterocyclic group of 2 to 30 carbon atoms represented by each of $R^{111}$ to $R^{116}$ and $D^1$ may also each have a substituent(s), examples of which include those listed above for formula (IV).

Adjacent two or more of $R^{111}$ to $R^{116}$ may be linked together to form a ring, or when any one of $R^{111}$ to $R^{116}$ is —NRR', R or R' and any other one of $R^{111}$ to $R^{116}$ adjacent thereto may be linked together to form a ring, and examples of such a ring include five- to seven-membered rings such as a cyclopentane ring, a cyclohexane ring, a cyclopentene ring, a benzene ring, a piperidine ring, a morpholine ring, a lactone ring, a lactam ring, and a julolidine ring.

The coumarin derivative represented by formula (VI) is preferably such that at least one of $R^{111}$ to $R^{116}$, especially $R^{111}$, is a substituent represented by formula (V), because such a coumarin derivative has a structure having a ratio of its transverse length to its molecular main chain length of less than 1 and having high linearity, so that it can easily undergo molecular orientation and can emit polarized light with a high degree of polarization.

Besides the substituent represented by formula (V), the moiety represented by each of $R^{111}$ to $R^{116}$ is preferably a hydrogen atom, a halogen atom, a cyano group, an aldehyde group, a carboxyl group, —NRR', an organosilyl group, an alkyl group of 1 to 30 carbon atoms, an aryl group of 6 to 30 carbon atoms, an arylalkyl group of 7 to 30 carbon atoms, a heterocyclic group of 2 to 30 carbon atoms, a halogen-substituted alkyl group of 1 to 30 carbon atoms, an alkyl group of 1 to 30 carbon atoms with a methylene chain interrupted by —O—, an arylalkyl group of 7 to 30 carbon atoms with a methylene chain interrupted by —COO— or —OCO—, an arylalkyl group of 7 to 30 carbon atoms with a methylene chain replaced by —C≡C—, an alkyl- or phenyl-substituted heterocyclic group of 2 to 30 carbon atoms, a group including $R^{112}$ and $R^{113}$ moieties linked together to form a benzene ring, a group including $R^{114}$ and $R^{115}$ moieties linked together to form a benzene ring, or a group including $R^{113}$, $R^{114}$, and $R^{115}$ moieties linked together to form a julolidine ring.

In formula (V), rings $A^5$, $A^6$, $A^7$, and $A^8$ are preferably benzene or naphthalene rings because they can increase linearity, and $Z^6$, $Z^7$, $Z^8$, $Z^9$, and $Z^{10}$ are each preferably a direct bond, —O—CO—, or —CO—O— because raw materials for such moieties are easily available.

$G^3$ is preferably the group represented by formula (5) because in this case, the copolymerization with the polymerizable liquid crystal compound (A) will be easy.

Examples of the coumarin derivative represented by formula (VI) according to the invention include, but are not limited to, compounds B-101 to B-178 shown below.

[Chemical Formula 45]
Compound B-101
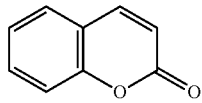
Compound B-102
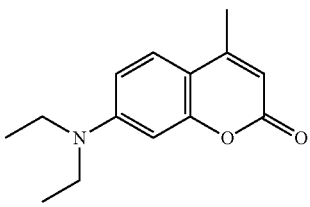
Compound B-103
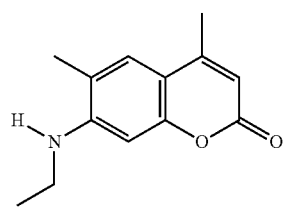
Compound B-104
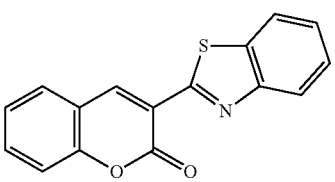
Compound B-105
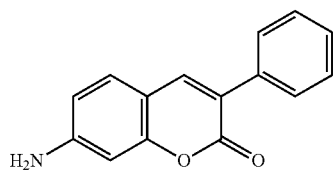
Compound B-106
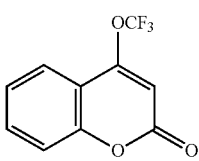
Compound B-107
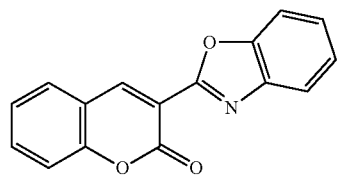
Compound B-108
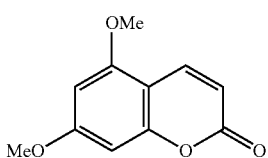
Compound B-109
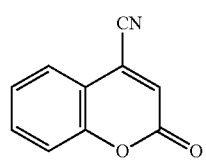
Compound B-110
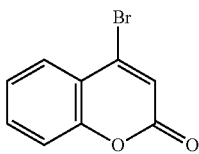
Compound B-111
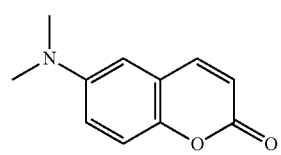
Compound B-112
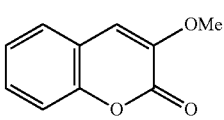
Compound B-113
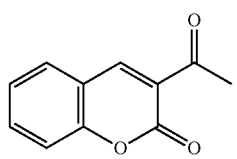
Compound B-114
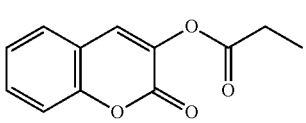

-continued
Compound B-115
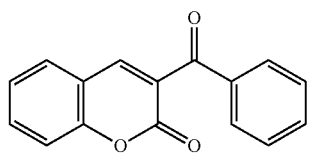
Compound B-116
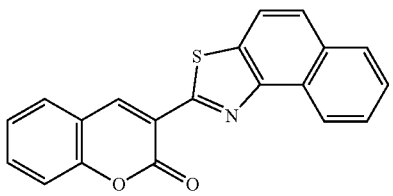
Compound B-117
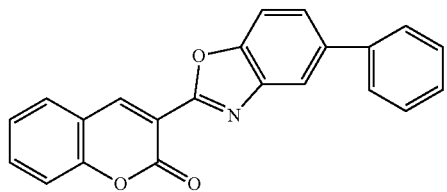
Compound B-118
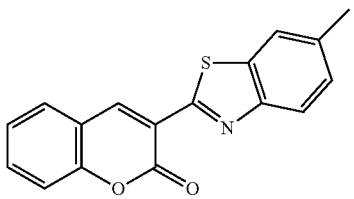
Compound B-119
[Chemical Formula 46]
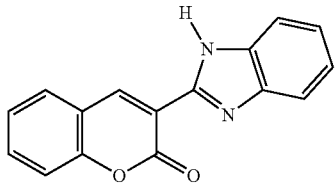
Compound B-120
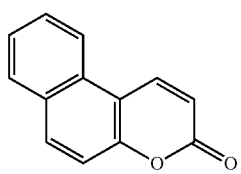
Compound B-121
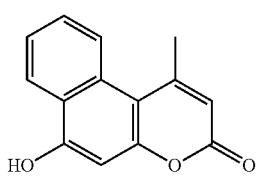
Compound B-122
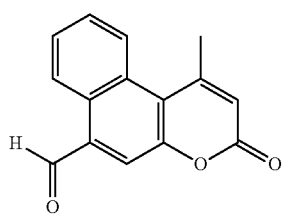
Compound B-123
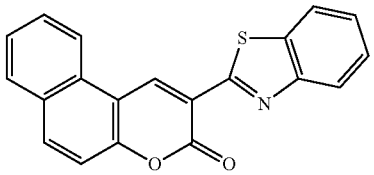
Compound B-124
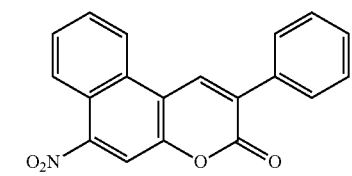
Compound B-125
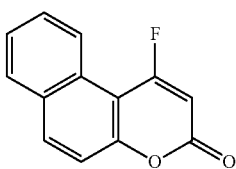
Compound B-126
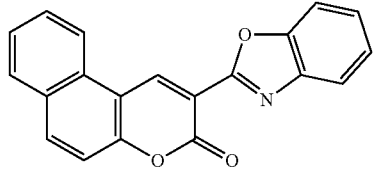
Compound B-127
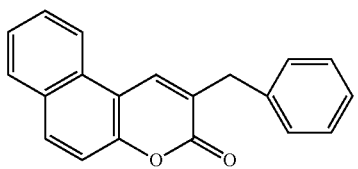

Compound B-128
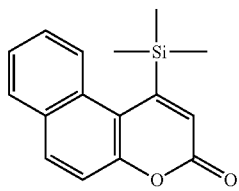
Compound B-129
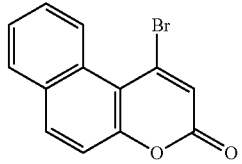
Compound B-130
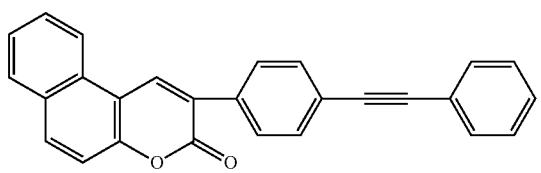
Compound B-131
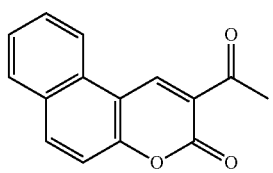
Compound B-132
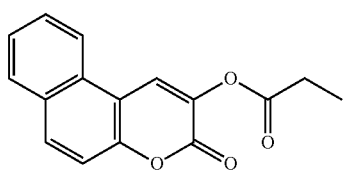
Compound B-133
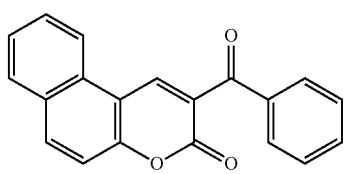
Compound B-134
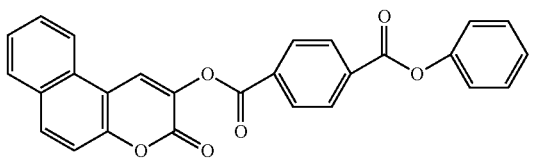
Compound B-135
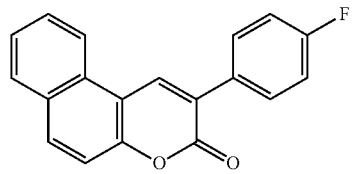
[Chemical Formula 47]
Compound B-136
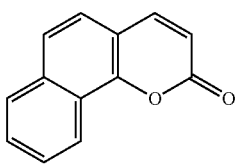
Compound B-137
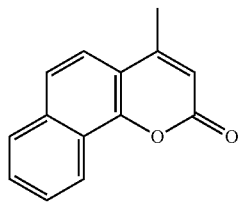
Compound B-138
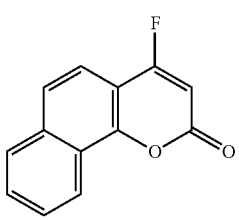
Compound B-139
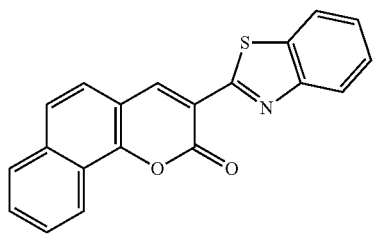

Compound B-140
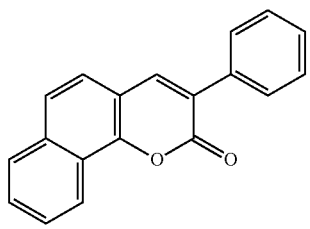
Compound B-141
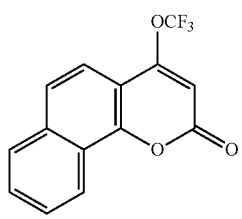
Compound B-142
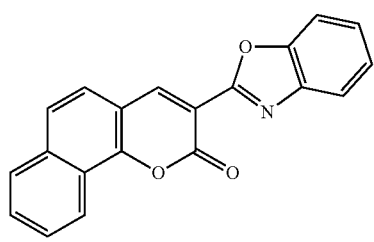
Compound B-143
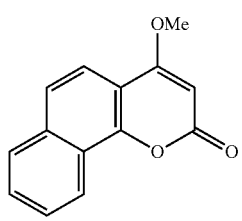
Compound B-144
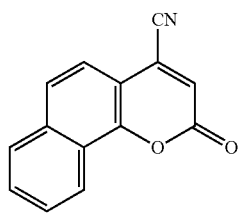
Compound B-145
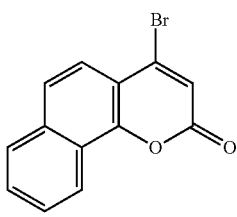
Compound B-146
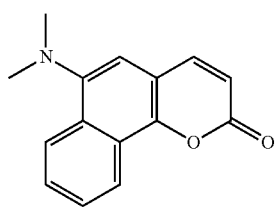
Compound B-147
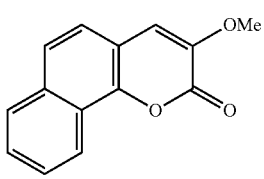
Compound B-148
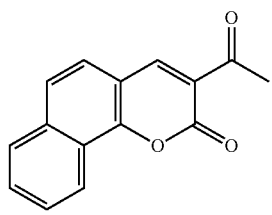
Compound B-149
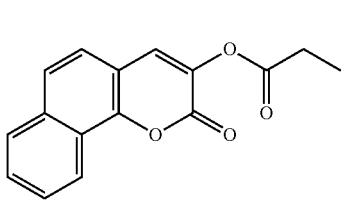
Compound B-150
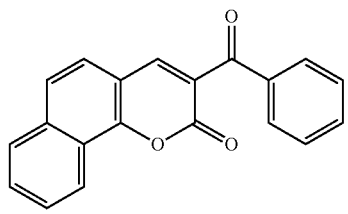
Compound B-151
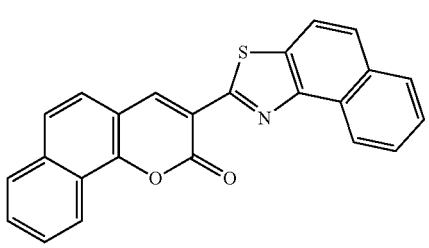

-continued
Compound B-152
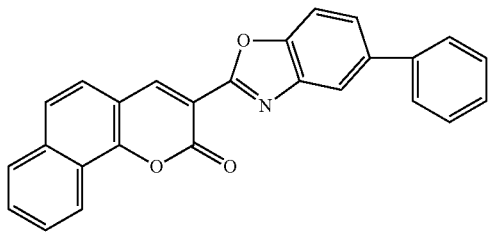
[Chemical Formula 48]
Compound B-153
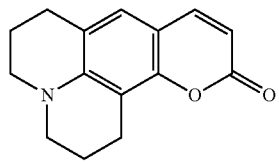
Compound B-154
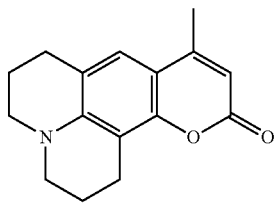
Compound B-155
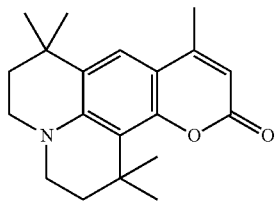
Compound B-156
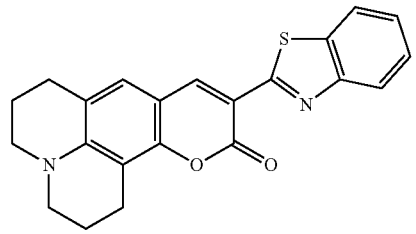
Compound B-157
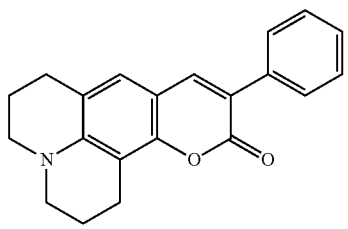
Compound B-158
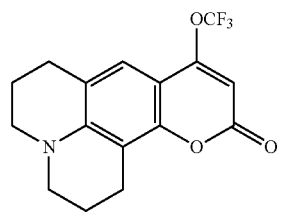
Compound B-159
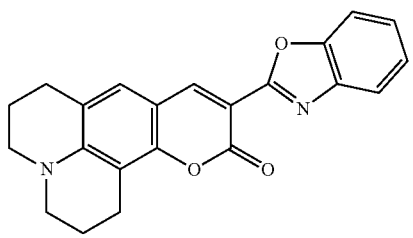
Compound B-160
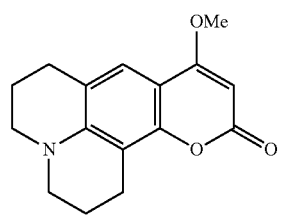
Compound B-161
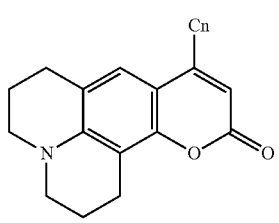
Compound B-162
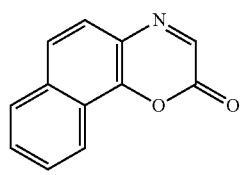

Compound B-163
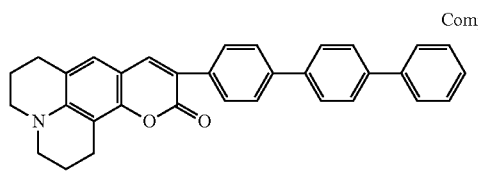
Compound B-164
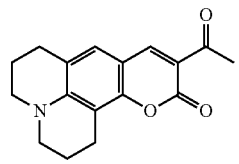
Compound B-165
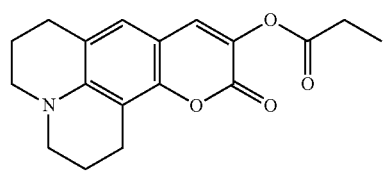
Compound B-166
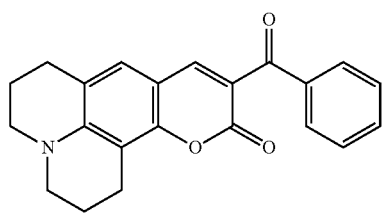
Compound B-167
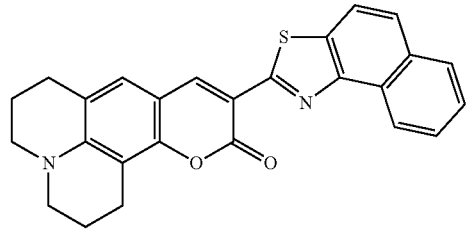
Compound B-168
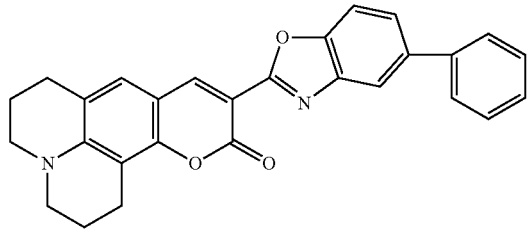
[Chemical Formula 49]
Compound B-169
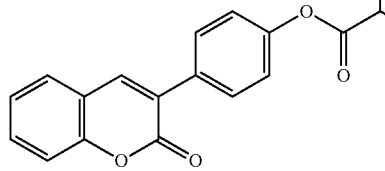
Compound B-170
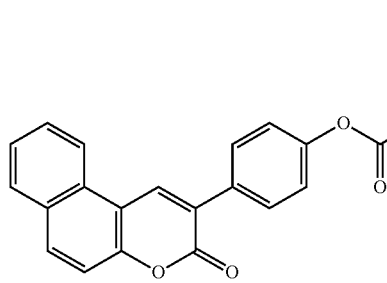
Compound B-171
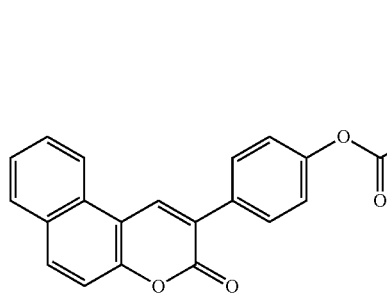

Compound B-172
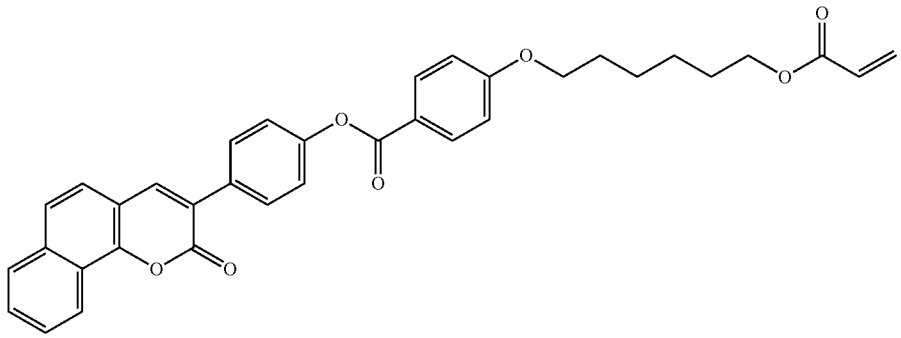
Compound B-173
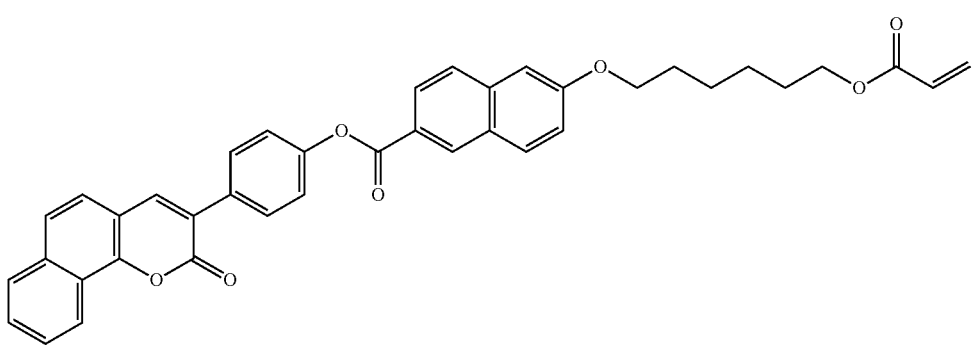
[Chemical Formula 50]
Compound B-174
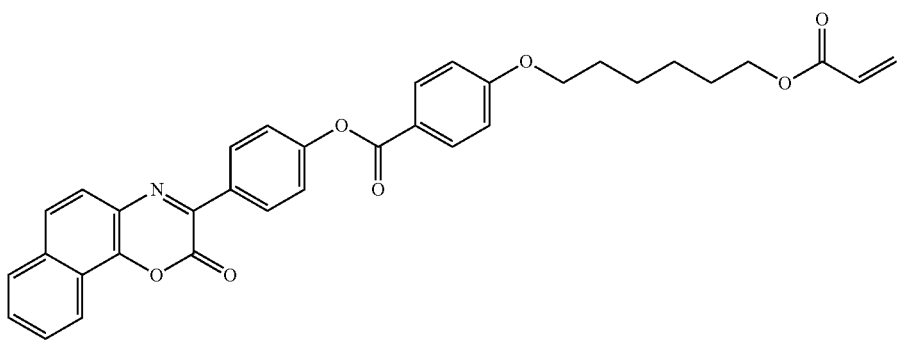
Compound B-175
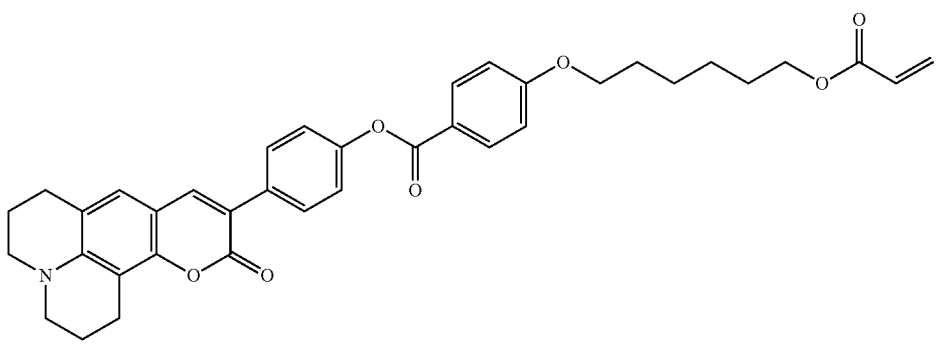

Compound B-176

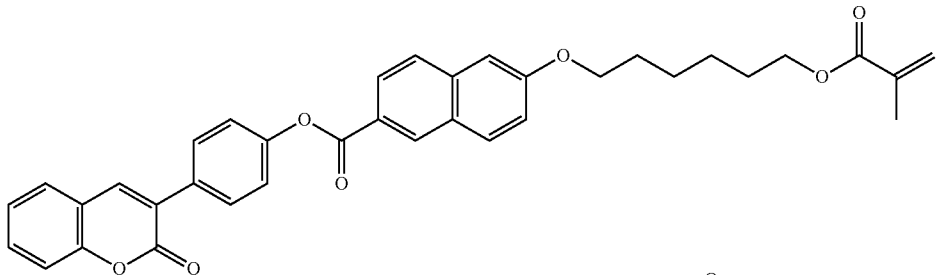

Compound B-177

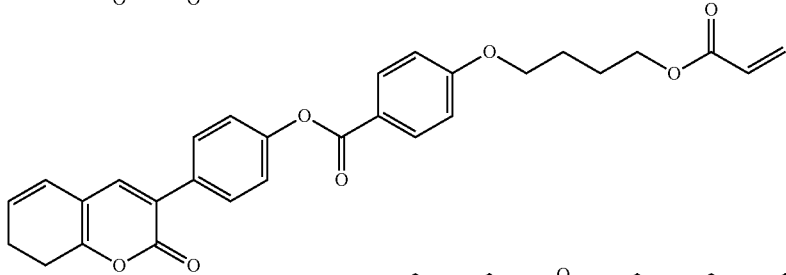

Compound B-178

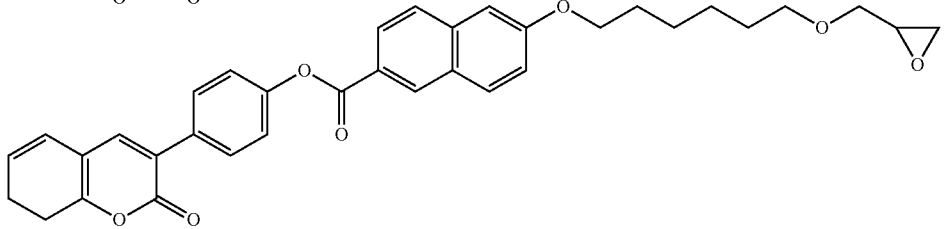

The method for producing the coumarin derivative represented by formula (VI) is not restricted. For example, the coumarin derivative represented by formula (VI) in which $R^{111}$ is represented by formula (V) can be produced according to methods used for the synthesis of common liquid crystal compounds, and more specifically can be produced according to scheme 1 or 2 shown below. Although the schemes below show the synthesis of a coumarin derivative with a substituent of formula (V) in which ring $A^5$ is a benzene ring, $Z^6$ is a single bond, $Z^7$ is —COO—, and s is 1, other coumarin derivatives can also be produced in a similar manner according to the process shown below.

Scheme 1

[Chemical Formula 51]

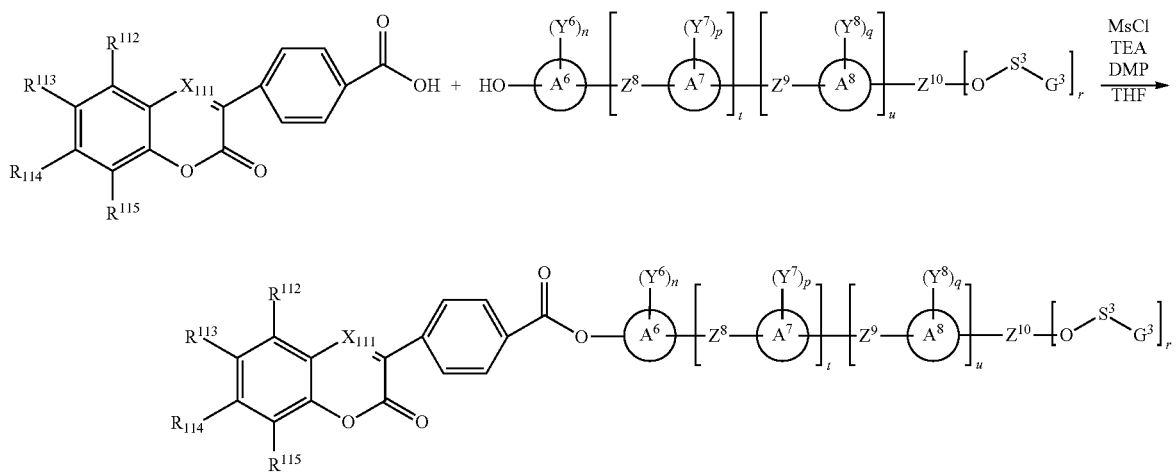

MsCl: Mecyl Chloride
TEA: Triethylamine
DMAP: 4-dimethylaminopyridine
THF: Tetrahydrofuran In the formula, $X^{111}$ and $R^{112}$ to $R^{115}$ are the same as defined in formula (VI), and $A^6$, $A^7$, $A^8$, $S^3$, $Z^8$, $Z^9$, $Z^{10}$, $Y^6$, $Y^7$, $Y^8$, n, p, q, t, u, r, and $G^3$ are the same as defined in formula (V).

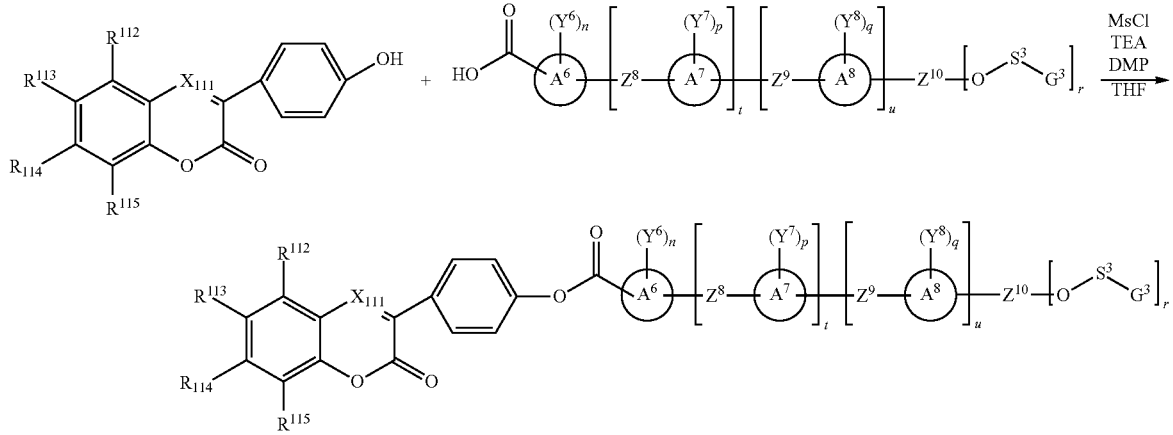

Scheme 2

[Chemical Formula 52]

MsCl: Mecyl Chloride
TEA: Triethylamine
DMAP: 4-dimethylaminopyridine
THF: Tetrahydrofuran In the formula, $X^{111}$ and $R^{112}$ to $R^{115}$ are the same as defined in formula (VI), and $A^6$, $A^7$, $A^8$, $S^3$, $Z^8$, $Z^9$, $Z^{10}$, $Y^6$, $Y^7$, $Y^8$, n, p, q, t, u, r, and $G^3$ are the same as defined in formula (V).

In view of luminous efficiency, the dye compound is preferably a Nile Red derivative (B-3). Examples of such a Nile Red derivative include 6-trifluoromethyl Nile Red, 6-perfluoroethyl Nile Red, 6-perfluoropropyl Nile Red, 6-perfluorobutyl Nile Red, 6-perfluoropentyl Nile Red, 6-perfluorohexyl Nile Red, 6-perfluoroheptyl Nile Red, 6-perfluorooctyl Nile Red, 6-perfluorononyl Nile Red, 6-perfluorodecyl Nile Red, 6-(2,4-bis(trifluoromethyl)phenyl) Nile Red, and others such as Nile Red derivatives represented by formula (VII) below. These compounds may be used alone or in any mixture. Among the Nile Red derivatives, Nile Red derivatives represented by formula (VII) are preferred in term of luminous efficiency.

[Chemical Formula 53]

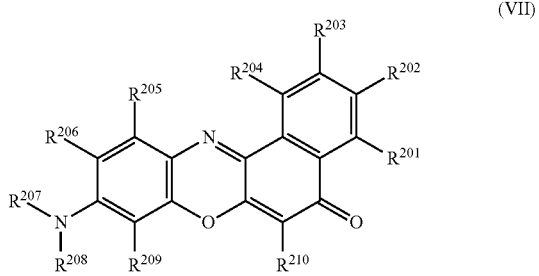

(VII)

wherein
$R^{201}$ to $R^{206}$, $R^{209}$, and $R^{210}$ each independently represent a hydrogen atom, a halogen atom, a nitro group, a cyano group, an aldehyde group, a carboxyl group, a hydroxyl group, —NRR', an organosilyl group, an optionally substituted alkyl group of 1 to 30 carbon atoms, an optionally substituted aryl group of 6 to 30 carbon atoms, an optionally substituted arylalkyl group of 7 to 30 carbon atoms, an optionally substituted heterocyclic group of 2 to 30 carbon atoms, or a substituent represented by formula (V) above, a methylene chain in the alkyl group or the arylalkyl group represented by each of $R^{201}$ to $R^{206}$, $R^{209}$, and $R^{210}$ may be interrupted by —O—, —S—, —SO$_2$—, —CO—, —OCO—, or —COO—, the aryl group represented by each of $R^{201}$ to $R^{206}$, $R^{209}$, and $R^{210}$ and the Nile Red structure may be linked together via —O—, —S—, —SO$_2$—, —CO—, —OCO—, or —COO—, and the methylene chain may be replaced by —CH=CH— or —C≡C—, adjacent two or more of $R^{201}$ to $R^{206}$ may be linked together to form a ring, or when any one of $R^{201}$ to $R^{206}$ is —NRR', R or R' and any other one of $R^{201}$ to $R^{206}$ adjacent thereto may be linked together to form a ring, $R^{207}$ and $R^{208}$ each independently represent an alkyl group of 1 to 10 carbon atoms, R and R' each independently represent a hydrogen atom, an optionally substituted alkyl group of 1 to 30 carbon atoms, or an optionally substituted aryl group of 6 to 30 carbon atoms, a methylene chain in the alkyl group represented by each of R and R' may be interrupted by —O—, —S—, —SO$_2$—, —CO—, —OCO—, or —COO—, the aryl group represented by each of R and R' and the Nile Red structure may be linked together via —O—, —S—, —SO$_2$—, —CO—, —OCO—, or —COO—, and the methylene chain may be replaced by —C=C— or —C≡C—.

Examples of the alkyl group of 1 to 10 carbon atoms represented by each of $R^{207}$ and $R^{208}$ in formula (VII) include those of 1 to 10 carbon atoms listed above for the alkyl group of 1 to 30 carbon atoms in formula (IV).

The optionally substituted alkyl group of 1 to 30 carbon atoms and the aryl group of 6 to 30 carbon atoms represented by each of $R^{201}$ to $R^{206}$, $R^{209}$, $R^{210}$, R, and R'; the halogen atom, the organosilyl group, the optionally substituted arylalkyl group of 7 to 30 carbon atoms, and the optionally substituted heterocyclic group of 2 to 30 carbon atoms represented by each of $R^{201}$ to $R^{206}$, $R^{209}$, and $R^{210}$; the optionally substituted alkyl group of 1 to 30 carbon atoms and the optionally substituted aryl group of 6 to 30 carbon atoms represented by each of $R^{201}$ to $R^{206}$, $R^{209}$, $R^{210}$, R, and R' in formula (VII); and the optionally substituted arylalkyl group of 7 to 30 carbon atoms and the optionally substituted heterocyclic group of 2 to 30 carbon atoms represented by each of $R^{201}$ to $R^{206}$, $R^{209}$, and $R^{210}$ may also each have a substituent(s), examples of which include those listed above for formula (IV).

Adjacent two or more of $R^{201}$ to $R^{206}$ may also be linked together to form a ring, or when any one of $R^{201}$ to $R^{206}$ is —NRR', R or R' and any other one of $R^{201}$ to $R^{206}$ adjacent thereto may also be linked together to form a ring, and examples of such a ring include those listed above for formula (V).

The Nile Red derivative represented by formula (VII) is preferably such that at least one of $R^{201}$ to $R^{206}$, $R^{209}$, and $R^{210}$, especially $R^{202}$, is a substituent represented by formula (V), because such a Nile Red derivative has a structure having a ratio of its transverse length to its molecular main chain length of less than 1 and having high linearity, so that it can easily undergo molecular orientation and can emit polarized light with a high degree of polarization.

Besides the substituent represented by formula (V), the moiety represented by each of $R^{201}$ to $R^{206}$, $R^{209}$, and $R^{210}$ is preferably a hydrogen atom, a halogen atom, a cyano group, —NRR', an organosilyl group, an alkyl group of 1 to 30 carbon atoms, an aryl group of 6 to 30 carbon atoms, an arylalkyl group of 7 to 30 carbon atoms, a heterocyclic group of 2 to 30 carbon atoms, an alkyl group of 1 to 30 carbon atoms with a methylene chain interrupted by —O—, a halogen-substituted alkyl group of 1 to 30 carbon atoms, a cyano-substituted arylalkyl group of 7 to 30 carbon atoms, or an alkyl group of 1 to 30 carbon atoms with a methylene chain replaced by —C=C—, because raw materials for such moieties are easily available.

In formula (V), rings $A^5$, $A^6$, $A^7$, and $A^8$ are preferably benzene or naphthalene rings because they can increase linearity, and $Z^6$, $Z^7$, $Z^8$, $Z^9$, and $Z^{10}$ are each preferably a direct bond, —O—CO—, or —CO—O— because raw materials for such moieties are easily available.

$G^3$ is preferably the group represented by formula (5) because in this case, the copolymerization with the polymerizable liquid crystal compound (A) will be easy.

Examples of the Nile Red derivative represented by formula (VII) according to the invention include, but are not limited to, compounds B-201 to B-225 shown below.

[Chemical Formula 54]

Compound B-201

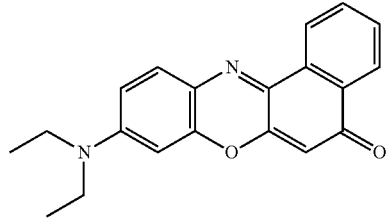

Compound B-202

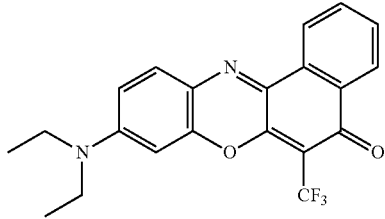

Compound B-203

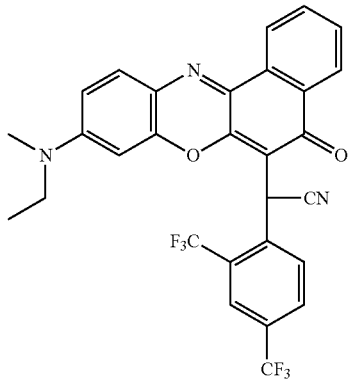

Compound B-204

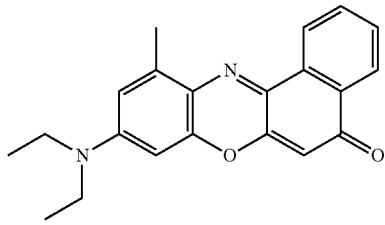

Compound B-205

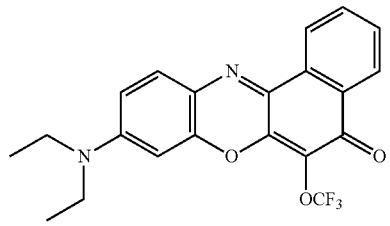

Compound B-206

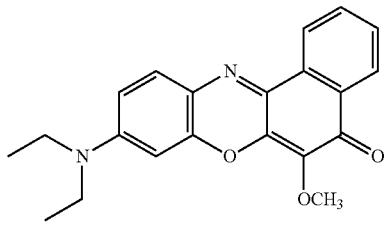

-continued
Compound B-207
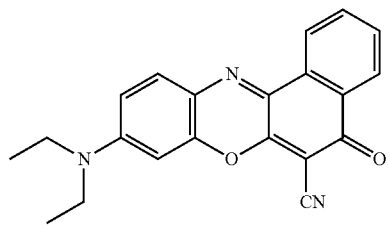
Compound B-208
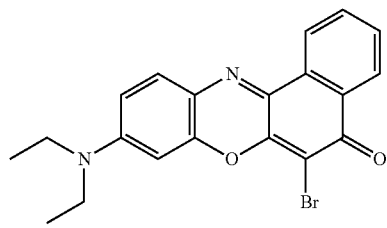
Compound B-209
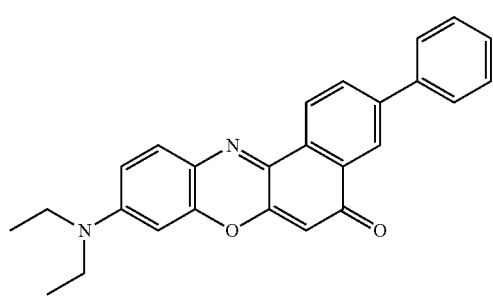
Compound B-210
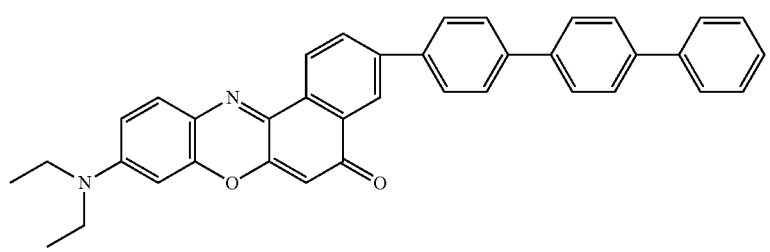
[Chemical Formula 55]
Compound B-211
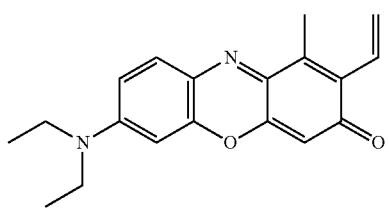
Compound B-212
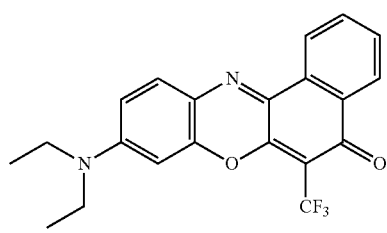
Compound B-213
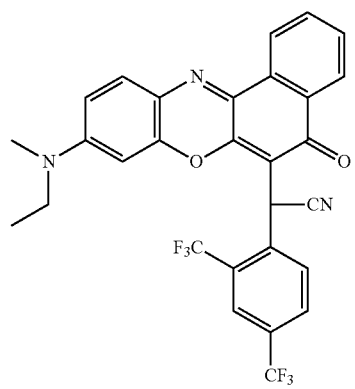
Compound B-214
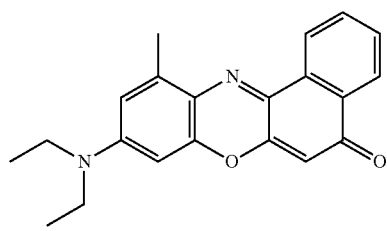

-continued
Compound B-215
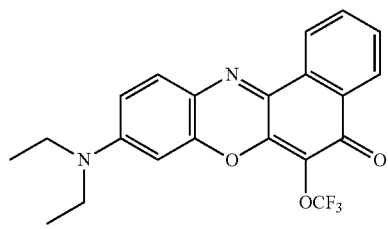
Compound B-216
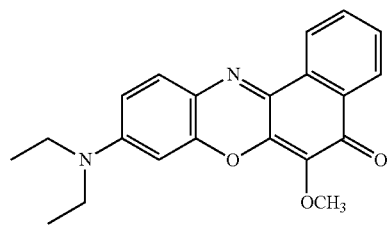
Compound B-217
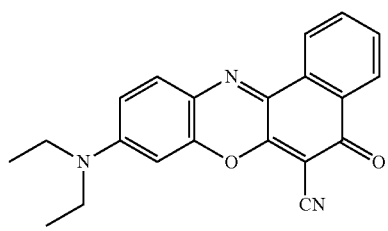
Compound B-218
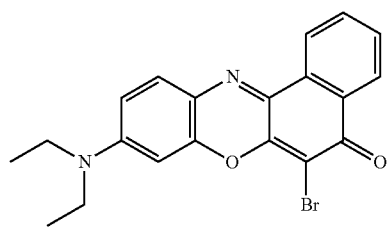
Compound B-219
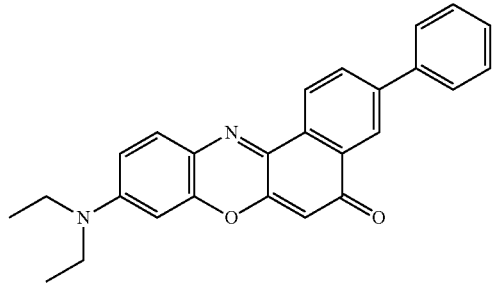
Compound B-220
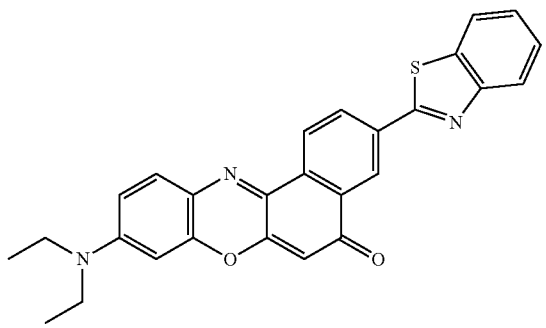
[Chemical Formula 56]
Compound B-221
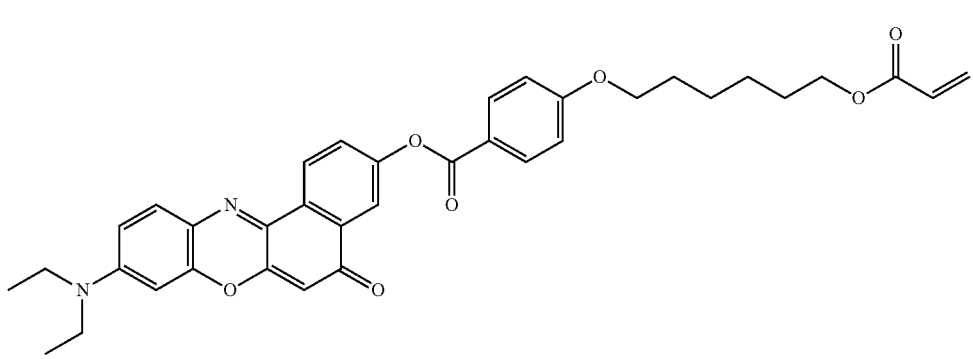

-continued

Compound B-222
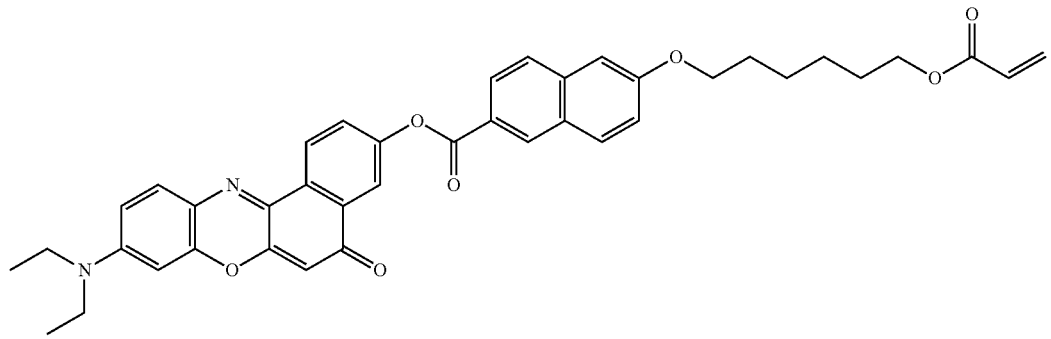

Compound B-223
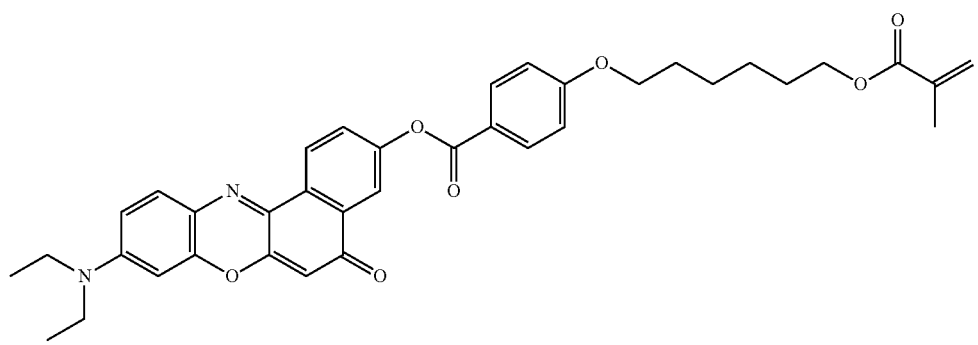

Compound B-224
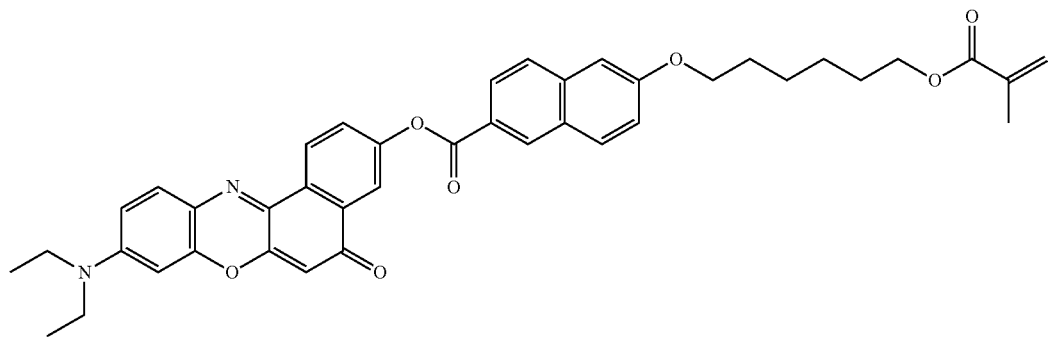

Compound B-225
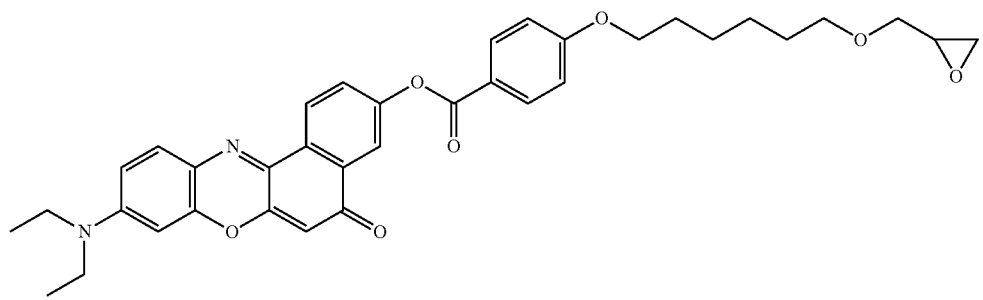

The method for producing the Nile Red derivative represented by formula (VII) is not restricted. For example, the Nile Red derivative represented by formula (VII) in which $R^{202}$ is represented by formula (V) can be produced according to methods used for the synthesis of common liquid crystal compounds, and more specifically can be produced according to scheme 1 or 2 shown below. Although the schemes below show the synthesis of a Nile Red derivative with a substituent of formula (V) in which ring $A^5$ is a benzene ring, $Z^6$ is a single bond, $Z^7$ is —COO—, and s is 1, other Nile Red derivatives can also be produced in a similar manner according to the process shown below.

Scheme 1
[Chemical Formula 57]
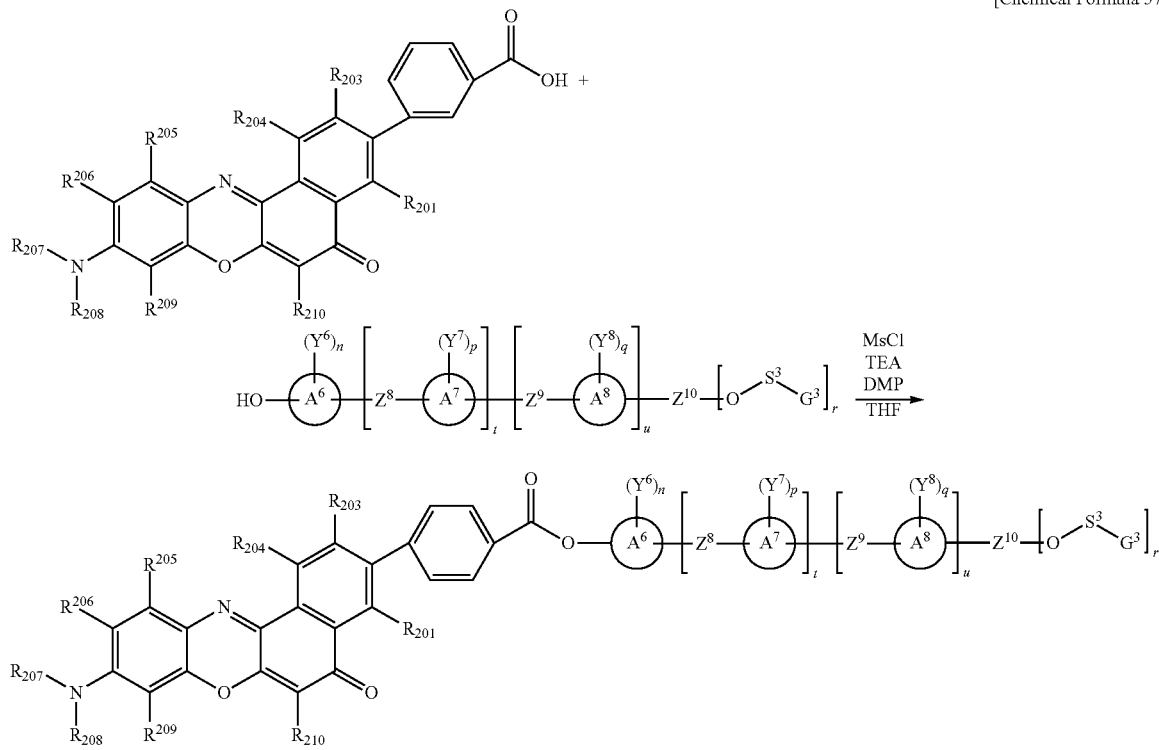
MsCl: Mecyl Chloride
TEA: Triethylamine
DMAP: 4-dimethylaminopyridine
THF: Tetrahydrofuran
In the formula, $R^{201}$ and $R^{203}$ to $R^{210}$ are the same as defined in formula (VII), and $A^6$, $A^7$, $A^8$, $S^3$, $Z^8$, $Z^9$, $Z^{10}$, $Y^6$, $Y^7$, $Y^8$, n, p, q, t, u, r, and $G^3$ are the same as defined in formula (V).
Scheme 2
[Chemical Formula 58]
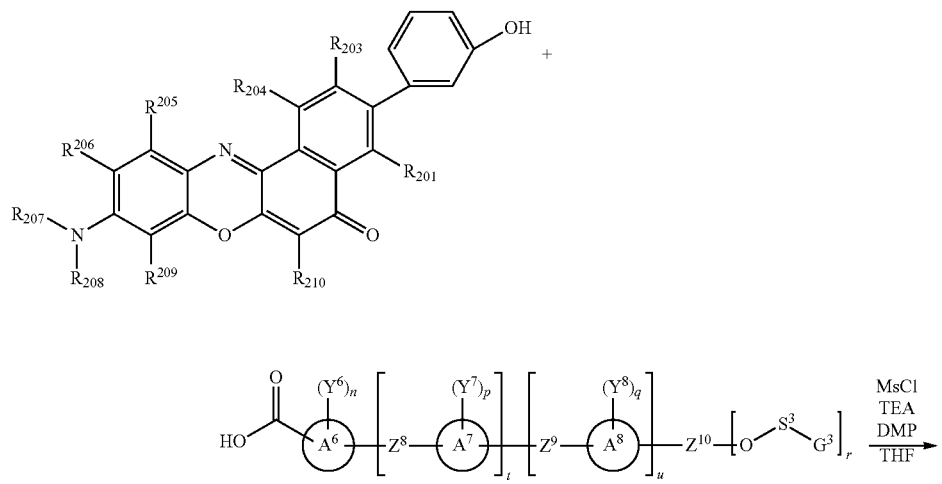

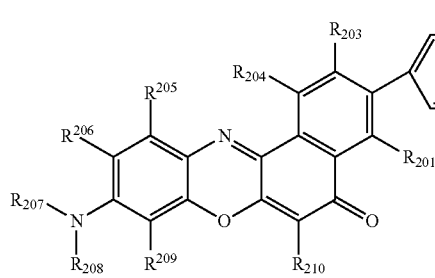
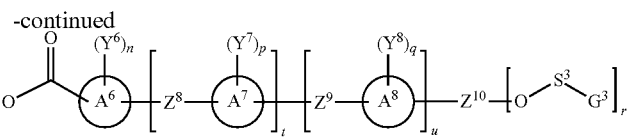

MsCl: Mecyl Chloride
TEA: Triethylamine
DMAP: 4-dimethylaminopyridine
THF: Tetrahydrofuran In the formula, $R^{14}$, $R^{16}$ to $R^{20}$, and $R^{37}$ to $R^{39}$ are the same as defined in formula (VII), and $A^6$, $A^7$, $A^8$, $S^3$, $Z^8$, $Z^9$, $Z^{10}$, $Y^6$, $Y^7$, $Y^8$, p, q, t, u, r, and $G^3$ are the same as defined in formula (V).

In view of luminous efficiency, the dye compound is preferably an anthracene derivative (B-4). Examples of such an anthracene derivative include 9-(4-diethylaminostyryl)-10-(4-nitrostyryl)anthracene, 9,10-bis(phenylethynyl)anthracene, 9,10-bis(diphenylamino)anthracene, 9,10-dimethylanthracene, 9,10-diphenylanthracene, 9,10-bis[4-(diphenylamino)styryl]anthracene, and others such as anthracene derivatives represented by formula (VIII) below. These compounds may be used alone or in any mixture. Among the anthracene derivatives, anthracene derivatives represented by formula (VIII) are preferred in term of luminous efficiency.

[Chemical Formula 59]

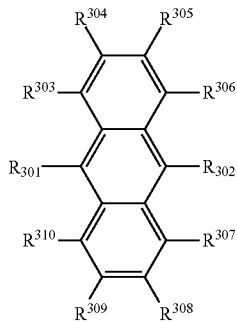

(VIII)

wherein $R^{301}$ to $R^{310}$ each independently represent a hydrogen atom, a halogen atom, a nitro group, a cyano group, an aldehyde group, a carboxyl group, a hydroxyl group, —NRR', an organosilyl group, an optionally substituted alkyl group of 1 to 30 carbon atoms, an optionally substituted aryl group of 6 to 30 carbon atoms, an optionally substituted arylalkyl group of 7 to 30 carbon atoms, an optionally substituted heterocyclic group of 2 to 30 carbon atoms, a substituent represented by formula (V) above, or a substituent represented by formula (IX), and at least one of $R^{301}$ to $R^{310}$ represents a substituent represented by formula (IX), a methylene chain in the alkyl group or the arylalkyl group represented by each of $R^{301}$ to $R^{310}$ may be interrupted by —O—, —S—, —SO$_2$—, —CO—, —OCO—, or —COO—, the aryl group represented by each of $R^{301}$ to $R^{310}$ and the anthracene structure may be linked together via —O—, —S—, —SO$_2$—, —CO—, —OCO—, or —COO—, and the methylene chain may be replaced by —CH=CH— or —C≡C—, adjacent two or more of $R^{301}$ to $R^{310}$ may be linked together to form a ring, or when any one of $R^{301}$ to $R^{310}$ is —NRR', R or R' and any other one of $R^{301}$ to $R^{310}$ adjacent thereto may be linked together to form a ring, R and R' each independently represent a hydrogen atom, an optionally substituted alkyl group of 1 to 30 carbon atoms, or an optionally substituted aryl group of 6 to 30 carbon atoms, a methylene chain in the alkyl group represented by each of R and R' may be interrupted by —O—, —S—, —SO$_2$—, —CO—, —OCO—, or —COO—, the aryl group represented by each of R and R' and the anthracene structure may be linked together via —O—, —S—, —SO$_2$—, —CO—, —OCO—, or —COO—, and the methylene chain may be replaced by —C=C— or —C≡C—, wherein formula (IX) is the following:

[Chemical Formula 60]

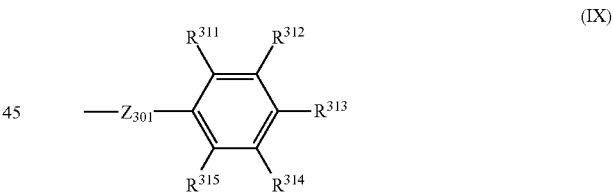

(IX)

wherein $Z^{301}$ represents a single bond, an alkylene group of 1 to 4 carbon atoms, —O—, —S—, —SO$_2$—, —CO—, —OCO—, —COO—, —CH=CH—, or —C≡C—, $R^{311}$ to $R^{315}$ each independently represent a hydrogen atom, a halogen atom, a nitro group, a cyano group, an aldehyde group, a carboxyl group, a hydroxyl group, —NRR', an organosilyl group, an optionally substituted alkyl group of 1 to 30 carbon atoms, an optionally substituted aryl group of 6 to 30 carbon atoms, an optionally substituted arylalkyl group of 7 to 30 carbon atoms, an optionally substituted heterocyclic group of 2 to 30 carbon atoms, or a substituent represented by formula (V) above, and R and R' each independently represent a hydrogen atom, an optionally substituted alkyl group of 1 to 30 carbon atoms, or an optionally substituted aryl group of 6 to 30 carbon atoms.

The optionally substituted alkyl group of 1 to 30 carbon atoms or the optionally substituted aryl group of 6 to 30 carbon atoms represented by each of $R^{301}$ to $R^{310}$, R, and R' in formula (VIII); the halogen atom, the organosilyl group, the optionally substituted arylalkyl group of 7 to 30 carbon atoms, and the optionally substituted heterocyclic group of 2 to 30 carbon atoms represented by each of $R^{301}$ to $R^{310}$; the optionally substituted alkyl group of 1 to 30 carbon atoms and the optionally substituted aryl group of 6 to 30 carbon atoms represented by each of $R^{301}$ to $R^{310}$, R, and R' in formula (VIII); and the optionally substituted arylalkyl group of 7 to 30 carbon atoms and the optionally substituted heterocyclic group of 2 to 30 carbon atoms represented by each of $R^{301}$ to $R^{310}$ may also each have a substituent(s), examples of which include those listed above for formula (IV).

Examples of the alkylene group of 1 to 4 carbon atoms represented by $Z^{301}$ in formula (IX) include those of 1 to 4 carbon atoms listed above for the alkylene group of 1 to 8 carbon atoms represented by each of $S^1$ and $S^2$ in formula (I).

The optionally substituted alkyl group of 1 to 30 carbon atoms or the optionally substituted aryl group of 6 to 30 carbon atoms represented by each of $R^{311}$ to $R^{315}$, R, and R'; the halogen atom, the organosilyl group, the arylalkyl group of 7 to 30 carbon atoms, and the optionally substituted heterocyclic group of 2 to 30 carbon atoms represented by each of $R^{311}$ to $R^{315}$; the optionally substituted alkyl group of 1 to 30 carbon atoms and the optionally substituted aryl group of 6 to 30 carbon atoms represented by each of $R^{311}$ to $R^{315}$, R, and R' in formula (VIII); and the optionally substituted arylalkyl group of 7 to 30 carbon atoms and the optionally substituted heterocyclic group of 2 to 30 carbon atoms represented by each of $R^{311}$ to $R^{315}$ may also each have a substituent(s), examples of which include those listed above for formula (IV).

The anthracene derivative represented by formula (VIII) is preferably such that at least one of $R^{301}$ to $R^{310}$, especially $R_{301}$ or $R_{302}$, is a substituent represented by formula (V) or at least one of $R^{301}$ to $R^{310}$, especially $R_{301}$ or $R_{302}$, is a substituent represented by formula (IX) and $R^{313}$ in formula (IX) is represented by formula (V), because such an anthracene derivative has a structure having a ratio of its transverse length to its molecular main chain length of less than 1 and having high linearity, so that it can easily undergo molecular orientation and can emit polarized light with a high degree of polarization.

Besides the substituent represented by formula (V), the moiety represented by each of $R^{301}$ to $R^{310}$ in formula (VIII) or the moiety represented by each of $R^{311}$ to $R^{315}$ in formula (IX) is preferably a hydrogen atom, a hydroxyl group, a nitro group, —NRR', an alkyl group of 1 to 30 carbon atoms, an aryl group of 6 to 30 carbon atoms, or an alkyl group of 1 to 30 carbon atoms with a methylene chain interrupted by —O—, because raw materials for such moieties are easily available.

In formula (IX), $Z^{301}$ is preferably a direct bond or —C≡C—.

In formula (V), rings $A^5$, $A^6$, $A^7$, and $A^8$ are preferably benzene or naphthalene rings, in particular, preferably benzene rings, because they can increase linearity, and $G^3$ is preferably the group represented by formula (5) because in this case, the copolymerization with the polymerizable liquid crystal compound (A) will be easy.

$Z^6$, $Z^7$, $Z^8$, $Z^9$, and $Z^{10}$ are preferably a direct bond, —O—CO—, or —CO—O—, because raw materials for such moieties are easily available.

Examples of the anthracene derivative represented by formula (VIII) according to the invention include, but are not limited to, compounds B-301 to B-312 shown below.

[Chemical Formula 61]

Compound B-301

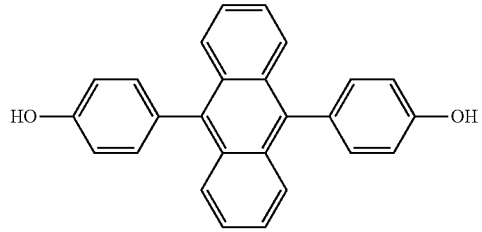

Compound B-302

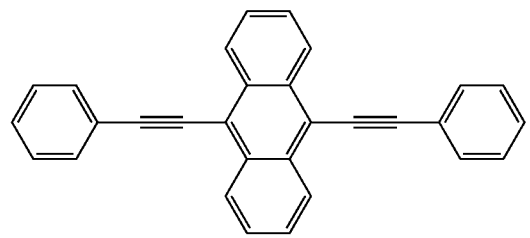

Compound B-303

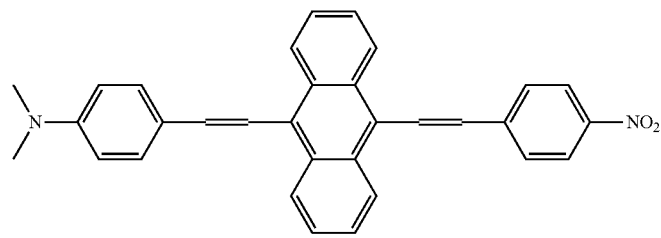

Compound B-304
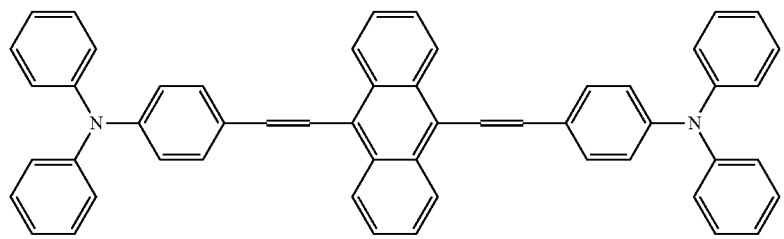
Compound B-305
Compound B-306
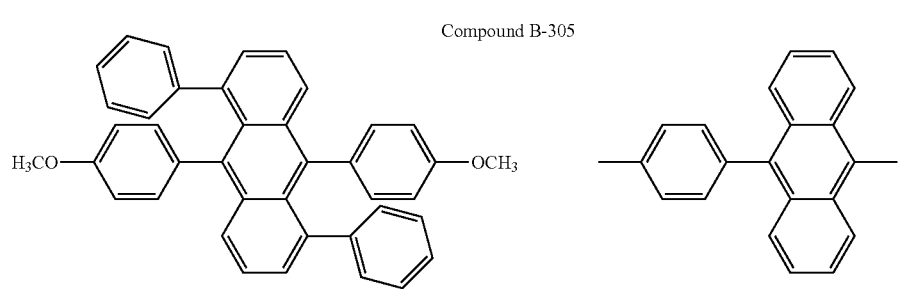
Compound B-307
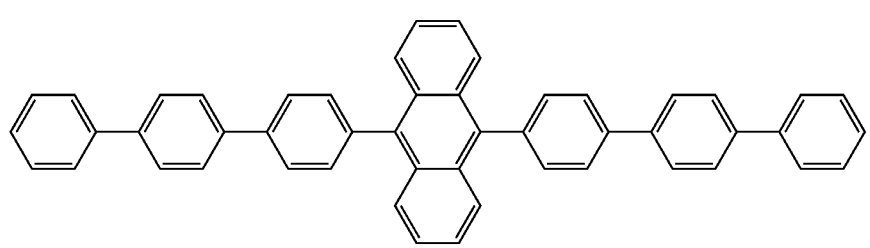
[Chemical Formula 62]
Compound B-308
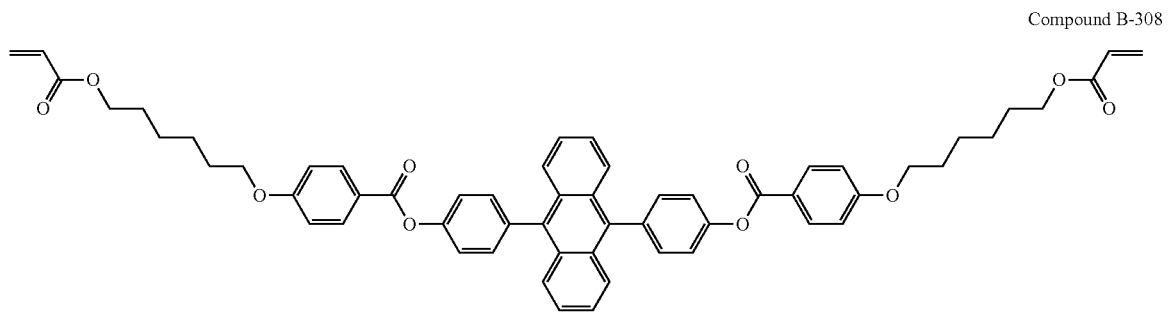
Compound B-309
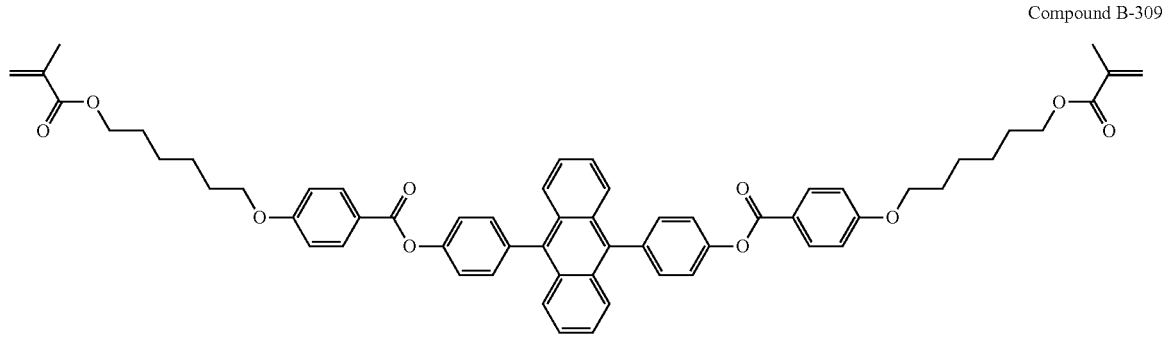

Compound B-310

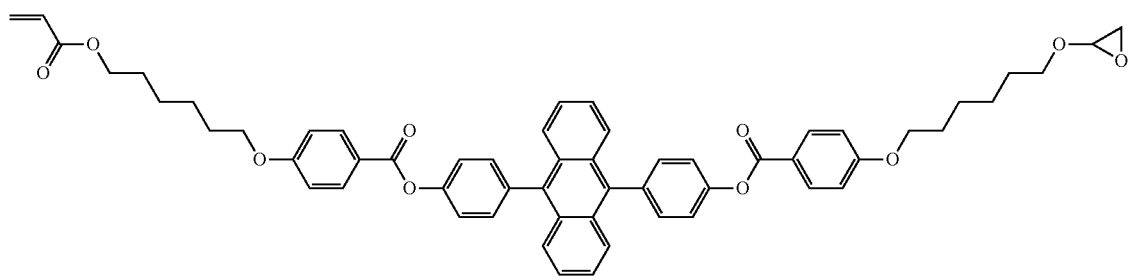

Compound B-311

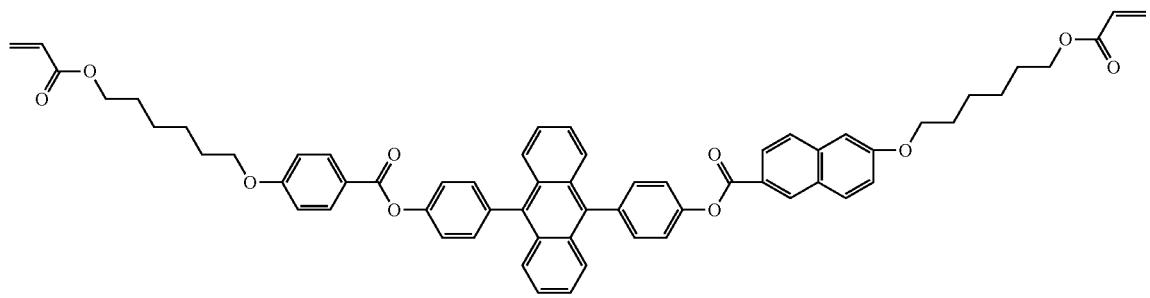

Compound B-312

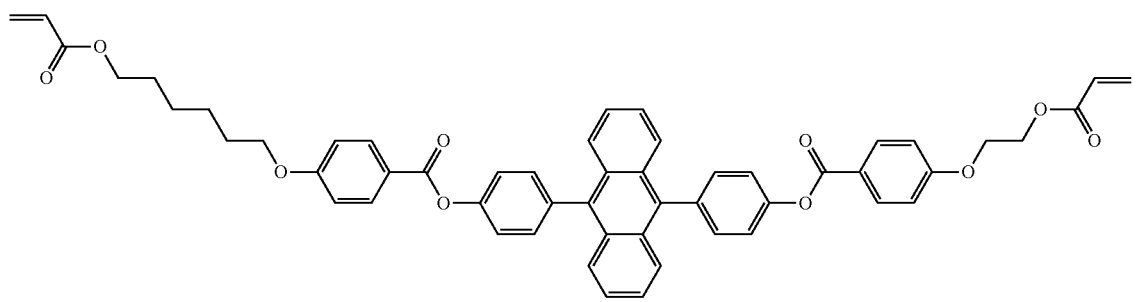

The method for producing the anthracene derivative represented by formula (VIII) is not restricted. For example, the anthracene derivative represented by formula (VIII) in which $R^{301}$ is represented by formula (V) can be produced according to methods used for the synthesis of common liquid crystal compounds, and more specifically can be produced according to scheme 1 or 2 shown below.

Although the schemes below show the synthesis of an anthracene derivative with a substituent of formula (V) in which ring $A^5$ is a benzene ring, $Z^6$ is a single bond, $Z^7$ is —COO—, and s is 1, other anthracene derivatives can also be produced in a similar manner according to the process shown below.

Scheme 1

[Chemical Formula 63]

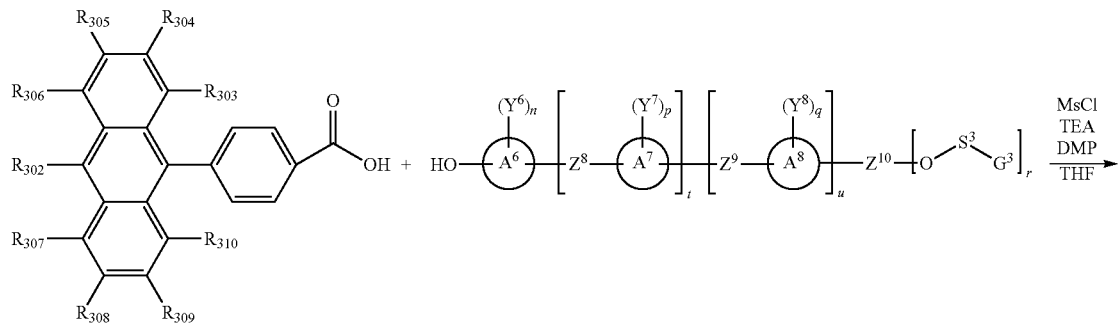

-continued

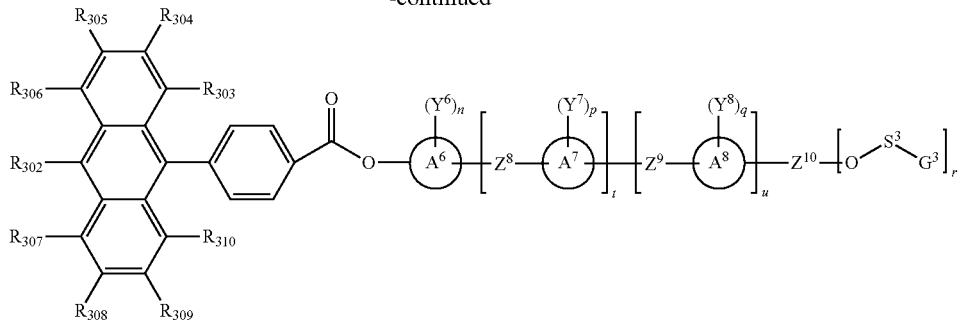

MsCl: Mecyl Chloride
TEA: Triethylamine
DMAP: 4-dimethylaminopyridine
THF: Tetrahydrofuran In the formula, $R^{302}$ to $R^{310}$ are the same as defined in formula (IV), and $A^6$, $A^7$, $A^8$, $S^3$, $Z^8$, $Z^9$, $Z^{10}$, $Y^6$, $Y^7$, $Y^8$, n, p, q, t, u, r, and $G^3$ are the same as defined in formula (V).

rate of emission of polarized light may be lower, and if it is more than 10% by weight, concentration quenching may occur, and the polymerization may be inhibited.

Scheme 2

[Chemical Formula 64]

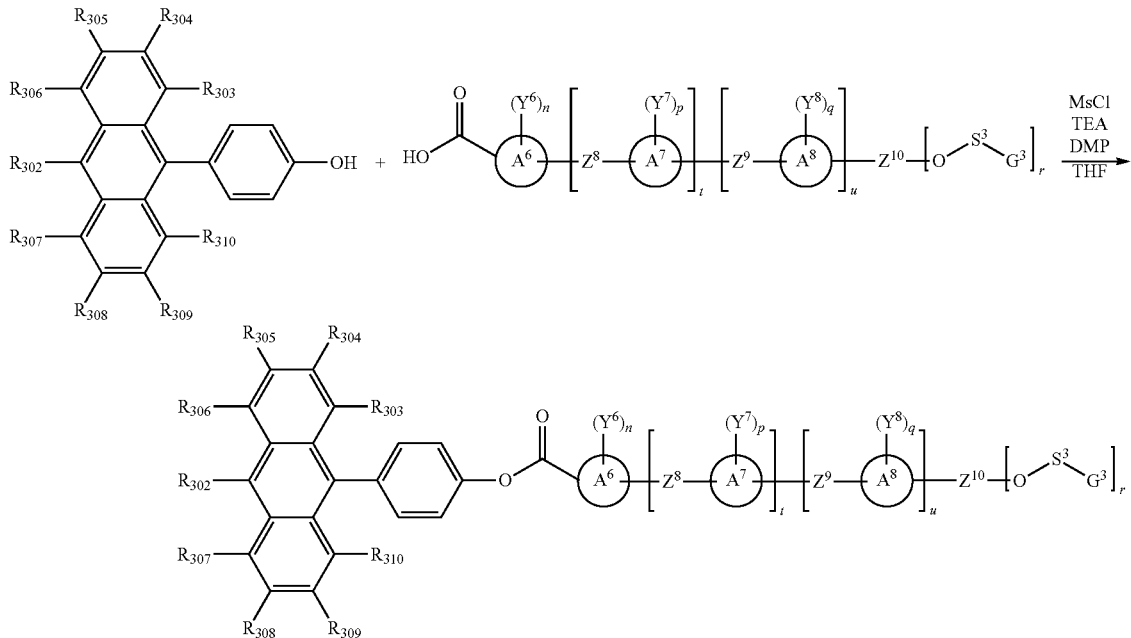

MsCl: Mecyl Chloride
TEA: Triethylamine
DMAP: 4-dimethylaminopyridine
THF: Tetrahydrofuran In the formula, $R^{302}$ to $R^{310}$ are the same as defined in formula (IV), and $A^6$, $A^7$, $A^8$, $S^3$, $Z^8$, $Z^9$, $Z^{10}$, $Y^6$, $Y^7$, $Y^8$, n, p, q, t, u, r, and $G^3$ are the same as defined in formula (V).

In the polymerizable liquid crystal composition of the invention, the content of the dye compound (B) selected from the naphtholactam derivative (B-1), the coumarin derivative (B-2), the Nile Red derivative (B-3), and the anthracene derivative (B-4) is preferably from 0.005 to 10% by weight, more preferably from 0.05 to 5% by weight, even more preferably from 0.1 to 3% by weight. If the content of the dye compound (B) is less than 0.005% by weight, the rate of emission of polarized light may be lower, and if it is more than 10% by weight, concentration quenching may occur, and the polymerization may be inhibited.

Any of the dye compounds (B) selected from the naphtholactam derivative (B-1), the coumarin derivative (B-2), the Nile Red derivative (B-3), and the anthracene derivative (B-4) may be used alone or in combination of two or more. When used, any of the dye compounds (B) selected from the naphtholactam derivative (B-1), the coumarin derivative (B-2), the Nile Red derivative (B-3), and the anthracene derivative (B-4) may be dispersed in the polymerizable liquid crystal composition of the invention, or may be photo-polymerized with the polymerizable liquid crystal compound (A) to form a polymer if having a polymerizable group.

<Polymerization Initiator (C)>

The polymerization initiator (C) is added to allow the curing reaction of the polymerizable liquid crystal composition of the invention to proceed rapidly. The polymerization initiator (C) may be a radical polymerization initiator, a cationic polymerization initiator, a thermal polymerization initiator, or the like.

The radical polymerization initiator may be a conventionally known compound, examples of which include benzoin ethers such as benzoin butyl ether; benzyl ketals such as benzyl dimethyl ketal; α-hydroxyacetophenones such as 1-hydroxy-1-benzoylcyclohexane, 2-hydroxy-2-benzoylpropane, and 2-hydroxy-2-(4'-isopropyl)benzoylpropane; chloroacetophenones such as 4-butylbenzoyltrichloromethane and 4-phenoxybenzoyldichloromethane; α-aminoacetophenones such as 1-benzyl-1-dimethylamino-1-(4'-morpholinobenzoyl)propane, 2-morpholyl-2-(4'-methylmercapto)benzoylpropane, 9-n-butyl-3,6-bis(2'-morpholinoisobutyroyl)carbazole, and 2-methyl-1-[4-(methylthio)phenyl]-2-morpholinopropan-1-one; acylphosphine oxides such as bis(2,4,6-trimethylbenzoyl)-phenylphosphine oxide; α-dicarbonyls such as benzil and benzoyl methyl formate; triazines such as p-methoxyphenyl-2,4-bis(trichloromethyl)-s-triazine, 2-methyl-4,6-bis(trichloromethyl)-s-triazine, 2-phenyl-4,6-bis(trichloromethyl)-s-triazine, 2-naphthyl-4,6-bis(trichloromethyl)-s-triazine, and 2-(p-butoxystyryl)-s-triazine; α-acyloxime esters such as the compounds described in JP-A Nos. 2000-80068, 2001-233842, and 2005-97141, Japanese Patent Application National Publication (Laid-Open) No. 2006-516246, Japanese Patent Nos. 3860170, and 3798008, and WO 2006/018973 A; benzoyl peroxide, 2,2'-azobisisobutyronitrile, ethylanthraquinone, 1,7-bis(9'-acridinyl)heptane, thioxanthone, 1-chloro-4-propoxythioxanthone, isopropylthioxanthone, diethylthioxanthone, benzophenone, phenyl biphenyl ketone, 4-benzoyl-4'-methyldiphenyl sulfide, 2-(p-butoxystyryl)-5-trichloromethyl-1,3,4-oxadiazole, 9-phenylacridine, 9,10-dimethylbenzophenazine, benzophenone/Michler's ketone, hexaarylbiimidazole/mercaptobenzimidazole, and thioxanthone/amine. Commercially available products thereof include N-1414, N-1717, N-1919, PZ-408, NCI-831, and NCI-930 (manufactured by ADEKA CORPORATION) and IRGACURE 369, IRGACURE 907, IRGACURE 819, IRGACURE 184, DAROCUR TPO, IRGACURE OXE01, and IRGACURE OXE02 (manufactured by BASF), etc. In particular, the radical polymerization initiator is preferably a compound represented by formula (X) or (XII) below because it has high sensitivity to energy rays for radical generation and enables production of highly stable polymer films.

[Chemical Formula 65]

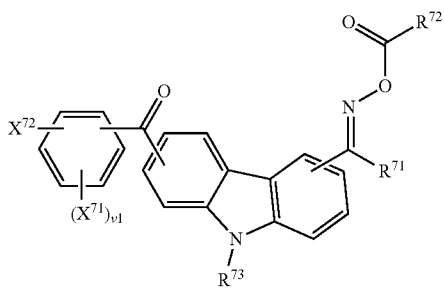

(X)

In the formula, $X^{71}$ represents a halogen atom or an alkyl group, $X^{72}$ represents a hydrogen atom, a halogen atom, an alkyl group, or a substituent represented by formula (XI) below, $R^{71}$, $R^{72}$, and $R^{73}$ each independently represent $R_x$, $OR_x$, $COR_x$, $SR_x$, $CONR_xR_y$, or CN, wherein $R_x$ and $R_y$ each represent an alkyl group, an aryl group, an arylalkyl group, or a heterocyclic group, these groups may be substituted with a halogen atom and/or a heterocyclic group, the alkyl group and the arylalkyl group may each have an alkylene moiety optionally interrupted by an unsaturated bond, an ether bond, a thioether bond, or an ester bond, and $R_x$ and $R_y$ may be linked together to form a ring, v1 is an integer of 0 to 4, and when v1 is 2 or more, a plurality of $X^{71}$ groups may be different.

[Chemical Formula 66]

(XI)

In the formula, ring P represents a cycloalkane ring, an aromatic ring, or a heterocyclic ring, $X^{73}$ represents a halogen atom or an alkyl group, $Y^{71}$ represents an oxygen atom, a sulfur atom, or a selenium atom, $Z^{71}$ represents an alkylene group of 1 to 5 carbon atoms, w represents an integer of 0 to 4, and when w is 2 or more, a plurality of $X^{73}$ groups may be different.

[Chemical Formula 67]

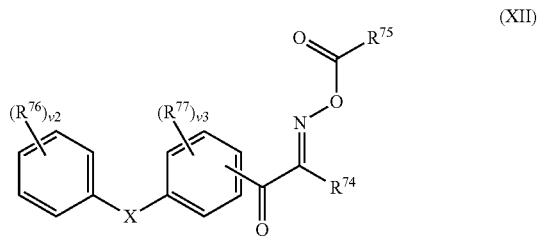

(XII)

In the formula, $R^{74}$ and $R^{75}$ each independently represent $R^{81}$, $OR^{81}$, $COR^{81}$, $SR^{81}$, $CONR^{82}R^{83}$, or CN, wherein $R^{81}$, $R^{82}$, and $R^{83}$ each independently represent a hydrogen atom, an alkyl group of 1 to 20 carbon atoms, an aryl group of 6 to 30 carbon atoms, an arylalkyl group of 7 to 30 carbon atoms, or a heterocyclic group of 2 to 20 carbon atoms, a hydrogen atom of the substituent represented by each of $R^{81}$, $R^{82}$, and $R^{83}$ may be further substituted with $OR^{91}$, $COR^{91}$, $SR^{91}$, $NR^{92}R^{93}$, $CONR^{92}R^{93}$, —$NR^{92}$—$OR^{93}$, —$NCOR^{92}$—$OCOR^{93}$, —$C(=N$—$OR^{91})$—$R^{92}$, —$C(=N$—$OCOR^{91})$—$R^{92}$, CN, a halogen atom, or $COOR^{91}$, $R^{76}$ and $R^{77}$ each independently represent a halogen atom or an alkyl group, $R^{91}$, $R^{92}$, and $R^{93}$ each independently represent a hydrogen atom, an alkyl group of 1 to 20 carbon atoms, an aryl group of 6 to 30 carbon atoms, an arylalkyl group of 7 to 30 carbon atoms, or a heterocyclic group of 2 to 20 carbon atoms, a hydrogen atom of the substituent represented by each of $R^{91}$, $R^{92}$, and $R^{93}$ may be further substituted with CN, a halogen atom, a hydroxyl group, or a carboxyl group, the substituent represented by each of $R^{81}$, $R^{82}$, $R^{83}$, $R^{91}$, $R^{92}$, and $R^{93}$ may have an alkylene moiety optionally interrupted once to five times by —O—, —S—, —COO—, —OCO—, —NR$^{94}$—, —NR$^{94}$COO—, —OCONR$^{94}$—, —SCO—, —COS—, —OCS—, or —CSO—, R$^{94}$ represents a hydrogen atom, an alkyl group of 1 to 20 carbon atoms, an aryl group of 6 to 30 carbon atoms, an arylalkyl group of 7 to 30 carbon atoms, or a heterocyclic group of 2 to 20 carbon atoms, an alkyl moiety of the substituent represented by each of R$^{81}$, R$^{82}$, R$^{83}$, R$^{91}$, R$^{92}$, and R$^{93}$ may have a branching side chain or may be cyclic alkyl, R$^{82}$ and R$^{83}$ or R$^{92}$ and R$^{93}$ may be linked together to form a ring, R$^{83}$ and R$^{94}$ each independently represent R$^{81}$ except for a hydrogen atom, OR$^{81}$, SR$^{81}$, COR$^{81}$, CONR$^{82}$R$^{83}$, NR$^{82}$COR$^{81}$, OCOR$^{81}$, COOR$^{81}$, SCOR$^{81}$, OCSR$^{81}$, COSR$^{81}$, CSOR$^{81}$, NO$_2$, CN, a halogen atom, or a group represented by formula (XIII) below, v2 and v3 each independently represent an integer of 0 to 4, and X represents an oxygen atom, a sulfur atom, a selenium atom, CR$^{101}$R$^{102}$, CO, NR$^{103}$, or PR$^{104}$, wherein R$^{101}$, R$^{102}$, R$^{103}$, and R$^{104}$ each independently represent a hydrogen atom, an alkyl group of 1 to 20 carbon atoms, an aryl group of 6 to 30 carbon atoms, or an arylalkyl group of 7 to 30 carbon atoms, an alkyl moiety of the substituent represented by each of R$^{101}$, R$^{102}$, R$^{103}$, and R$^{104}$ may have a branching side chain or may be cyclic alkyl, and R$^{101}$, R$^{102}$, R$^{103}$, and R$^{104}$ may be each independently linked with any adjacent benzene ring to form a ring.

[Chemical Formula 68]

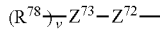

(XIII)

In the formula, Z$^{72}$ represents a linking moiety selected from —O—, —S—, —NR$^{92}$—, —NR$^{92}$CO—, —SO$_2$—, —CS—, —OCO—, or —COO—, Z$^{73}$ represents a linking moiety selected from an alkyl group of 1 to 20 carbon atoms, an aryl group of 6 to 30 carbon atoms, an arylalkyl group of 7 to 30 carbon atoms, and a heterocyclic group of 2 to 20 carbon atoms, which are each substituted with R$^{78}$ of 1 to 3, an alkylene moiety of the linking moiety represented by Z$^{73}$ may be interrupted once to five times by —O—, —S—, —COO—, —OCO—, —NR$^{92}$—, —NR$^{92}$COO—, —OCONR$^{92}$—, —SCO—, —COS—, —OCS—, or —CSO—, an alkylene moiety of the linking moiety represented by Z$^{73}$ may have a branching side chain or may be cyclic alkylene, R$^{75}$ represents OR$^{211}$, SR$^{211}$, CONR$^{212}$R$^{213}$, NR$^{212}$COR$^{213}$, OCOR$^{211}$, COOR$^{211}$, SCOR$^{211}$, OCSR$^{211}$, COSR$^{211}$, CSOR$^{211}$, CN, or a halogen atom, wherein R$^{211}$, R$^{212}$, and R$^{213}$ each independently represent a hydrogen atom, an alkyl group of 1 to 20 carbon atoms, an aryl group of 6 to 30 carbon atoms, or an arylalkyl group of 7 to 30 carbon atoms, an alkyl moiety of the substituent represented by each of R$^{211}$, R$^{212}$, and R$^{213}$ may have a branching side chain or may be cyclic alkyl, and R$^{212}$ and R$^{213}$ may be linked together to form a ring, and v represents an integer of 1 to 3.

The cationic polymerization initiator may be any compound capable of generating an acid upon exposure to energy rays. Preferably, the cationic polymerization initiator is a double salt, specifically an onium salt, capable of releasing a Lewis acid upon exposure to energy rays, or a derivative thereof. Such a compound is typically a cation-anion salt represented by the formula [M]$^{x+}$[N]$^{x-}$.

In the formula, the cation [M]$^{x-}$ is preferably an onium, and, for example, its structure can be represented by the formula [(R$^{60}$)$_y$Q]$^{x+}$.

In the formula, R$^{60}$ is an organic group of 1 to 60 carbon atoms, which may have any number of non-carbon atoms, y is an integer of 1 to 5, y pieces of R$^{60}$ are independent from one another, and any of y pieces of R$^{60}$ may be the same or different. At least one of y pieces of R$^{60}$ is preferably an aromatic ring-containing organic group as mentioned above. Q is an atom or an atomic group selected from S, N, Se, Te, P, As, Sb, Bi, O, I, Br, Cl, F, and N=N. The relation x=y−z also needs to be satisfied, wherein z is the valence of Q in the cation [M]$^{x+}$, provided that N=N is assumed to have a valence of 0.

The anion [N]$^{x-}$ is preferably a halide complex, and for example, its structure can be represented by the formula [LT$_1$]$^{x-}$.

In the formula, L is a metal or semimetal (metalloid) as a central atom of the halide complex, and examples thereof include B, P, As, Sb, Fe, Sn, Bi, Al, Ca, In, Ti, Zn, Sc, V, Cr, Mn, Co, etc. T is a halogen atom, and 1 is an integer of 3 to 7. The relation x=1−e also needs to be satisfied, wherein e is the valence of L in the anion [N]$^{x-}$.

Examples of the anion represented by [LT$_1$]$^{x-}$ in the formula include halide anions such as chloride anion, bromide anion, iodide anion, and fluoride anion; inorganic anions such as perchlorate anion, chlorate anion, thiocyanate anion, hexafluorophosphate anion, hexafluoroantimonate anion, hexafluoroarsenate anion, and tetrafluoroborate anion; organic sulfonate anions such as methanesulfonate ion, fluorosulfonate ion, benzenesulfonate anion, toluenesulfonate anion, 1-naphthylsulfonate anion, 2-naphthylsulfonate anion, trifluoromethanesulfonate anion, pentafluoroethanesulfonate anion, heptafluoropropanesulfonate anion, nonafluorobutanesulfonate anion, undecafluoropentanesulfonate anion, tridecafluorohexanesulfonate anion, pentadecafluoroheptanesulfonate anion, heptadecafluorooctanesulfonate ion, perfluoro-4-ethylcyclohexanesulfonate ion, N-alkyl(or aryl)diphenylamine-4-sulfonate anion, 2-amino-4-methyl-5-chlorobenzenesulfonate anion, 2-amino-5-nitrobenenesulfonate anion, the sulfonate anion described in JP-A No. 2004-53799, camphorsulfonate anion, fluorobenzenesulfonate anion, difluorobenzenesulfonate anion, trifluorobenzenesulfonate anion, tetrafluorobenzenesulfonate anion, and pentafluorobenzenesulfonate anion; organic phosphate anions such as octylphosphate anion, dodecylphosphate anion, octadecylphosphate anion, phenylphosphate anion, nonylphenylphosphate anion, and 2,2'-methylenebis(4,6-di-tert-butylphenyl)phosphonate anion; organic fluorosulfonimide ions such as bis(trifluoromethanesulfone)imide ion, bis(pentafluoroethanesulfone)imide ion, bis(heptafluoropropanesulfone)imide ion, bis(nonafluorobutanesulfone)imide ion, bis(undecafluoropentanesulfone)imide ion, bis(pentadecafluoroheptanesulfone)imide ion, bis(tridecafluorohexanesulfone)imide ion, bis(heptadecafluorooctanesulfonimide) ion, (trifluoromethanesulfone)(nonafluorobutanesulfone)imide ion, (methanesulfone)(trifluoromethanesulfone)imide ion, and cyclohexafluoropropane-1,3-bis(sulfonyl)imide anion; tetraarylborate anions such as tetrakis(pentafluorophenyl)borate aniion, tetrakis(4-fluorophenyl)borate ion, tetraphenylborate ion, and the borate anions described in JP-A No. 2008-81470, 2007-112854, and 06-184170, Japanese Patent Application National Publication (Laid-Open) No. 2002-526391, and PCT/JP2008/069562; various aliphatic or aromatic carboxylate anions; organic sulfonylmethide ions such as tris(trifluoromethanesulfonyl)methide and tris(methanesulfonyl)methide; and alkylsulfonate ions, fluoro-substituted alkylsulfonate ions, and alkylsulfonimides or fluoro-substituted alkylsulfonimides substituted with an acryloyloxy group, a methacryloyloxy group, or an aliphatic cycloalkyl group such as a norbornyl group or an adamantyl group. If necessary, other anions may also be used, such as quencher anions having the function of deexciting (quenching) an active molecule in an excited state; and metallocene compound anions such as ferrocene or ruthenocene compounds having a cyclopentadienyl ring with an anionic group such as a carboxyl group, a phosphonic acid group, or a sulfonic acid group.

Among such onium salts, aromatic onium salts in the groups (a) to (c) below are particularly advantageously used in the invention. One of these salts may be used alone, or two or more of these salts may be used in a mixture.

(a) Aromatic diazonium salts such as phenyldiazonium hexafluorophosphate, 4-methoxyphenyldiazonium hexafluoroantimonate, and 4-methylphenyldiazonium hexafluorophosphate;

(b) Aromatic iodonium salts such as diphenyliodonium hexafluoroantimonate, di(4-methylphenyl)iodonium hexafluorophosphate, di(4-tert-butylphenyl)iodonium hexafluorophosphate, and tolylcumyliodonium tetrakis(pentafluorophenyl)borate;

(c) Triarylsulfonium salts such as triphenylsulfonium hexafluoroantimonate, tris(4-methoxyphenyl)sulfonium hexafluorophosphate, diphenyl-4-thiophenoxyphenylsulfonium hexafluoroantimonate, diphenyl-4-thiophenoxyphenylsulfonium hexafluorophosphate, 4,4'-bis(diphenylsulfonio)phenylsulfide-bis-hexafluoroantimonate, 4,4'-bis(diphenylsulfonio)phenylsulfide-bis-hexafluorophosphate, 4,4'-bis[di(β-hydroxyethoxy)phenylsulfonio]phenylsulfide-bis-hexafluoroantimonate, 4,4'-bis[di(β-hydroxyethoxy)phenylsulfonio]phenylsulfide-bis-hexafluorophosphate, 4-[4'-(benzoyl)phenylthio]phenyl-di-(4-fluorophenyl)sulfonium hexafluoroantimonate, 4-[4'-(benzoyl)phenylthio]phenyl-di-(4-fluorophenyl)sulfonium hexafluorophosphate, 4-(2-chloro-4-benzoylphenylthio)phenyl-di-(4-fluorophenyl)sulfonium hexafluoroantimonate; and aromatic sulfonium salts such as a mixture of diphenyl-4-thiophenoxyphenylsulfonium hexafluoroantimonate and 4,4'-bis(diphenylsulfonio)phenylsulfide-bis-hexafluorophosphate.

Other preferred examples include iron-arene complexes such as ($\eta^5$-2,4-cyclopentadien-1-yl)[(1,2,3,4,5,6-$\eta$)-(1-methylethyl)-benzene]-iron-hexafluorop hosphate, and a mixture of an aluminum complex such as tris(acetylacetonato)alumninum, tris(ethylacetonatoacetato)aluminum, or tris(salicylaldehydato)aluminum and a silanol such as triphenylsilanol.

Among them, aromatic iodonium salts, aromatic sulfonium salts, and iron-arene complexes are preferably used in view of practical aspect and photosensitivity.

The thermal polymerization initiator may be of any known type, such as peroxides such as benzoyl peroxide, 2,4-dichlorobenzoyl peroxide, 1,1-di(tert-butylperoxy)-3,3,5-trimethylcyclohexane, 4,4-di(tert-butyl-peroxy)butyl valerate, and dicumyl peroxide; azo compounds such as 2,2'-azobisisobutyronitrile; and tetramethylthiuram disulfide.

The content of the polymerization initiator (C) in the polymerizable liquid crystal composition of the invention is preferably 10% by weight or less, more preferably 5% by weight or less, even more preferably from 0.5 to 4% by weight. If the content of the radical initiator (C) is more than 10 parts by weight, precipitates may occur in a layer to make it unstable.

The polymerizable liquid crystal composition of the invention may further contain a liquid crystal compound other than the polymerizable liquid crystal compound (A). In this context, the term "liquid crystal compound" is intended to include a conventionally known liquid crystal compound, a liquid crystal-like compound, and a mixture thereof. The liquid crystal compound may be one commonly used in the art, examples of which include, but are not limited to, compounds 1 to 29 shown below. The content of the liquid crystal compound is preferably from 1 to 200% by weight, more preferably from 10 to 100% by weight, based on 100 parts by weight of the polymerizable liquid crystal compound (A).

[Chemical Formula 69]

Compound 1

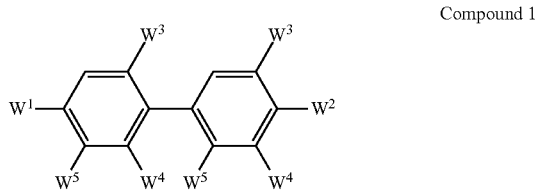

Compound 2

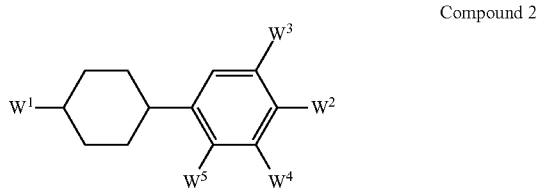

Compound 3

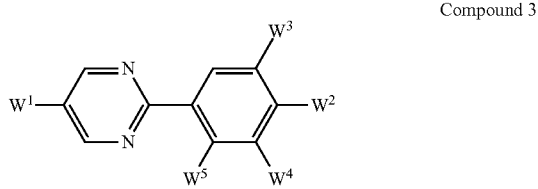

Compound 4

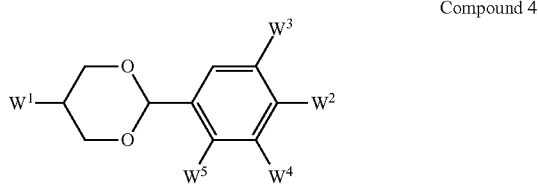

Compound 5

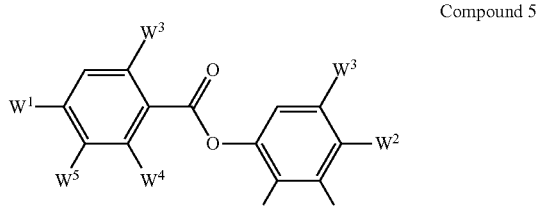

Compound 6

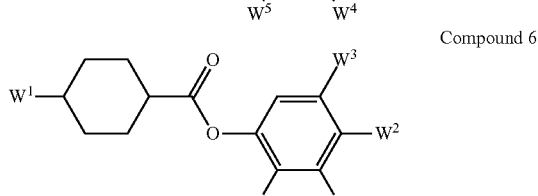

Compound 7

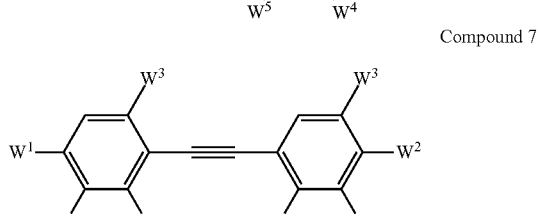

Compound 8
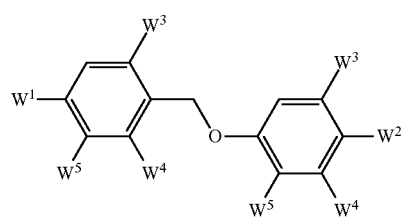
Compound 9
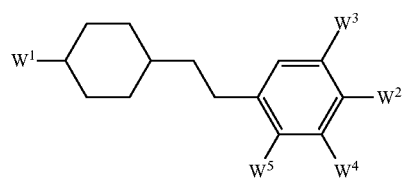
Compound 10
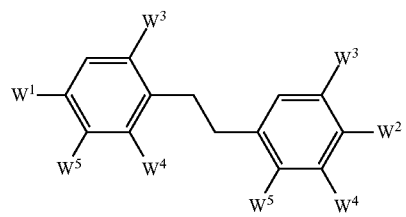
Compound 11
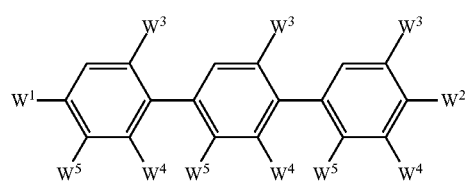
Compound 12
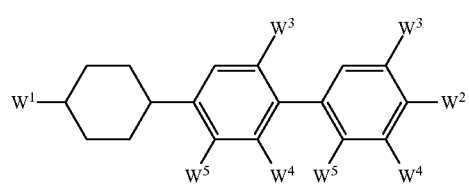
Compound 13
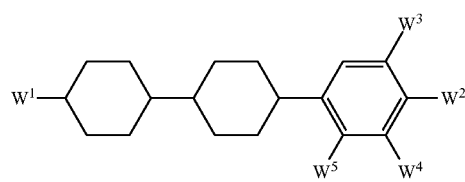
Compound 14
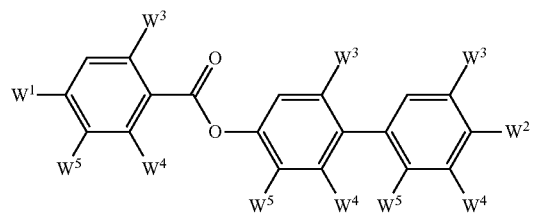
Compound 15
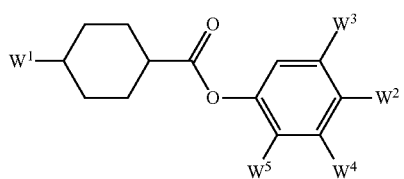
Compound 16
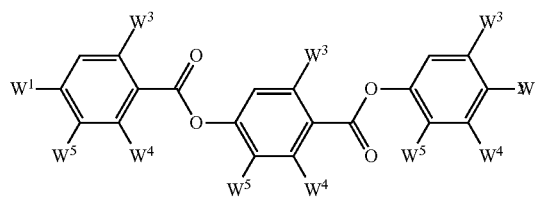
Compound 17
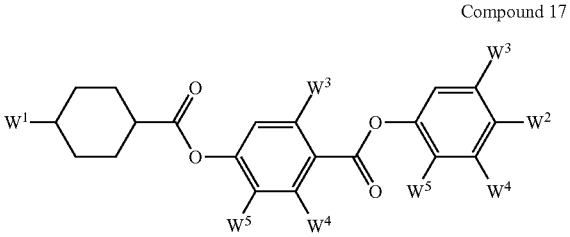
Compound 18
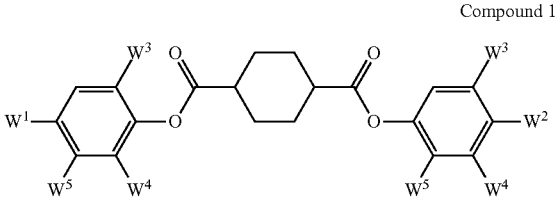
Compound 19
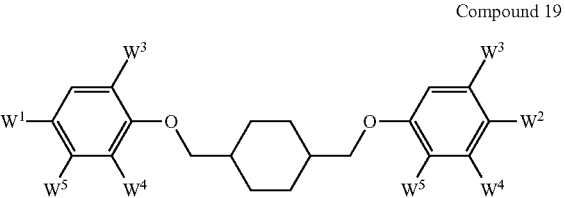
Compound 20
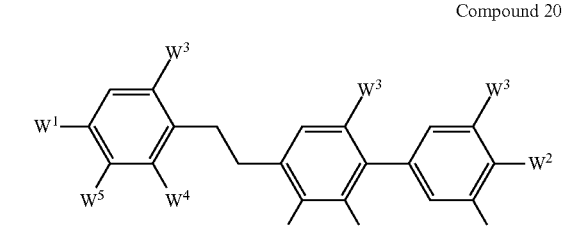
Compound 21
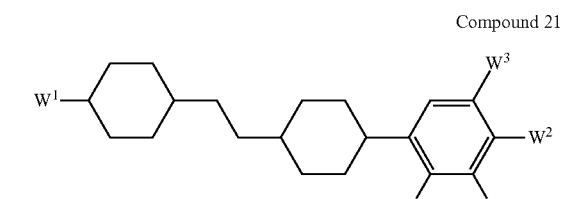

[Chemical Formula 70]

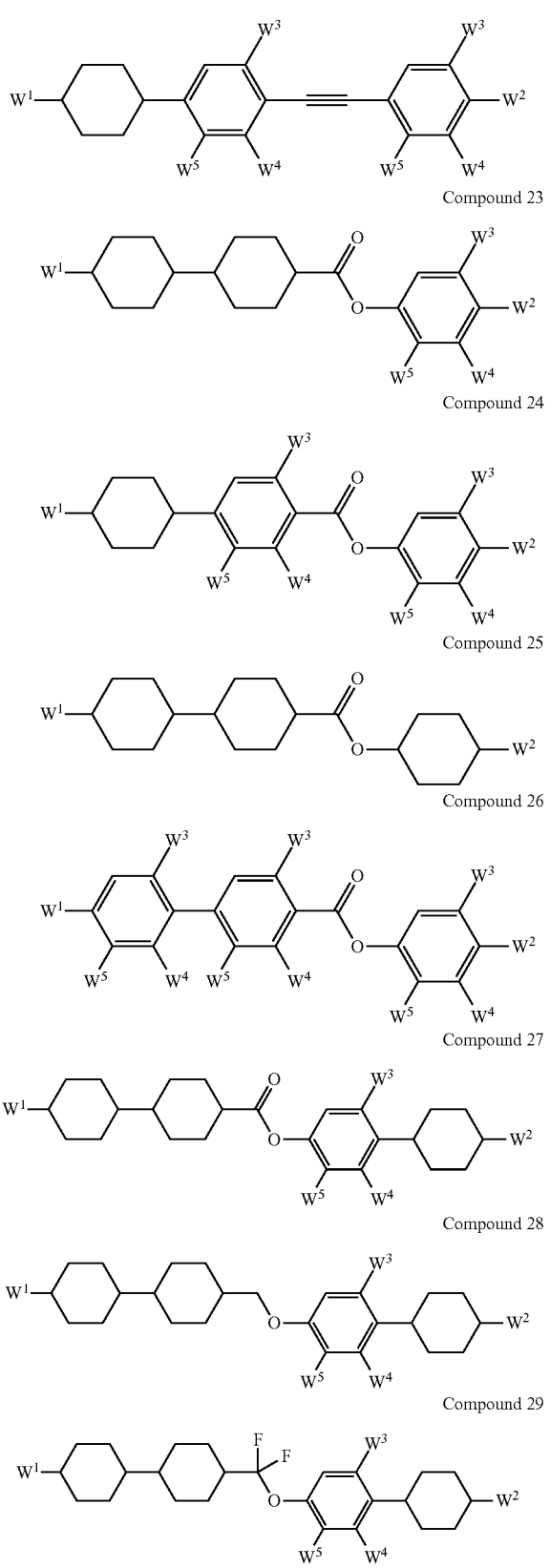

Compound 22
Compound 23
Compound 24
Compound 25
Compound 26
Compound 27
Compound 28
Compound 29

In the formulae, $W^1$ represents a hydrogen atom, an optionally branched alkyl group of 1 to 8 carbon atoms, an optionally branched alkoxy group of 1 to 8 carbon atoms, an optionally branched alkenyl group of 1 to 8 carbon atoms, an optionally branched alkenyloxy group of 1 to 8 carbon atoms, an optionally branched alkynyl group of 1 to 8 carbon atoms, an optionally branched alkynyloxy group of 1 to 8 carbon atoms, an optionally branched alkoxyalkyl group of 1 to 8 carbon atoms, an optionally branched alkanoyloxy group of 1 to 8 carbon atoms, or an optionally branched alkoxycarbonyl group of 1 to 8 carbon atoms, each of which may be substituted with a halogen atom, a cyano group, or any other substituent, $W^2$ represents a cyano group, a halogen atom, or the moiety represented by $W^1$, and $W^3$, $W^4$, and $W^5$ each represent a hydrogen atom, a halogen atom, or a cyano group.

The polymerizable liquid crystal composition of the invention may also contain a sensitizer. The sensitizer has the function of absorbing light with a wavelength in the near infrared to visible range and transferring the absorbed light energy to other substances. The sensitizer may be one known in the art, such as a carbonyl compound such as benzoin or acetophenone, an organic peroxide such as benzoyl peroxide, an azo compound, a halide, a sulfur compound, an inorganic ion, thioxanthone, phenothiazine, chlorothioxanthone, xanthone, anthracene, diphenylanthracene, or rubrene. When the sensitizer is added, the content of the sensitizer in the polymerizable liquid crystal composition of the invention is preferably 10% by weight or less, more preferably 5% by weight or less, even more preferably in the range of 0.1 to 3% by weight.

The sensitizer should be selected depending on the relationship between the absorption wavelengths of the colorant (B) and the sensitizer, and the difference between them is preferably 100 nm or less. In general, the sensitizer to be selected has an absorption wavelength shorter than that of the colorant (B). When a light source with an emission wavelength in the ultraviolet region is used, at least one sensitizer suitable for the shortest emission wavelength of the colorant (B) should be selected and used. When a light source with an emission wavelength in the visible region or ambient light is used, at least one suitable sensitizer is selected and used for each of different types of the colorant (B).

In the invention, the sensitizer can absorb light energy in every direction from a light source and efficiently convert the light energy in every direction into polarized light by transferring the absorbed light energy to the oriented fluorescent material. Thus, to absorb light energy in every direction, the sensitizer is preferably less oriented and preferably resists orientation even when subjected to an orientation process such as stretching. The content of the sensitizer may be from 0.005% by weight to 10% by weight, preferably from 0.05% by weight to 5% by weight, even more preferably from 0.1% by weight to 3% by weight, based on the total weight of the polymer film materials. If the sensitizer content is too low, the amount of light energy absorption may be low, and if the sensitizer content is too high, concentration quenching may occur to reduce the light energy use efficiency.

When the polymerizable liquid crystal composition of the invention is used for applications such as raw materials for polarizing films or oriented films, printing ink compositions, coating materials, and protective films, the polymerizable liquid crystal composition may contain an optional component such as a metal, a metal complex, a wax, a surfactant, a leveling agent, a thixotropic agent, a gelling agent, a polysaccharide, an ultraviolet absorber, an infrared absorber, an antioxidant, a plasticizer, an ion-exchange resin, a metal oxide such as titanium oxide, a polymerization inhibitor, a storage stabilizer, a crosslinking agent, a liquid crystal orientation aid, fine particles of inorganic and organic materials, or a functional compound such as a polymer. The total content of such optional components in the polymerizable liquid crystal composition of the invention should be 10% by weight or less.

The surfactant is preferably such that it has an excluded volume effect distributed over an air interface side and has other effects, such as making it easy to apply the polymerizable liquid crystal composition to a supporting substrate or the like or controlling the orientation of the liquid crystal phase. Examples of the surfactant include quaternary ammonium salts, alkylamine oxides, polyamine derivatives, polyoxyethylene-polyoxypropylene condensates, polyethylene glycol and esters thereof, sodium lauryl sulfate, ammonium lauryl sulfate, lauryl sulfate amines, alkyl-substituted aromatic sulfonates, alkyl phosphates, perfluoroalkyl sulfonates, perfluoroalkyl carboxylates, perfluoroalkyl ethylene oxide adducts, perfluoroalkyl trimethyl ammonium salts, etc. The content of the surfactant in the polymerizable liquid crystal composition of the invention is preferably in the range of 0.001 to 5% by weight, more preferably in the range of 0.01 to 1% by weight, although the preferred content of the surfactant depends on the type of the surfactant, the ratio of the components in the composition, or other factors.

The storage stabilizer is effective in improving the storage stability of the polymerizable liquid crystal composition. Examples of the stabilizer that may be used include hydroquinone, hydroquinone monoalkyl ethers, tert-butylcatechols, pyrogallols, thiophenols, nitro compounds, 2-naphthylamines, 2-hydroxynaphthalenes, etc. When such a stabilizer is added, the content of the stabilizer in the polymerizable liquid crystal composition of the invention is preferably 1% by weight or less, more preferably 0.5% by weight or less.

There is no restriction to the antioxidant, and a known compound may be used as the antioxidant. Examples include hydroquinone, 2,6-di-tert-butyl-p-cresol, 2,6-di-tert-butylphenol, triphenylphosphite, trialkylphosphite, etc.

There is no restriction to the ultraviolet absorber, and a known compound may be used as the ultraviolet absorber. Examples include salicylate ester compounds, benzophenol compounds, benzotriazole compounds, cyanoacrylate compounds, or materials having ultraviolet absorbing ability imparted by nickel complex salt compounds or the like.

The fine particles may be used to control optical (refractive index) anisotropy ($\Delta n$) or to increase the strength of the polymer film. The fine particles may be made of an inorganic material, an organic material, a metal, or any other material. To prevent aggregation, fine particles with particle sizes of 0.001 to 0.1 μm are preferably used, and fine particles with particle sizes of 0.001 to 0.05 μm are more preferably used. The fine particles preferably have a sharp particle size distribution. When fine particles are used, the content of the fine particles in the polymerizable liquid crystal composition of the invention is preferably in the range of 0.1 to 30% by weight.

Examples of the inorganic material include ceramics, fluorphlogophite, fluortetrasilicic mica, taeniolite, fluorovermiculite, fluorohectorite, hectorite, saponite, stevensite, montmorillonite, beidellite, kaolinite, fraipontite, ZnO, $TiO_2$, $CeO_2$, $Al_2O_3$, $Fe_2O_3$, $ZrO_2$, $MgF_2$, $SiO_2$, $SrCO_3$, $Ba(OH)_2$, $Ca(OH)_2$, $Ga(OH)_3$, $Al(OH)_3$, $Mg(OH)_2$, $Zr(OH)_4$, etc. Fine particles of needle crystals of calcium carbonate or the like have optical anisotropy, and the optical anisotropy of the polymer can be controlled using such fine particles. Examples of the organic material include carbon nanotubes, fullerene, dendrimers, polyvinyl alcohol, polymethacrylate, polyimide, etc.

The polymer that may be used is preferably a polymer compound capable of controlling the electric characteristics or orientation of the polymer film and soluble in the solvent. Examples of such a polymer compound include polyamide, polyurethane, polyurea, polyepoxide, polyester, polyester polyol, etc.

There is no restriction to the antioxidant, and a known compound may be used as the antioxidant. Examples include hydroquinone, 2,6-di-tert-butyl-p-cresol, 2,6-di-tert-butylphenol, triphenylphosphite, trialkylphosphite, etc.

Next, the polarized light-emitting coating material including the polymerizable liquid crystal composition of the invention will be described. Unless otherwise stated, the above description of the polymerizable liquid crystal composition of the invention will appropriately apply to the coating material.

The polarized light-emitting coating material has the property of emitting polarized light when subjected to a process including applying the coating material to an alignment-treated support or a laminate of a support and an alignment film, drying the coating material, and then applying heat and/or ultraviolet rays or the like to the coating material so that components in the coating material, specifically, a polymer of the polymerizable liquid crystal compound (A) and the colorant (B) are oriented and fixed.

The polarized light-emitting coating material of the invention contains the polymerizable liquid crystal composition, specifically the polymerizable liquid crystal compound (A), the colorant (B), and the polymerization initiator (C) as essential components, and optionally contains any of various additive components described above, such as a liquid crystal compound other than the polymerizable liquid crystal compound (A). If necessary, a solvent may be further added to dissolve these components. The coating material may subjected to a process including applying it to an alignment-treated support or a laminate of a support and an alignment film or applying it to an alignment film, which has been formed and then transferred onto a support; applying heat to the polymerizable liquid crystal compound (A) and colorant (B) being spontaneously and uniaxially oriented, so that the orientation is facilitated; and applying ultraviolet rays or the like to it to fix, by reaction of the polymerizable reactive group, an oriented structure composed of a polymer of the polymerizable liquid crystal compound (A) and the colorant (B), so that the laminate of the invention capable of emitting polarized light (polarized light-emitting laminate) can be produced.

The oriented structure refers to a state in which a polymer of the polymerizable liquid crystal compound (A) and the colorant (B) are arranged in a certain direction and show anisotropy with respect to in-plane optical transparency. The higher the degree of the orientation, the larger the degree of polarization of the laminate produced from the polarized light-emitting coating material.

Preferred examples of the support include, but are not limited to, a glass sheet, a polyethylene terephthalate sheet, a polycarbonate sheet, a polyimide sheet, a polyamide sheet, a polymethyl methacrylate sheet, a polystyrene sheet, a polyvinyl chloride sheet, a polyolefin sheet, a cycloolefin polymer sheet, a polytetrafluoroethylene sheet, a triacetylcellulose sheet, a norbornene sheet, a polyvinyl alcohol sheet, a cellulose acetate sheet, a polyarylate sheet, a polysulfone sheet, a polyether sulfone sheet, a silicon sheet, a reflective sheet, a calcite sheet, a quartz sheet, a glass sheet, a paper sheet, a wood sheet, a metal sheet, etc.

The solvent may be of any type capable of dissolving the polymerizable liquid crystal composition, although high-boiling-point solvents are not preferred in terms of productivity. Examples of the solvent include ketones such as methyl ethyl ketone, methyl amyl ketone, diethyl ketone, acetone, methyl isopropyl ketone, methyl isobutyl ketone, cyclopentanone, cyclohexanone, and diacetone alcohol; ether solvents such as ethyl ether, dioxane, tetrahydrofuran, 1,2-dimethoxyethane, 1,2-diethoxyethane, ethylene glycol dimethyl ether, diethylene glycol dimethyl ether, and dipropylene glycol dimethyl ether; ester solvents such as methyl acetate, ethyl acetate, n-propyl acetate, isopropyl acetate, n-butyl acetate, methoxybutyl acetate, methyl lactate, and ethyl lactate; cellosolve solvents such as ethylene glycol monomethyl ether, ethylene glycol monoethyl ether, ethylene glycol mono-n-butyl ether, ethylene glycol monoethyl ether acetate, propylene glycol monomethyl ether acetate, propylene glycol monoethyl ether acetate, and butyl cellosolve; alcohol solvents such as methanol, ethanol, iso- or n-propanol, iso- or n-butanol, amyl alcohol, tert-butyl alcohol, diacetone alcohol, glycerin, monoacetylene, ethylene glycol, triethylene glycol, and hexylene glycol; aromatic hydrocarbon solvents such as benzene, toluene, xylene, n-butylbenzene, diethylbenzene, methoxybenzene, 1,2-dimethoxybenzene, mesitylene, and tetralin; aliphatic hydrocarbon solvents such as hexane, heptane, octane, and cyclohexane; terpene hydrocarbon oils such as turpentine oil, D-limonene, and pinene; paraffinic solvents such as mineral spirit, Swasol #310 (Cosmo Matsuyama Oil Co., Ltd.), and Solvesso #100 (Exon Chemical Co., Ltd.); halogenated aliphatic hydrocarbon solvents such as carbon tetrachloride, chloroform, dichloromethane, dichloroethane, trichloroethylene, tetrachloroethylene, and methylene chloride; halogenated aromatic hydrocarbon solvents such as chlorobenzene; acrylic esters such as ethyl acrylate and butyl acrylate; fluorinated alcohols such as 2,2,3,3-tetrafluoropropanol; and carbitol solvents, aniline, triethylamine, pyridine, acetic acid, acetonitrile, carbon disulfide, γ-butyrolactone, N,N-dimethylformamide, 2-pyrrolidone, N-methyl-2-pyrrolidone, etc. In particular, ketones or cellosolve solvents, especially methyl ethyl ketone, cyclohexanone, and tetrahydrofuran are preferred because they are safe and have good solvent properties. These solvents may be used singly or in mixture of two or more.

When the alignment film is not used, the molecular orientation can be controlled using a known method such as a rubbing method, a friction transfer method, a surface development method, or an LB method. Alternatively, orientation may also be achieved using magnetic fields, electric fields, or shearing stress.

The polarized light-emitting coating material of the invention may be applied to the support or the alignment film by a hot-melt method or by a process including dissolving the coating material in a solvent and applying the solution. Usually, a solution of the coating material in a solvent is used for coating.

The coating material can be applied to the support or the alignment film using a known method such as curtain coating, extrusion coating, roll coating, spin coating, dip coating, bar coating, spray coating, slide coating, blade coating, gravure coating, or printing coating.

Heating for facilitating the orientation of the polymerizable liquid crystal compound (A) and the colorant (B) (orientation by heating) is usually performed at a temperature of from the Cr (crystal)-N (nematic) phase transition temperature of the polymerizable liquid crystal composition to the N (nematic)-I (isotropic) phase transition temperature of the polymerizable liquid crystal composition. The heating temperature is preferably at most 50° C. higher than the Cr—N phase transition temperature, because at high temperature, thermal polymerization can proceed to inhibit the orientation. The period of the orientation by heating is preferably, but not limited to, about 10 seconds to about 10 minutes.

The oriented structure can be fixed by curing reaction of the polymerizable reactive group of the polymerizable liquid crystal compound (A) in the polarized light-emitting coating material of the invention. The curing can be achieved by a known polymerization method using heat or electromagnetic waves. In particular, the curing is preferably achieved by exposure to active energy rays. The active energy rays may be ultraviolet rays, visible rays, infrared rays, electron beams, or electromagnetic waves such as X rays. In particular, ultraviolet rays or visible rays are preferred. The wavelength is preferably in the range of 150 to 500 nm, more preferably in the range of 250 to 450 nm, even more preferably in the range of 300 to 400 nm. The light source may be a low-pressure mercury lamp (sterilization lamp, fluorescent chemical lamp, or black light), a high voltage discharge lamp (high-pressure mercury lamp or metal halide lamp), a short arc discharge lamp (extra-high pressure mercury lamp, xenon lamp, or mercury-xenon lamp), or the like. A high-pressure mercury lamp or an extra-high pressure mercury lamp is preferably used. Light from the light source may be directly applied to the liquid crystal composition, or a specific wavelength (or specific wavelength region) selected by a filter may be applied to the liquid crystal composition. The irradiation energy density is preferably in the range of 10 to 50,000 mJ/cm$^2$, more preferably in the range of 10 to 20,000 mJ/cm$^2$. The illuminance is preferably in the range of 0.1 to 5,000 mW/cm$^2$, more preferably in the range of 1 to 2,000 mW/cm$^2$. If the amount of exposure is small, polymerization may be insufficient. If the amount of exposure is large, rapid curing may occur to cause yellowing or degradation. Polymerization may also be performed while a magnetic or electric field is applied.

The alignment film may be a conventionally known alignment film, such as a rubbed film produced by a process including forming a thin film of polyimide, polyamide, polyvinyl alcohol, or the like on a support and rubbing the thin film with a rayon cloth or the like; an obliquely vapor-deposited film; an optical alignment film formed by applying polarized ultraviolet rays to a polyimide or a polymer having a photo-crosslinking group such as cinnamate or azobenzene; or a stretched film, or the like.

When the alignment film is not used, the molecular orientation can be controlled using a known method such as a rubbing method, a friction transfer method, a surface development method, or an LB method. Alternatively, orientation may also be achieved using magnetic fields, electric fields, or shearing stress.

The polarized light-emitting coating material of the invention may be applied to the support or the alignment film by a hot-melt method or by a process including dissolving the coating material in a solvent and applying the solution. Usually, a solution of the coating material in a solvent is used for coating.

The coating material can be applied to the support or the alignment film using a known method such as curtain coating, extrusion coating, roll coating, spin coating, dip coating, bar coating, spray coating, slide coating, blade coating, gravure coating, or printing coating.

Next, the polarized light-emitting laminate of the invention will be described. Unless otherwise stated, the above description of the polymerizable liquid crystal composition and the polarized light-emitting coating material of the invention will appropriately apply to the laminate.

As mentioned above, the polarized light-emitting laminate of the invention is obtained by applying the polarized light-emitting coating material of the invention to a support, and contains a polymer obtained by photopolymerization of the polymerizable liquid crystal composition.

The film formed by applying the polarized light-emitting coating material to the support preferably has a thickness selected from the range of 0.01 to 100 μm although it may be selected as needed depending on the intended use of the laminate. When a plurality of the films are stacked and used, each film also preferably has a thickness in the above range.

The polarized light-emitting laminate of the invention emits polarized light when irradiated with exciting light with a specific wavelength from an exciting light source. The exciting light source to be used may be an ultraviolet LED lamp, a xenon lamp, a short-wavelength semiconductor laser, a gas laser, a discharge tube, an incandescent lamp, a fluorescent light, a halogen lamp, or the like. Two or more of these light sources may be used in combination.

The polarized light-emitting laminate of the invention can be used to form a selective reflection film, a brightness enhancement film, an optically anisotropic film, an optical compensation film, a retardation plate, a polarizer, or any other element for liquid crystal displays, to form a 3-D display, to form a polymer dispersion liquid crystal (PDLC) electronic paper device, to form a digital paper device, to form a liquid crystal laser, to form an anti-counterfeiting film, label, sheet, plate, card, identification mark, identification label, or identification marker, or to form a polarizing device for one-, two-, or three-dimensional identification codes such as barcodes, data codes, VeriCode, MaxiCode, QR code (registered trademark), or CP code.

The polarizing device may include a wavelength selection filter for extracting exciting light with a specific wavelength; a polarizing plate; a photo-detector such as a photodiode, a photo-multiplier, or a CCD; an optical modulator for increasing the sensitivity of detection of polarized light emission; and other components. The polarizing device may also be provided with a protective layer.

Next, the novel naphtholactam derivative of the invention will be described. Unless otherwise stated, the above description of the polymerizable liquid crystal composition of the invention will appropriately apply to the derivative.

The novel naphtholactam derivative of the invention is a compound represented by formula (IV'), which corresponds to a compound represented by formula (IV) in which at least one of $R^5$ to $R^{10}$ is a substituent represented by formula (V) (a substituent represented by formula (V')).

Examples of the novel naphtholactam derivative of the invention represented by formula (IV') include, but are not limited to, compounds B-1 to B-52.

Next, the novel coumarin derivative of the invention will be described. Unless otherwise stated, the above description of the polymerizable liquid crystal composition of the invention will appropriately apply to the derivative.

The novel coumarin derivative of the invention is a compound represented by formula (VI'), which corresponds to a compound represented by formula (VI) in which at least one of $R^{111}$ to $R^{116}$ is a substituent represented by formula (V) (a substituent represented by formula (V')).

Examples of the novel coumarin derivative of the invention represented by formula (VI') include, but are not limited to, compounds B-102 to B-178.

Next, the novel Nile Red derivative of the invention will be described. Unless otherwise stated, the above description of the polymerizable liquid crystal composition of the invention will appropriately apply to the derivative.

The novel Nile Red derivative of the invention is a compound represented by formula (VII'), which corresponds to a compound represented by formula (VII) in which at least one of $R^{201}$ to $R^{206}$, $R^{209}$, and $R^{210}$ is a substituent represented by formula (V) (a substituent represented by formula (V')).

Examples of the novel Nile Red derivative of the invention represented by formula (VII') include, but are not limited to, compounds B-201 to B-225.

Next, the novel anthracene derivative of the invention will be described. Unless otherwise stated, the above description of the polymerizable liquid crystal composition of the invention will appropriately apply to the derivative.

The novel anthracene derivative of the invention is a compound represented by formula (VIII'), which corresponds to a compound represented by formula (VIII) in which at least one of $R^{301}$ to $R^{312}$ is a substituent represented by formula (V) (a substituent represented by formula (V')).

Examples of the novel anthracene derivative of the invention represented by formula (VIII') include, but are not limited to, compounds B-301 to B-312.

The novel naphtholactam, coumarin, Nile Red, and anthracene derivatives of the invention can be used as colorants for polarized light-emitting coating materials for a variety of applications, as dyes for optical recording layers for DVD-R and other media, as dyes for optical filters for image displays such as liquid crystal displays (LCDs), plasma display panels (PDPs), electroluminescence displays (ELDs), cathode ray tubes (CRTs), fluorescent display tubes, and field emission displays, as luminescent dyes for organic electroluminescence, as color toners, as inkjet ink, as paint dyes, as spectral sensitizing dyes for LED lighting, electroluminescence lighting, photoelectric transducers, and silver halide photography, or as sensitizers for photo-systems.

EXAMPLES

Hereinafter, the invention will be more specifically described with reference to examples, etc., which however are not intended to limit the invention.

Novel naphtholactam derivatives (B-33 and B-35) of the invention were synthesized in Examples 1-1 and 1-2 below.

Novel coumarin derivatives (B-169 to B-175) of the invention were synthesized in Examples 1-3 to 1-9 below.

Novel Nile Red derivatives (B-221 and B-222) of the invention were synthesized in Examples 1-10 and 1-11 below.

A novel anthracene derivative (B-308) of the invention was synthesized in Example 1-12 below.

In each of Examples 2-1 to 2-22 below, a polymerizable liquid crystal composition (polarized light-emitting coating material) of the invention was prepared, and a laminate of the invention capable of emitting polarized light (polarized light-emitting laminate) was prepared.

In each of Comparative Examples 2-1 and 2-2, a comparative polymerizable liquid crystal composition was prepared, and then a comparative laminate was prepared.

In Evaluation Examples 1-1 to 1-22 and Comparative Evaluation Examples 1-1 and 1-2, the polarized light-emitting laminates and the comparative laminates were evaluated for comparison. In each of Evaluation Examples 2-1 to 2-3, a polarized light-emitting medium was prepared using the polymerizable liquid crystal composition of the invention containing a polymerizable liquid crystal compound having an optically active group, and then subjected to evaluation.

Example 1-1

Synthesis of Compound B-33

Compound B-33 was synthesized according to the process described below.

A three-neck flask was charged with mesyl chloride (0.14 g, 0.0012 mol) and tetrahydrofuran (THF) (4.29 g), and the mixture was cooled to −30° C. in a nitrogen atmosphere. To the reactive solution was added dropwise a suspension of intermediate 1 (300 mg, 0.001 mol) represented by the formula below and triethylamine (TEA) (0.12 g, 0.012 mol) in THF (4.29 g). After the mixture was stirred for 3 hours, TEA (0.12 g, 0.0012 mol) and butanol acrylate (0.14 g, 0.001 mol) were added to the mixture, and the mixture was returned to room temperature and stirred overnight. Chloroform and water were added to the mixture, and oil-water separation was performed until neutralization was completed. The organic solvent was removed by distillation. After the residue was separated by silica gel column chromatography (eluent: chloroform), the separated product was crystallized from methanol to give 0.06 g of the desired product, compound B-33 (14% yield). The desired product was identified by $^1$H-NMR analysis. The analysis results are shown in Tables 1 and 2.

[Chemical Formula 71]

Intermediate 1

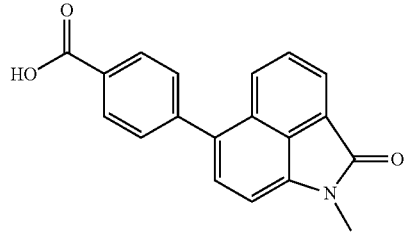

Example 1-2

Synthesis of Compound B-35

Compound B-35 was synthesized according to the process described below.

A three-neck flask was charged with mesyl chloride (0.34 g, 0.003 mol) and THF (6.18 g), and the mixture was cooled to −30° C. in a nitrogen atmosphere. To the reactive solution was added dropwise a suspension of intermediate 2 (0.73 g, 0.0025 mol) represented by the formula below and TEA (0.03 g, 0.003 mol) in THF (6.18 g). After a solution of TEA (0.03 g, 0.003 mol) and N,N-dimethylaminopyridine (DMAP) (0.003 g) in THF (6.18 g) was further added to the mixture, a solution of intermediate 3 (0.86 g, 0.0025 mol) represented by the formula below in THF (6.18 g) was added to the mixture. The mixture was returned to room temperature and stirred overnight. After chloroform and water were added to the mixture, oil-water separation was performed, and the organic solvent was removed by distillation. After the residue was separated by silica gel column chromatography (eluent: chloroform:n-hexane=1:1), the separated product was crystallized from methanol to give 0.48 g of the desired product, compound B-35 (31% yield). The desired product was identified by $^1$H-NMR analysis. The analysis results are shown in Tables 1 and 2.

[Chemical Formula 72]

Intermediate 2

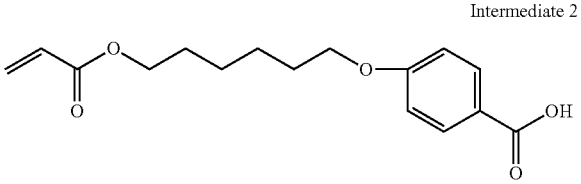

[Chemical Formula 73]

Intermediate 3

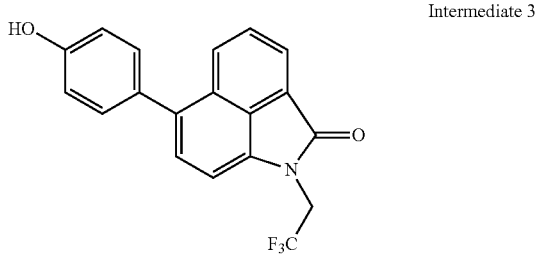

Examples 1-3 to 1-9

Synthesis of Compounds B-169 to B-175

Compound B-169 was synthesized according to the process shown below.

<Step 1>

A 300 ml four-neck flask was charged with salicylaldehyde (2.93 g, 0.024 mol), benzyloxyphenyl acetate (4.85 g, 0.02 mol), sodium acetate (3.28 g, 0.040 mol), and acetic anhydride (26.27 g), and the mixture was heated at 130° C. for 5 hours. The product was added dropwise to an aqueous sodium hydroxide solution. The resultant white precipitate was separated by filtration and washed with methanol under reflux. The white solid was then separated by filtration to give 2.4 g of intermediate 4 represented by the formula below (36.5% yield).

[Chemical Formula 74]

Intermediate 4

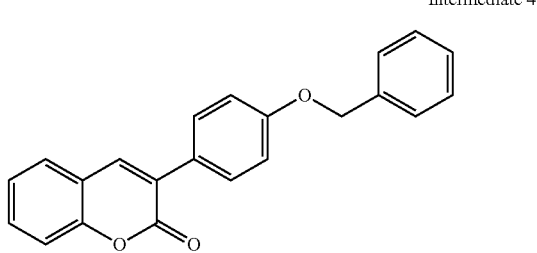

<Step 2>

A 300 ml four-neck flask was charged with intermediate 4 (2.17 g, 0.066 mol) obtained in step 1 and anisole (9.43 g). An anisole solution (1.57 g) of aluminum chloride (0.44 g, 0.033 mol) was added dropwise to the mixture and heated at 85° C. for 1 hour. Chloroform and water were added to the mixture, and the organic layer was dried with magnesium sulfate. Subsequently, the solvent was removed by distillation, and the resultant solid was washed with 20 g of diethyl ether. The solid was then dried at 80° C. to give 1.0 g of intermediate 5 represented by the formula below (63.6% yield).

[Chemical Formula 75]

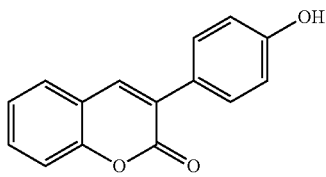

Intermediate 5

<Step 3>

A 300 ml four-neck flask was charged with mesyl chloride (0.28 g, 0.002 mol) and THF (4.1 g), and the mixture was cooled to −30° C. in a nitrogen atmosphere. A solution of TEA (0.24 g, 0.0024 mol) and 4-(6-acryloxy-hex-1-yloxy) benzoic acid (0.56 g, 0.002 mol) in THF (4.1 g) was added dropwise to the mixture and stirred at 0° C. for 2 hours. After a solution of TEA (0.24 g, 0.0024 mol) and DMAP (0.002 g) in THF (4.1 g) was further added to the mixture, intermediate 5 (0.48 g, 0.002 mol) obtained in step 2 was added to the mixture. The mixture was returned to room temperature and stirred overnight. The organic layer was extracted. After the solvent was removed by distillation, the residue was separated by silica gel column chromatography (eluent: chloroform). The separated product was crystallized from a chloroform/methanol system and dried under reduced pressure at room temperature to give 0.74 g of the desired product, compound B-169 (72.2% yield).

Compounds B-170 to B-175 were also synthesized in a similar manner to the process of synthesizing B-169. The resultant compounds were identified by $^1$H-NMR analysis. The results are shown in Tables 1 and 2.

Examples 1-10 and 1-11

Synthesis of Compounds B-221 and B-222

Compound B-221 was synthesized according to the process shown below.
<Step 1>

A 300 ml four-neck flask was charged with diethylamino nitrosophenol hydrochloride (1.15 g, 0.05 mol), 1,7-dihydroxynaphthalene (0.80 g, 0.05 mol), and dimethylformamide (DMF) (6.69 g), and the mixture was heated at 150° C. for 3 hours. The product was added dropwise to 250 g of an aqueous 10% sodium chloride solution. The resultant red precipitate was separated by filtration and washed with acetone under reflux. The red solid was then separated by filtration to give 0.65 g of intermediate 6 represented by the formula below (38.9% yield).

[Chemical Formula 76]

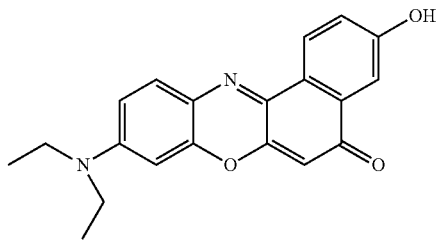

Intermediate 6

<Step 2>

A 300 ml four-neck flask was charged with mesyl chloride (0.25 g, 0.0022 mol) and THF (4.38 g). In a nitrogen atmosphere at −30° C., a solution of TEA (0.22 g, 0.0022 mol) and 4-(6-acryloxy-hex-1-yloxy)benzoic acid (0.53 g, 0.0018 mol) in THF (4.38 g) was added dropwise to the mixture and stirred at 0° C. for 2 hours. After a solution of TEA (0.22 g, 0.0022 mol) and DMAP (0.002 g) in THF (4.38 g) was further added to the mixture, intermediate 6 (0.60 g, 0.0018 mol) obtained in step 1 was added to the mixture. The mixture was stirred at room temperature overnight. The organic layer was extracted. After the solvent was removed by distillation, the residue was separated by silica gel column chromatography (eluent: chloroform:ethyl acetate=20:1). The separated product was crystallized from methanol and dried under reduced pressure at 40° C. to give 0.77 g of the desired product, compound B-221 (70.3% yield).

Compounds B-222 was also synthesized in a similar manner to the process of synthesizing B-221. The resultant compounds were identified by $^1$H-NMR analysis. The results are shown in Tables 1 and 2.

Examples 1-12

Synthesis of Compound B-308

Compound B-308 was synthesized according to the process shown below.
<Step 1>

A 300 ml four-neck flask was charged with 9,10-dibromoanthracene (0.84 g, 0.0025 mol), potassium phosphate (2.12 g, 0.005 mol), tetrakis(triphenylphosphine)palladium (0) (0.29 g, 0.000025 mol), and boron pinacol ester (1.21 g, 0.0055 mol). In an argon atmosphere, DMF (4.53 g) was added to the mixture and heated at 80° C. for 5 hours and at 110° C. for 2 hours. Chloroform, water, and hydrochloric acid were added to the mixture. After the aqueous layer was acidified, oil-water separation was performed. The separated product was crystallized from acetone, and the resultant white solid was separated by filtration to give 0.63 g of 9,10-bis(4-hydroxyphenyl)anthracene (69.5% yield).

<Step 2>

A 300 ml four-neck flask was charged with mesyl chloride (0.22 g, 0.00192 mol) and THF (7.29 g). In a nitrogen atmosphere at −30° C., a solution of TEA (0.19 g, 0.00192 mol) and 4-(6-acryloxy-hex-1-yloxy)benzoic acid (0.47 g, 0.0016 mol) in THF (7.29 g) was added dropwise to the mixture and stirred at 0° C. for 2 hours. After a solution of TEA (0.19 g, 0.00192 mol) and DMAP (0.002 g) in THF (7.29 g) was further added to the mixture, 9,10-bis(4-hydroxyphenyl)anthracene (0.29 g, 0.0008 mol) obtained in step 1 was added to the mixture. The mixture was stirred at room temperature overnight. The organic layer was extracted. After the solvent was removed by distillation, the residue was separated by silica gel column chromatography (eluent: chloroform). The separated product was crystallized from chloroform/methanol and dried under reduced pressure at 40° C. to give 0.41 g of a white solid (56.3% yield).

The resultant white solid was identified by $^1$H-NMR analysis as compound B-308. The results are shown in Tables 1 and 2.

TABLE 1

| | Compound | λ max (nm) | ε (×10$^1$) | Decomposition point (° C.) |
|---|---|---|---|---|
| Example 1-1 | Compound B-33 | 386.5 | 0.826 | 371.7 |
| Example 1-2 | Compound B-35 | 378.5 | 0.796 | 375.5 |
| Example 1-3 | Compound B-169 | 330.5 | 1.81 | 387.7 |
| Example 1-4 | Compound B-170 | 363.5 | 2.25 | 376.6 |
| Example 1-5 | Compound B-171 | 364 | 2.18 | 390.9 |
| Example 1-6 | Compound B-172 | 366.5/336.0 | 1.50/1.89 | 377.1 |
| Example 1-7 | Compound B-173 | 367.0/329.0 | 1.62/2.70 | 376.1 |
| Example 1-8 | Compound B-174 | 395.5 | 1.57 | 211 |
| Example 1-9 | Compound B-175 | 353.4 | — | — |
| Example 1-10 | Compound B-221 | 539 | 4.78 | 329 |
| Example 1-11 | Compound B-222 | 539 | 4.94 | 326.7 |
| Example 1-12 | Compound B-308 | 373 | 2.53 | 382.4 |

TABLE 2

| | Compound | 1H-NMR |
|---|---|---|
| Example 1-1 | Compound B-33 (DMSO-d6) | 1.81(6H, m), 3.40(3H, s), 4.19(2H, t), 4.35(2H, t), 5.93(1H, dd), 6.16(1H, td), 6.30(1H, dd), 7.27(1H, d), 7.61(1H, d), 7.72(2H, d), 7.83(2H, t), 8.11(4H, m) |
| Example 1-2 | Compound B-35 (CDCl$_3$) | 1.52(2H, m), 1.73(2H, m), 1.86(2H, m), 4.07(2H, t), 4.19(2H, t), 4.57(2H, q), 5.83(1H, dd), 6.13(1H, dd), 6.41(1H, dd), 7.00(2H, d), 7.11(1H, d), 7.36(2H, d), 7.52(1H, d), 7.59(2H, d), 7.78(1H, dd), 8.20(4H, m) |
| Example 1-3 | Compound B-169 (DMSO-d6) | 8.31(1H, s), 8.08(2H, d), 7.83(2H, d), 7.79(1H, d), 7.63(1H, t), 7.44(1H, d), 7.39(1H, t), 7.36(2H, d), 7.11(2H, d), 6.31(1H, dd), 6.16(1H, dd), 5.92(1H, dd), 4.11(4H, m), 1.74(2H, m), 1.43(4H, m) |
| Example 1-4 | Compound B-170 (CDCl$_3$) | 8.63(1H, s), 8.32(1H, d), 8.18(2H, d), 8.01(1H, d), 7.94(1H, d), 7.88(2H, d), 7.72(1H, t), 7.60(1H, t), 7.53(1H, d), 7.35(2H, d), 6.99(2H, d), 6.41(1H, dd), 6.15(1H, dd), 5.83(1H, dd), 4.21(2H, t), 4.07(2H, t), 1.86(2H, m), 1.72(2H, m), 1.53(4H, m) |
| Example 1-5 | Compound B-171 (CDCl$_3$) | 8.73(1H, s), 8.64(1H, s), 8.33(1H, d), 8.18(1H, d), 7.92(4H, m), 7.82(1H, d), 7.72(1H, t), 7.60(1H, t), 7.53(1H, d), 7.41(2H, d), 7.24(1H, d), 7.18(1H, s), 6.41(1H, dd), 6.13(1H, dd), 5.82(1H, dd), 4.20(2H, t), 4.12(2H, t), 1.90(2H, m), 1.77(2H, m), 1.55(4H, m) |
| Example 1-6 | Compound B-172 (CDCl$_3$) | 8.61(1H, m), 8.17(2H, d), 7.98(1H, s), 7.91(1H, m), 7.86(2H, d), 7.72(1H, d), 7.66(2H, m), 7.54(1H, d), 7.33(2H, d), 6.99(2H, d), 6.41(1H, dd), 6.13(1H, dd), 5.83(1H, dd), 4.19(2H, t), 4.06(2H, t), 1.85(2H, m), 1.74(2H, m), 1.53(4H, m) |
| Example 1-7 | Compound B-173 (CDCl$_3$) | 8.73(1H, s), 8.61(1H, s), 8.17(2H, d), 7.99(1H, s), 7.89(4H, m), 7.81(1H, d), 7.70(1H, d), 7.68(2H, m), 7.55(1H, d), 7.39(2H, d), 7.23(1H, d), 7.19(1H, s), 6.41(1H, dd), 6.13(1H, dd), 5.82(1H, dd), 4.20(2H, t), 4.13(2H, t), 1.90(2H, m), 1.73(2H, m), 1.55(4H, m) |
| Example 1-8 | Compound B-174 (CDCl$_3$) | 8.59(2H, d), 8.52(1H, m), 8.17(2H, d), 7.92(1H, m), 7.83(2H, q), 7.68(2H, m), 7.39(2H, d), 6.99(2H, d), 6.41(1H, dd), 6.13(1H, dd), 5.83(1H, dd), 4.20(2H, t), 4.07(2H, t), 1.86(2H, m), 1.75(2H, m), 1.50(4H, m) |
| Example 1-9 | Compound B-175 (CDCl$_3$) | 8.15(2H, d), 7.74(2H, d), 7.64(1H, s), 7.24(2H, d), 6.97(2H, d), 6.92(1H, s), 6.41(1H, dd), 6.13(1H, dd), 5.83(1H, dd), 4.19(2H, t), 4.06(2H, t), 3.28(4H, q), 2.94(2H, t), 2.78(2H, t), 2.00-1.51(16H, m) |
| Example 1-10 | Compound B-221 (DMSO-d6) | 8.71(1H, d), 8.17(2H, d), 8.11(1H, d), 7.62(1H, d), 7.61(1H, dd), 6.98(2H, d), 6.68(1H, dd), 6.48(1H, dd), 6.43(1H, dd), 6.43(1H, s), 6.13(1H, dd), 5.83(1H, dd), 4.19(2H, t), 4.06(2H, t), 3.47(4H, q), 1.85(2H, m), 1.74(2H, m), 1.51(4H, m), 1.27(6H, t) |
| Example 1-11 | Compound B-222 (CDCl$_3$) | 8.73(2H, d), 8.18(2H, d), 7.90(1H, d), 7.81(1H, d), 7.66(1H, dd), 7.63(1H, d), 7.23(1H, dd), 7.18(1H, s), 6.69(1H, dd), 6.45(2H, dd), 6.42(1H, dd), 6.13(1H, dd), 5.82(1H, dd), 4.20(2H, t), 4.12(2H, t), 3.48(4H, q), 1.88(2H, m), 1.75(2H, m), 1.55(4H, m), 1.27(6H, t) |
| Example 1-12 | Compound B-308 (CDCl$_3$) | 8.24(4H, d), 7.75(4H, dd), 7.52(4H, d), 7.46(4H, d), 7.37(4H, dd), 7.03(4H, d), 6.42(2H, dd), 6.16(2H, dd), 5.83(2H, dd), 4.20(4H, t), 4.09(4H, t), 1.84(4H, m), 1.75(4H, m), 1.53(8H, m) |

Examples 2-1 to 2-22 and Comparative Examples 1-1 and 1-2

Preparation of Polymerizable Liquid Crystal Composition of the Invention and Comparative Polymerizable Liquid Crystal Composition and Preparation of Polarized Light-Emitting Laminate of the Invention and Comparative Laminate Polymerizable liquid crystal compositions were prepared according to procedure [1] described below (Preparation of Polymerizable Liquid Crystal Composition Solution). A polarized light-emitting laminate of the invention and a comparative laminate were prepared from the polymerizable liquid crystal composition of the invention and the comparative polymerizable liquid crystal composition, respectively, according to procedure [2] described below (Application to Substrate and Curing).

[1] Preparation of Polymerizable Liquid Crystal Composition Solution

According to the formulation shown in Table 3 below, the polymerizable liquid crystal compound (A), the colorant (dye compound) (B), the polymerization initiator (C), and the solvent were mixed, and SURFLON S-242 (manufactured by AGC Seimi Chemical Co., Ltd.) as a leveling agent was added to the mixture. Ultrasound was applied to the mixture for 10 minutes so that the mixture was completely dissolved. The solution was then filtered through a 0.45 μm filter, so that a polymerizable liquid crystal composition solution of the invention or a comparative polymerizable liquid crystal composition solution was obtained.

[2] Application to Substrate and Curing

The polymerizable liquid crystal composition solution of the invention or the comparative polymerizable liquid crystal composition solution prepared according to procedure [1] above was applied to a rubbed polyimide-coated glass substrate using a spin coater (at 1,200 rpm for 10 seconds). When the application was performed, the speed and period of rotation of the spin coater were controlled so that a coating with a thickness of about 1 to about 3 μm could be formed. After the application, the coating was dried at 100° C. for 1 minute using a hot plate and then cooled at room temperature for 1 to 10 minutes. Subsequently, the coating was cured by exposure to light at 300 mJ/cm$^2$ using a high-pressure mercury lamp, so that the coating was cured and a polarized light-emitting laminate of the invention and a comparative laminate were each obtained.

Evaluation Examples 1-1 to 1-22 and Comparative Evaluation Examples 1-1 and 1-2

The polarized light-emitting media obtained in Examples 2-1 to 2-22 and the comparative media obtained in Comparative Examples 2-1 and 2-2 were each measured for UV absorption spectrum and fluorescence spectrum in a case where the angle between the medium and the rubbing direction of the glass substrate was 0° (0°) and in a case where the angle between the medium and the rubbing direction of the glass substrate was 90° (90°), and the degree of absorption polarization and the polarized light emission rate were calculated from the formulae below. These results are shown in Tables 3A and 3B. The higher the degree of absorption polarization and the polarized light emission rate, the stronger and better the polarized light emission.

Degree of absorption polarization=[(0° absorbance*[1])−(90° absorbance*[2])/0° absorbance]×100

Polarized light emission rate=[(0° fluorescence intensity*[3]−90° fluorescence intensity*[4])/0° fluorescence intensity]×100   <Formulae>

*1: the absorbance at the λmax wavelength in the 0° UV absorption spectrum
*2: the absorbance at the *1 wavelength in the 90° UV absorption spectrum
*3: the fluorescence intensity at the λmax wavelength in the 0° fluorescence spectrum
*4: the fluorescence intensity at the *3 wavelength in the 90° fluorescence spectrum

TABLE 3A

| | Polymerizable liquid crystal composition | | | | Physical properties | |
| --- | --- | --- | --- | --- | --- | --- |
| | Polymerizable liquid crystal compound (A) | Dye compound (B) | Polymerization initiator (C) | Solvent | Degree of absorption polarization | Polarized light emission rate |
| Example 2-1 | Compound A-84 250 mg | Compound B-101 2 mg | Compound C-1*[1] 7.5 mg | Solvent 1*[4] 1 g | 75.1 | 74 |
| Example 2-2 | Compound A-134 250 mg | Compound B-101 2 mg | Compound C-2*[2] 7.5 mg | Solvent 1 1 g | 57.3 | 45.8 |
| Example 2-3 | Compound A-20 250 mg | Compound B-101 2 mg | Compound C-2 7.5 mg | Solvent 1 1 g | 71.8 | 73.7 |
| Example 2-4 | Compound A-20 250 mg | Compound B-49 20 mg | Compound C-2 7.5 mg | Solvent 2*[5] 1 g | 33.7 | 44.9 |
| Example 2-5 | Compound A-20 250 mg | Compound B-50 20 mg | Compound C-2 7.5 mg | Solvent 3*[6] 1 g | 59 | 70.6 |
| Example 2-6 | Compound A-20 250 mg | Compound B-51 20 mg | Compound C-2 7.5 mg | Solvent 3 1 g | 8 | 47.9 |
| Example 2-7 | Compound A-20 250 mg | Compound B-29 20 mg | Compound C-2 7.5 mg | Solvent 3 1 g | 69.8 | 66 |

TABLE 3A-continued

| | Polymerizable liquid crystal composition | | | | Physical properties | |
|---|---|---|---|---|---|---|
| | Polymerizable liquid crystal compound (A) | Dye compound (B) | Polymerization initiator (C) | Solvent | Degree of absorption polarization | Polarized light emission rate |
| Example 2-8 | Compound A-20 250 mg | Compound B-29 20 mg | Compound C-2 7.5 mg | Solvent 2 0.5 g | 70 | 55.1 |
| Example 2-9 | Compound A-20 250 mg | Compound B-29 10 mg | Compound C-2 7.5 mg | Solvent 2 0.5 g | 73.5 | 62.6 |
| Example 2-10 | Compound A-20 250 mg | Compound B-52 10 mg | Compound C-2 7.5 mg | Solvent 2 0.5 g | 67.9 | 54 |
| Example 2-11 | Compound A-20 250 mg | Compound B-33 10 mg | Compound C-2 7.5 mg | Solvent 2 0.5 g | 82.1 | 62.6 |
| Example 2-12 | Compound A-20 250 mg | Compound B-35 10 mg | Compound C-2 7.5 mg | Solvent 2 0.5 g | 82.3 | 76 |
| Example 2-13 | Compound A-20 250 mg | Compound B-35 10 mg | Compound C-2 7.5 mg | Solvent 2 0.5 g | 85.3 | 74.9 |

*[1]Compound C-1: N-1919, manufactured by ADEKA CORPORATION
*[2]Compound C-2: IRG 907, manufactured by BASF
*[3]Compound C-3: IRG 819, manufactured by BASF
*[4]Solvent 1: tetrafluoropropanol
*[5]Solvent 2: cyclopentanone
*[6]Solvent 3: methyl ethyl ketone

TABLE 3B

| | Polymerizable liquid crystal composition | | | | Physical properties | |
|---|---|---|---|---|---|---|
| | Polymerizable liquid crystal compound (A) | Dye compound (B) | Polymerization initiator (C) | Solvent | Degree of absorption polarization | Polarized light emission rate |
| Example 2-14 | Compound A-20 250 mg | Compound B-169 20 mg | Compound C-3*[3] 7.5 mg | Solvent 2 0.5 g | 85.4 | 71.5 |
| Example 2-15 | Compound A-20 250 mg | Compound B-170 10 mg | Compound C-3 7.5 mg | Solvent 2 0.5 g | 79.9 | 70.2 |
| Example 2-16 | Compound A-20 250 mg | Compound B-171 10 mg | Compound C-3 7.5 mg | Solvent 2 0.5 g | 78.9 | 75.5 |
| Example 2-17 | Compound A-20 250 mg | Compound B-172 10 mg | Compound C-3 7.5 mg | Solvent 2 0.5 g | 91 | 85.6 |
| Example 2-18 | Compound A-20 250 mg | Compound B-173 10 mg | Compound C-3 7.5 mg | Solvent 2 0.5 g | 92.9 | 85.7 |
| Example 2-19 | Compound A-20 250 mg | Compound B-174 10 mg | Compound C-3 7.5 mg | Solvent 2 0.5 g | 88.1 | 74.5 |
| Example 2-20 | Compound A-20 250 mg | Compound B-209 10 mg | Compound C-3 7.5 mg | Solvent 2 0.5 g | 79.4 | 82.6 |
| Example 2-21 | Compound A-20 250 mg | Compound B-210 10 mg | Compound C-3 7.5 mg | Solvent 2 0.5 g | 83.2 | 83.9 |
| Example 2-22 | Compound A-20 250 mg | Compound B-308 10 mg | Compound C-3 7.5 mg | Solvent 2 0.5 g | 93.5 | 77.9 |
| Comparative Example 2-1 | Compound A-84 250 mg | — | Compound C-1 7.5 mg | Solvent 1 0.5 g | — | — |
| Comparative Example 2-2 | Compound A-20 250 mg | — | Compound C-2 7.5 mg | Solvent 2 0.5 g | — | — |
| Comparative Example 2-3 | Compound A-20 250 mg | — | Compound C-3 7.5 mg | Solvent 2 0.5 g | — | — |

Evaluation Examples 2-1 to 2-3

According to the formulation shown in Table 4 below, the polymerizable liquid crystal compound (A), the colorant (dye compound) (B), the polymerization initiator (C), the solvent, and SURFLON S-242 (manufactured by AGC Seimi Chemical Co., Ltd.) as a leveling agent were mixed to form a polymerizable liquid crystal composition solution as in Examples 2-1 to 2-22, and the selective reflection wavelength and the reflectance were measured using the method described below.

<Measurement of Selective Reflection Wavelength>

The reflectance was measured at 25° C. in the wavelength range of 800 to 400 nm using a spectrophotometer (U-3010 manufactured by Hitachi High-Technologies Corporation) equipped with a 50 specular reflection accessory, and the selective reflection center wavelength (λ) was determined.

TABLE 4

| | Polymerizable liquid crystal composition | | | | Physical propertied | |
|---|---|---|---|---|---|---|
| | Polymerizable liquid crystal compound (A) | Dye compound (B) | Polymerization initiator (C) | Solvent | Selective reflection center wavelength | Reflectance |
| Evaluation Example 2-1 | Compound A-20/228 mg Compound A-128/22.0 mg | Compound B-35 10 mg | Compound C-2 7.5 mg | Solvent 2 1 g | 479 nm | 29.60% |
| Evaluation Example 2-2 | Compound A-20/225 mg Compound A-128/25.0 mg | Compound B-35 10 mg | Compound C-2 7.5 mg | Solvent 2 1 g | 425 nm | 27.20% |
| Evaluation Example 2-3 | Compound A-20/225 mg Compound A-128/19.5 mg | Compound B-35 10 mg | Compound C-2 7.5 mg | Solvent 2 1 g | 553 nm | 45.00% |

The results in Tables 3A and 3B show that laminates each produced using a polarized light-emitting coating material including a polymerizable liquid crystal composition of the invention emit linearly polarized light. Especially, it has been demonstrated that polarized light with a particularly high degree of polarization can be emitted using the novel naphtholactam derivative (B-1), the novel coumarin derivative (B-2), the novel Nile Red derivative (B-3), or the novel anthracene derivative (B-4) of the invention as the colorant (dye compound) (B). In addition, the results in Table 4 show that circularly polarized light with even selective reflection at a specific wavelength can be emitted using an optically active group-containing polymerizable liquid crystal compound as the polymerizable liquid crystal compound (A).

The invention claimed is:
1. A polymerizable liquid crystal composition, comprising:
    (A) at least one liquid crystal compound having a polymerizable functional group,
    (B) at least one colorant, and
    (C) a polymerization initiator, wherein (B) is represented by formula (VI):

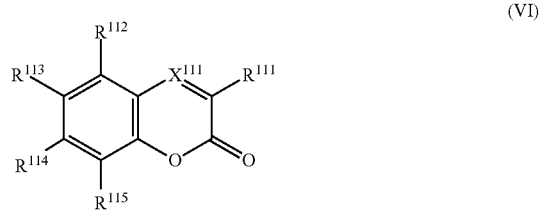

wherein
$X^{111}$ represents a nitrogen atom or $CR^{116}$, $R^{111}$ to $R^{116}$ each independently represent a hydrogen atom, a halogen atom, a nitro group, a cyano group, an aldehyde group, a carboxyl group, a hydroxyl group, —NRR', an organosilyl group, an optionally substituted alkyl group of 1 to 30 carbon atoms, an optionally substituted aryl group of 6 to 30 carbon atoms, an optionally substituted arylalkyl group of 7 to 30 carbon atoms, an optionally substituted heterocyclic group of 2 to 30 carbon atoms, or a substituent represented by formula (V),
a methylene chain in the alkyl group or the arylalkyl group represented by each of $R^{111}$ to $R^{116}$ may be interrupted by —O—, —S—, —SO$_2$—, —CO—, —OCO—, or —COO—, the aryl group represented by each of $R^{111}$ to $R^{116}$ and the coumarin structure may be linked together via —O—, —S—, —SO$_2$—, —CO—, —OCO—, or —COO—, and the methylene chain may be replaced by —CH=CH— or —C≡C—,
adjacent two or more of $R^{111}$ to $R^{116}$ may be linked together to form a ring, or when any one of $R^{111}$ to $R^{116}$ is —NRR', R or R' and any other one of $R^{111}$ to $R^{116}$ adjacent thereto may be linked together to form a ring,
R and R' each independently represent a hydrogen atom, an optionally substituted alkyl group of 1 to 30 carbon atoms, or an optionally substituted aryl group of 6 to 30 carbon atoms,
a methylene chain in the alkyl group represented by each of R and R' may be interrupted by —O—, —S—, —SO$_2$—, —CO—, —OCO—, or —COO—, the aryl group represented by each of R and R' and the coumarin structure may be linked together via —O—, —S—, —SO$_2$—, —CO—, —OCO—, or —COO—, and the methylene chain may be replaced by —C=C— or —C≡C—, at least one of $R^{111}$ to $R^{116}$ represents a substituent represented by formula (V):

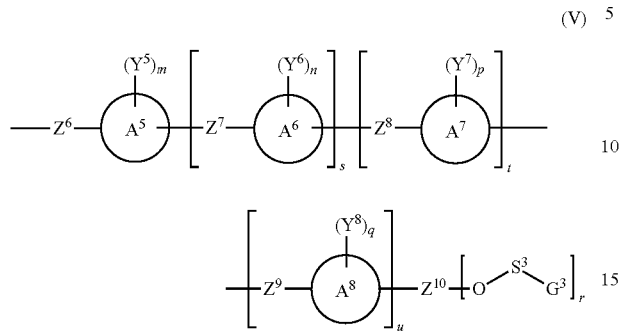
(V)

wherein $A^5$, $A^6$, $A^7$, and $A^8$ each independently represent a benzene ring, a cyclohexane ring, a cyclohexene ring, a naphthalene ring, a decahydronaphthalene ring, or a tetrahydronaphthalene ring, $S^3$ represents an alkylene group of 1 to 8 carbon atoms, the alkylene group represented by $S^3$ may be substituted with a halogen atom and branched, and a methylene chain in the alkylene group represented by $S^3$ may be substituted with a halogen atom, branched, and interrupted by -O-, $Z^6$, $Z^7$, $Z^8$, $Z^9$, and $Z^{10}$ each independently represent a direct bond, -L²-, —O—CO—, —CO—O—, -L²O-, —OL²-, -L²O—CO—, -L²CO—O—, -L²O—CO—O—, —O—COL²-, —CO—OL²-, —O—CO—OL²-, —CO—CH=CH, —CH=CH—CO—, —CH=CH—COO—, —CH=CH—OCO—, —COO—CH=CH—, —OCO—CH=CH—, or —CH₂=N—N=CH₂—, $L^2$ represents an alkylene group of 1 to 8 carbon atoms, the alkylene group may be branched and may be substituted with a halogen atom or a cyano group, and a methylene chain in the alkylene group represented by L2 may be interrupted by -O-, —CH=CH—, or —C≡C—, $Y^5$, $Y^6$, $Y^7$ and $Y^8$ each independently represent an alkyl group of 1 to 6 carbon atoms, a halogen atom, or a cyano group, a hydrogen atom of the alkyl group represented by each of $Y^5$, $Y^6$, $Y^7$ and $Y^8$ may be substituted with a halogen atom or a cyano group, and a methylene chain in the alkyl group represented by each of $Y^5$, $Y^6$, $Y^7$ and $Y^8$ may be interrupted by -O- or —CO—, m, n, p, and q are each independently from 0 to 8, s is 1, t and u are each independently 0 or 1, r is 1 or 2, and $G^3$ represents a substituent selected from the group consisting of substituents represented by formulae (5) to (14) below:

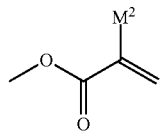
(5)

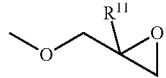
(6)

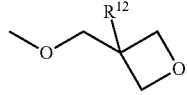
(7)

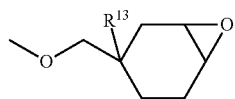
(8)

(9)

(10)

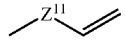
(11)

(12)

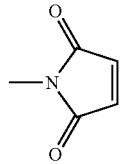
(13)

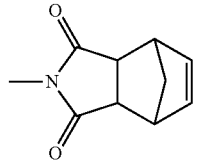
(14)

wherein in formula (5), $M^2$ represents a hydrogen atom, a methyl group, or a halogen atom; in formula (6), $R^{11}$ represents a hydrogen atom or an alkyl group of 1 to 6 carbon atoms; in formula (7), $R^{12}$ represents a hydrogen atom or an alkyl group of 1 to 6 carbon atoms; in formula (8), $R^{13}$ represents a hydrogen atom or an alkyl group of 1 to 6 carbon atoms; in formula (9), $R^{14}$ represents a hydrogen atom or an alkyl group of 1 to 6 carbon atoms; and in formula (11), $Z^{11}$ represents methylene, an oxygen atom, or —CO—.

2. The polymerizable liquid crystal composition according to claim 1, wherein the liquid crystal compound as the component (A) having a polymerizable functional group is a liquid crystal compound represented by formula (I):

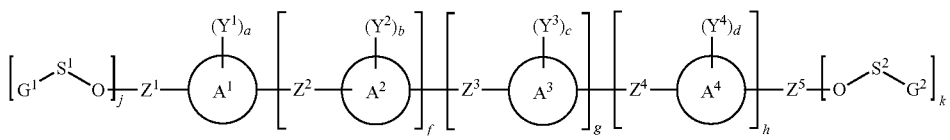

wherein
- rings $A^1$, $A^2$, $A^3$, and $A^4$ each independently represent a benzene ring, a cyclohexane ring, a cyclohexene ring, a naphthalene ring, an anthracene ring, a phenanthrene ring, a decahydronaphthalene ring, a tetrahydronaphthalene ring, or an optically active linking group,
- $S^1$ and $S^2$ each independently represent an alkylene group of 1 to 8 carbon atoms, the alkylene group represented by each of $S^1$ and $S^2$ may be substituted with a halogen atom and may be branched, and a methylene chain in the alkylene group represented by each of $S^1$ and $S^2$ may be interrupted by —O—,
- $Z^1$, $Z^2$, $Z^3$, $Z^4$, and $Z^5$ each independently represent a direct bond, $-L^1-$, —O—CO—, —CO—O—, $-L^1O-$, —$OL^1-$, $-L^1O$—CO—, $-L^1CO$—O—, $-L^1O$—CO—O—, —O—$COL^1-$, —CO—$OL^1-$, —O—CO—$OL^1-$, —CO—CH=CH—, —CH=CH—CO—, —CH=CH—COO—, —CH=CH—OCO—, —COO—CH=CH—, —OCO—CH=CH, or —$CH_2$=N—N=$CH_2$—,
- $L^1$ represents an alkylene group of 1 to 8 carbon atoms, the alkylene group may be branched and may be substituted with a halogen atom or a cyano group, and the alkylene group represented by $L^1$ may be interrupted by —O—, —CH=CH—, or —C≡C—,
- $Y^1$, $Y^2$, $Y^3$, and $Y^4$ each independently represent an alkyl group of 1 to 6 carbon atoms, a halogen atom, or a cyano group, a hydrogen atom of the alkyl group represented by each of $Y^1$, $Y^2$, $Y^3$ and $Y^4$ may be substituted with a halogen atom or a cyano group, and a methylene chain in the alkyl group represented by each of $Y^1$, $Y^2$, $Y^3$ and $Y^4$ may be interrupted by —O— or —CO—,
- a, b, c, and d are each independently from 0 to 8, and f, g, and h are each independently 0 or 1,
- j and k are each independently 0, 1, or 2, provided that j+k≥2, and
- $G^1$ and $G^2$ each independently represent a substituent selected from the group consisting of substituents represented by formulae (1) to (4):

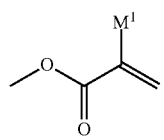

(1)

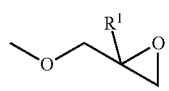

(2)

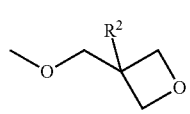

(3)

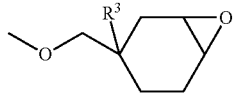

(4)

wherein in formula (1), $M^1$ represents a hydrogen atom, a methyl group, or a halogen atom; in formula (2), $R^1$ represents a hydrogen atom or an alkyl group of 1 to 6 carbon atoms; in formula (3), $R^2$ represents a hydrogen atom or an alkyl group of 1 to 6 carbon atoms; and in formula (4), $R^3$ represents a hydrogen atom or an alkyl group of 1 to 6 carbon atoms.

3. The polymerizable liquid crystal composition according to claim 1, wherein the colorant as the component (B) is a fluorescent dye.

4. The polymerizable liquid crystal composition according to claim 1, wherein the colorant as the component (B) is a fluorescent dye having a luminophore and a mesogenic structure.

5. A polarized light-emitting coating material comprising the polymerizable liquid crystal composition according to claim 1.

6. A polarized light-emitting laminate comprising a support and a coating obtained by applying, to the support, the polarized light-emitting coating material according to claim 5.

7. A polarized light-emitting laminate comprising a polymer obtained by photopolymerization of the polymerizable liquid crystal composition according to claim 1.

8. A polarizing device comprising the laminate according to claim 6.

9. A coumarin derivative represented by formula (VI'):

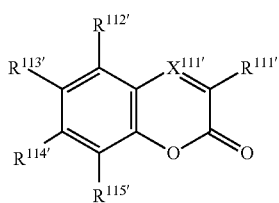

(VI')

wherein
$X^{111'}$ represents a nitrogen atom or $CR^{116'}$, $R^{111'}$ to $R^{116'}$ each independently represent a hydrogen atom, a halogen atom, a nitro group, a cyano group, an aldehyde group, a carboxyl group, a hydroxyl group, —NR"R'", an organosilyl group, an optionally substituted alkyl group of 1 to 30 carbon atoms, an optionally substituted aryl group of 6 to 30 carbon atoms, an optionally substituted arylalkyl group of 7 to 30 carbon atoms, an optionally substituted heterocyclic group of 2 to 30 carbon atoms, or a substituent represented by formula (V'), a methylene chain in the alkyl group or the arylalkyl group represented by each of $R^{111'}$ to $R^{116'}$ may be interrupted by —O—, —S—, —SO$_2$—, —CO—, —OCO—, or —COO—, the aryl group represented by each of $R^{111'}$ to $R^{116'}$ and the coumarin structure may be linked together via —O—, —S—, —SO$_2$—, —CO—, —OCO—, or —COO—, and the methylene chain may be replaced by —CH=CH— or —C≡C—, adjacent two or more of $R^{111'}$ to $R^{116'}$ may be linked together to form a ring, or when any one of $R^{111'}$ to $R^{116'}$ is —NR'R''', R'' or R''' and any other one of $R^{111'}$ to $R^{116'}$ adjacent thereto may be linked together to form a ring, R'' and R''' each independently represent a hydrogen atom, an optionally substituted alkyl group of 1 to 30 carbon atoms, or an optionally substituted aryl group of 6 to 30 carbon atoms, a methylene chain in the alkyl group represented by each of R'' and R''' may be interrupted by —O—, —S—, —SO$_2$—, —CO—, —OCO—, or —COO—, the aryl group represented by each of R'' and R''' and the coumarin structure may be linked together via —O—, —S—, —SO$_2$—, —CO—, —OCO—, or —COO—, and the methylene chain may be replaced by —C=C— or —C≡C—, and at least one of $R^{111'}$ to $R^{116'}$ represents a substituent represented by formula (V'):

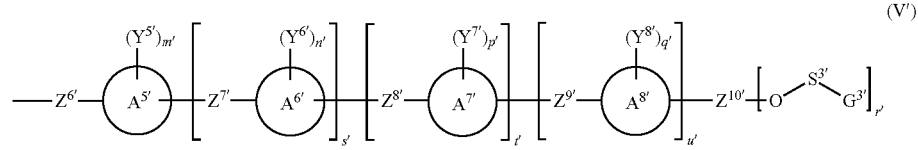

(V')

wherein
rings $A^{5'}$, $A^{6'}$, $A^{7'}$, and $A^{8'}$ each independently represent a benzene ring, a cyclohexane ring, a cyclohexene ring, a naphthalene ring, a decahydronaphthalene ring, or a tetrahydronaphthalene ring, $S^{3'}$ represents an alkylene group of 1 to 8 carbon atoms, the alkylene group represented by $S^{3'}$ may be substituted with a halogen atom and branched, and a methylene chain in the alkylene group represented by $S^{3'}$ may be interrupted by —O—, $Z^{6'}$, $Z^{7'}$, $Z^{8'}$, $Z^{9'}$, and $Z^{10'}$ each independently represent a direct bond, -L$^{2'}$-, —O—CO—, —CO—O—, -L$^{2'}$O—, —OL$^{2'}$-, -L$^{2'}$O—CO—, -L$^{2'}$CO—O—, -L$^{2'}$O—CO—O—, —O—COL$^{2'}$-, —CO—OL$^{2'}$-, —O—CO—OL$^{2'}$-, —CO—CH=CH—, —CH=CH—CO—, —CH=CH—COO—, —CH=CH—OCO—, —COO—CH=CH—, —OCO—CH=CH—, or —CH$_2$=N—N=CH$_2$—, L$^{2'}$ represents an alkylene group of 1 to 8 carbon atoms, the alkylene group may be branched and may be substituted with a halogen atom or a cyano group, and a methylene chain in the alkylene group represented by L$^2$ may be interrupted by —O—, —CH=CH—, or —C≡C—, $Y^{5'}$, $Y^{6'}$, $Y^{7'}$, and $Y^{8'}$ each independently represent an alkyl group of 1 to 6 carbon atoms, a halogen atom, or a cyano group, a hydrogen atom of the alkyl group represented by each of $Y^{5'}$, $Y^{6'}$, $Y^{7'}$ and $Y^{8'}$ may be substituted with a halogen atom or a cyano group, and a methylene chain in the alkyl group represented by each of $Y^{5'}$, $Y^{6'}$, $Y^{7'}$ and $Y^{8'}$ may be interrupted by —O— or —CO—, m', n', p', and q' are each independently from 0 to 8, s' is 1, t', and u' are each independently 0 or 1, r' is 1 or 2, and $G^{3'}$ represents a substituent selected from the group consisting of substituents represented by formulae (5') to (14'):

(5')

(6')

-continued

(7')

(8')

(9')

(10')

(11')

(12')

-continued

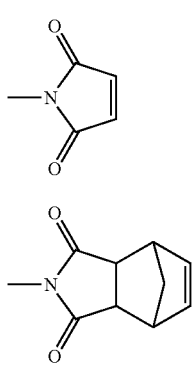

(13′)

(14′)

wherein in formula (5′), $M^{2'}$ represents a hydrogen atom, a methyl group, or a halogen atom; in formula (6′), $R^{11'}$ represents a hydrogen atom or an alkyl group of 1 to 6 carbon atoms; in formula (7′), $R^{12'}$ represents a hydrogen atom or an alkyl group of 1 to 6 carbon atoms; in formula (8′), $R^{13'}$ represents a hydrogen atom or an alkyl group of 1 to 6 carbon atoms; in formula (9′), $R^{14'}$ represents a hydrogen atom or an alkyl group of 1 to 6 carbon atoms; and in formula (11′), $Z^{11'}$ represents methylene, an oxygen atom, or —CO—.

* * * * *